United States Patent
Solanki et al.

(10) Patent No.: US 9,008,391 B1
(45) Date of Patent: Apr. 14, 2015

(54) SYSTEMS AND METHODS FOR PROCESSING RETINAL IMAGES FOR SCREENING OF DISEASES OR ABNORMALITIES

(71) Applicant: EYENUK, Inc., Woodland Hills, CA (US)

(72) Inventors: Kaushal Mohanlal Solanki, Woodland Hills, CA (US); Sandeep Bhat Krupakar, Woodland Hills, CA (US); Chaithanya Amai Ramachandra, Woodland Hills, CA (US); Malavika Bhaskaranand, Woodland Hills, CA (US)

(73) Assignee: EYENUK, Inc., Woodland Hills, CA (US)

( * ) Notice: Subject to any disclaimer, the term of this patent is extended or adjusted under 35 U.S.C. 154(b) by 0 days.

(21) Appl. No.: 14/266,753

(22) Filed: Apr. 30, 2014

Related U.S. Application Data

(60) Provisional application No. 61/893,885, filed on Oct. 22, 2013.

(51) Int. Cl.
*G06K 9/00* (2006.01)
*G06K 9/62* (2006.01)
*A61B 13/00* (2006.01)
*G06T 7/00* (2006.01)
*A61B 3/14* (2006.01)

(52) U.S. Cl.
CPC ............ *G06T 7/0012* (2013.01); *G06K 9/0061* (2013.01); *A61B 3/14* (2013.01)

(58) Field of Classification Search
None
See application file for complete search history.

(56) References Cited

U.S. PATENT DOCUMENTS

| | | | |
|---|---|---|---|
| 5,878,746 | A | 3/1999 | Lemelson et al. |
| 6,454,410 | B1 | 9/2002 | Berger et al. |
| 7,474,775 | B2 | 1/2009 | Abràmoff et al. |
| 7,522,745 | B2 | 4/2009 | Grasso et al. |
| 7,782,464 | B2 | 8/2010 | Mujat et al. |

(Continued)

FOREIGN PATENT DOCUMENTS

| | | |
|---|---|---|
| CA | 2797725 A1 | 11/2011 |
| CN | 101589301 B | 11/2012 |

(Continued)

OTHER PUBLICATIONS

Abdi et al., "Principal component analysis." Wiley Interdisciplinary Reviews: Computational Statistics, 2(4):433459, 1-47, 2010.

(Continued)

*Primary Examiner* — Wenpeng Chen
(74) *Attorney, Agent, or Firm* — Smyrski Law Group, A PC

(57) ABSTRACT

Embodiments disclose systems and methods that aid in screening, diagnosis and/or monitoring of medical conditions. The design includes a system and method for accessing retinal images related to a patient, each retinal image including a plurality of pixels. For each of the retinal images, the system designates a first set of the plurality of pixels as active pixels including interesting retinal image regions and computes a first vector of numbers comprising pixel-level descriptors for each of the active pixels. The system computes a second vector of numbers for each of the retinal images and provides a second classification using supervised learning.

27 Claims, 58 Drawing Sheets

(56) References Cited

U.S. PATENT DOCUMENTS

| | | | |
|---|---|---|---|
| 7,856,135 | B1 | 12/2010 | Bernardes |
| 8,041,091 | B2 | 10/2011 | De Oliveira e Ramos et al. |
| 8,340,437 | B2 | 12/2012 | Abramoff |
| 8,355,544 | B2 | 1/2013 | Gómez-Ulla de Irazazábal et al. |
| 8,515,201 | B1 | 8/2013 | Murray Herrera et al. |
| 8,687,862 | B2 | 4/2014 | Hsu et al. |
| 2002/0141626 | A1 | 10/2002 | Caspi |
| 2003/0039380 | A1* | 2/2003 | Sukegawa et al. ............ 382/118 |
| 2003/0174872 | A1 | 9/2003 | Chalana et al. |
| 2004/0064057 | A1 | 4/2004 | Siegel |
| 2004/0105074 | A1 | 6/2004 | Soliz et al. |
| 2006/0257031 | A1* | 11/2006 | Abramoff et al. ............ 382/224 |
| 2007/0127795 | A1 | 6/2007 | Lau et al. |
| 2007/0258630 | A1 | 11/2007 | Tobin et al. |
| 2008/0240581 | A1* | 10/2008 | Napoletani et al. .......... 382/224 |
| 2009/0323022 | A1 | 12/2009 | Uchida |
| 2010/0061601 | A1* | 3/2010 | Abramoff et al. ............ 382/117 |
| 2010/0111396 | A1* | 5/2010 | Boucheron ................... 382/133 |
| 2010/0142767 | A1* | 6/2010 | Fleming ....................... 382/117 |
| 2010/0183217 | A1* | 7/2010 | Seung et al. .................. 382/156 |
| 2010/0249532 | A1 | 9/2010 | Maddess et al. |
| 2011/0026789 | A1* | 2/2011 | Hsu et al. ...................... 382/128 |
| 2011/0160562 | A1 | 6/2011 | De Oliveira e Ramos et al. |
| 2011/0182517 | A1 | 7/2011 | Farsiu et al. |
| 2011/0200242 | A1* | 8/2011 | Takama et al. ................ 382/131 |
| 2011/0242306 | A1* | 10/2011 | Bressler et al. ................ 348/78 |
| 2012/0027275 | A1* | 2/2012 | Fleming ....................... 382/128 |
| 2012/0123232 | A1 | 5/2012 | Najarian et al. |
| 2012/0140175 | A1 | 6/2012 | Everett et al. |
| 2012/0150029 | A1 | 6/2012 | Debuc |
| 2012/0177262 | A1 | 7/2012 | Bhuiyan |
| 2012/0184845 | A1* | 7/2012 | Ishikawa et al. ............. 600/425 |
| 2012/0236259 | A1 | 9/2012 | Abramoff et al. |
| 2012/0249959 | A1 | 10/2012 | You et al. |
| 2012/0257164 | A1* | 10/2012 | Zee et al. ...................... 351/206 |
| 2012/0317107 | A1* | 12/2012 | Bedrax-Weiss et al. ...... 707/731 |
| 2013/0195340 | A1* | 8/2013 | Iwase et al. ................... 382/131 |

FOREIGN PATENT DOCUMENTS

| | | |
|---|---|---|
| EP | 1427338 A2 | 6/2004 |
| GB | 2467840 A | 8/2010 |
| GB | 2470727 A | 12/2010 |
| WO | WO 01/87145 A2 | 11/2001 |
| WO | WO 02/15818 | 2/2002 |
| WO | WO 03020112 A2 | 3/2003 |
| WO | WO 03/030073 A1 | 4/2003 |
| WO | WO 2011/066366 A1 | 6/2011 |
| WO | WO 2012/149687 A1 | 11/2012 |

OTHER PUBLICATIONS

Abràmoff et al., "Evaluation of a system for automatic detection of diabetic retinopathy from color fundus photographs in a large population of patients with diabetes." Diabetes Care, 31(2), 193-198, Feb. 2008.

Aibinu et al., Vascular intersection detection in retina fundus images using a new hybrid approach. Elsevier Computers and Biology and Medicine, 1-34, Nov. 2009.

Ausayakhun et al., "Accuracy and reliability of telemedicine for diagnosis of cytomegalovirus retinitis." American Journal of Ophthalmology, 152(6):1053-1058.e1, Dec. 2011.

Ausayakhun et al., "Clinical features of newly diagnosed cytomegalovirus retinitis in northern Thailand." American Journal of Ophthalmology, 153(5):923-931.e1, May 2012.

Barriga et al., "Automatic system for diabetic retinopathy screening based on AM-FM, partial least squares, and support vector machines.", In 2010 IEEE International Symposium on Biomedical Imaging: From Nano to Macro, pp. 1349-1352, 2010.

Belongie et al., Shape matching and object recognition using shape contexts. IEEE Trans. Pattern Analysis and Machine Intelligence (PAMI), 24(4):509-522, Apr. 2005.

Berisha et al.,"Retinal Abnormalities in Early Alzheimer's Disease," Investigative Ophthalmology & Visual Science 48, No. 5 (May 1, 2007): 2285-2289.

Can et al. "A feature-based technique for joint, linear estimation of high-order image-to-mosaic transformations: mosaicing the curved human retina." IEEE Transactions on Pattern Analysis and Machine Intelligence, 24(3):412-419, 2002.

Can et al., "A feature-based, robust, hierarchical algorithm for registering pairs of images of the curved human retina." IEEE Transactions on Pattern Analysis and Machine Intelligence, 24(3):347-364, 2002.

Canny, "A computational approach to edge detection." IEEE Transactions on Pattern Analysis and Machine Intelligence, vol. 8, Issue 6 pp. 679-698, 1986.

Chum et al., "Randomized RANSAC with td, d test." In Proc. British Machine Vision Conference, vol. 2, pp. 448-457, 2002.

Chum et al., Matching with PROSAC- progressive sample consensus. In Computer Vision and Pat-tern Recognition, 2005. CVPR 2005. IEEE Computer Society Conference on, vol. 1, pp. 220-226, 2005.

Ciresan et al., "Multi-column deep neural networks for image classification." arXiv e-print 1202.2745, Feb. 2012. CVPR 2012, p. 3642-3649.

Diabetes Control and Complications Trial Research Group. Progression of retinopathy with intensive versus conventional treatment in the diabetes control and complications trial. Ophthalmology, PMID:7724182, 102(4):647-661, Apr. 1995.

Drucker et al., "Support vector regression machines." Advances in neural information processing systems, pp. 155-161, 1997.

Frango et al., "Multiscale vessel enhancement filtering in Medical Image Computing and Computer-Assisted Intervention," MICCAI98, pp. 130-137. Springer, 1998.

Giancardo et al., Quality assessment of retinal fundus images using elliptical local vessel density. New Developments in Biomedical Engineering, Ed. Domenico Campolo, INTECH. http://sciyo.com/books/show/title/new-developments-in-biomedical-engineering, 201-224, 2010.

Hamman et al., "Prevalence and risk factors of diabetic retinopathy in non-hispanic whites and hispanics with NIDDM": san luis valley diabetes study. Diabetes, 38(10):1231-1237, 1989.

Harris et al., "Is the Risk of Diabetic Retinopathy Greater in Non-Hispanic Blacks and Mexican Americans Than in Non-Hispanic Whites With Type 2 Diabetes?": A US population study. Diabetes Care, 21(8):1230-1235, 1998.

Hart et al., "Measurement and classification of retinal vascular tortuosity." International Journal of Medical Informatics, 53(23):239-252, Feb. 1999.

Hartley et al., "Multiple view geometry in computer vision", vol. 2. Cambridge University Press, 2000.

Hashimoto et al., "Referenceless image quality evaluation for whole slide imaging." Journal of pathology informatics, 3:9, 2012. PMID: 22530177.

Hoover et al., "Locating blood vessels in retinal images by piecewise threshold probing of a matched filter response." IEEE Transactions on Medical Imaging, 19(3):203-210, 2000.

Hubbard et al., "Methods for evaluation of retinal microvascular abnormalities associated with hypertension/sclerosis in the atherosclerosis risk in communities study." Ophthalmology, 106(12):2269-2280,Dec. 1999. PMID: 10599656.

Jarrett et al., "What is the best multi-stage architecture for object recognition? In Computer Vision", 2009 IEEE 12th International Conference on, p. 2146-2153, 2009.

Karnowski et al., Retina lesion and microaneurysm segmentation using morphological reconstruction methods with groundtruth data. In 30th Annual International Conference of the IEEE Engineering in Medicine and Biology Society, pp. 5433-5436, Aug. 2008.

Kauppi et al., Diaretdb1 diabetic retinopathy database and evaluation protocol. In 11th Conference on Medical Image Understanding and Analysis, 2007.

Knudtson et al., "Revised formulas for summarizing retinal vessel diameters." Current eye research, 27(3):143-149, Sep. 2003. PMID: 14562179.

(56) References Cited

OTHER PUBLICATIONS

Kodovsky et al., "Ensemble classifiers for steganalysis of digital media." Information Forensics and Security, IEEE Transactions on, 7(2):432444, 2012.
Lalonde et al., "Fast and robust optic disc detection using pyramidal decomposition and Hausdorff-based template matching." IEEE Transactions on Medical Imaging, 20(11):1193-1200, 2001.
Lowe et al., Distinctive image features from scale-invariant keypoints. International Journal of Computer Vision, 60(2):91-110, 2004.
Ma et al., Netra: A toolbox for navigating large image databases. In IEEE International Conference on Image Processing, vol. 1, pp. 568-571, Oct. 1997.
MacQueen, James "Some methods for classification and analysis of multivariate observations." In Proceedings of the fifth Berkeley symposium on mathematical statistics and probability, vol. 1, pp. 281-297, 167.
Manjunath et al., "Texture features for browsing and retrieval of image data." IEEE Trans. Pattern Analysis and Machine Intelligence (Special issue on Digital Libraries), 18(8):837-842, Aug. 1996.
Manning et al., "Introduction to information retrieval", vol. 1. Cambridge University Press Cambridge, 2008.
Merz, Christopher, "Using correspondence analysis to combine classifiers." Machine Learning, 36(1-2):33-58, Jul. 1999.
Mo, Lingfei, et al., "Multi-sensor ensemble classifier for activity recognition." A Journal of Software Engineering and Applications,5:113-116, 2012.
Moreira-Matias et al., "Text categorization using an ensemble classifier based on a mean co-association matrix." In Machine Learning and Data Mining in Pattern Recognition, p. 525-539. Springer, 2012.
Márquez-Neila et al., "Speeding-up homography estimation in mobile devices." Journal of Real-Time Image Processing, Jan. 2013.
Nayar et al., "Shape from focus" IEEE Transactions on Pattern Analysis and Machine Intelligence, 16(8):824-831, 1994.
Niemeijer et al., Automated detection and differentiation of drusen, exudates, and cotton-wool spots in digital color fundus photographs for diabetic retinopathy diagnosis. Invest Ophthalmol Vis Sci, 48(5):2260-2267, May 2007.
Niemeijer et al., Information fusion for diabetic retinopathy cad in digital color fundus photographs. IEEE Transactions on Medical Imaging, 28(5):775-785, May 2009.
Olson et al., Evaluation of a system for automatic detection of diabetic retinopathy from color fundus photographs in a large population of patients with diabetes: response to Abramoff et al. Diabetes Care, 31(8), Aug. 2008.
Polikar R., "Ensemble based systems in decision making." IEEE Circuits and Systems Magazine, 6(3):21-45, 2006.
Quellec et al., "A multiple-instance learning framework for diabetic retinopathy screening." Medical Image Analysis, 16(6):1228-1240, Aug. 2012.
Rokach Lior, "Ensemble-based classifiers". Artificial Intelligence Review, 33(1-2):1-39, Feb. 2010.
Sanchez et al., "Evaluation of a computer-aided diagnosis system for diabetic retinopathy screening on public data." Investigative Ophthalmology & Visual Science, 52(7):4866-4871, Apr. 2011.
Scotland et al., Costs and consequences of automated algorithms versus manual grading for the detection of referable diabetic retinopathy. Br J Ophthalmol., Dec. 2009.
Sethian, J.A., "A fast marching level set method for monotonically advancing fronts." Proceedings of the National Academy of Sciences, 93(4):1591-1595, 1996.
Sill et al., "Feature-weighted linear stacking." arXiv e-print 0911.0460, Nov. 2009.
Sivic et al., Video google: a text retrieval approach to object matching in videos. In 9th IEEE International Conference on Computer Vision, pp. 1470-1477, 2003.
Smola et al., "A tutorial on support vector regression," Statistics and Computing, 14(3):199-222, 2004.
Staal et al., "Ridge-based vessel segmentation in color images of the retina." IEEE transactions on medical imaging, 23(4):501-509, Apr. 2004. PMID:15084075.
Ting et al., Issues in stacked generalization. Journal of Artificial Intelligence Research,10:271-289, 1999.
Tobin et al., "Using a patient image archive to diagnose retinopathy". In 30th Annual International Conference of the IEEE Engineering in Medicine and Biology Society, pp. 5441-5444, Aug. 2008.
Tomasi et al., Bilateral filtering for gray and color images. In Computer Vision, 1998. Sixth International Conference on, p. 839846, 1998.
Torr et al., "MLESAC: a new robust estimator with application to estimating image geometry." Computer Vision and Image Understanding, 78(1):138-156, 2000.
Varma et al., "Prevalence of Diabetic Retinopathy in Adult Latinos: The Los Angeles Latino Eye Study." Ophthalmology, 111(7):1298-1306, Jul. 2004. PMID: 15234129.
Weiss, Ben., "Fast Median and Bilateral Filtering," in *ACM Transactions on Graphics (TOG)*, vol. 25, 2006, 519-526
Whiting et al., IDF Diabetes Atlas: Global estimates of the prevalence of diabetes for 2011 and 2030. Diabetes research and clinical practice, 94(3):311-321, Dec. 2011. PMID: 22079683.
Wild et al., Global prevalence of diabetes estimates for the year 2000 and projections for 2030. Diabetes Care, 27(5):1047-1053, May 2004. PMID: 15111519.
Wolpert, David, Stacked generalization. Neural Networks, 5:241259, 1992.
Wong et al., "Cerebral White Matter Lesion, Retinopathy and Risk of Clinical Stroke: The Atherosclerosis Risk in the Communities Study". JAMA 2002;288:67-74, Jul. 2002.
Wong et al., "Retinopathy and risk of congestive heart failure" JAMA 2005; 293:63-69, Jan. 2005.
Zeiler et al., On rectified linear units for speech processing. 2013.
Dzeroski et al., "Is combining classifiers better than selecting the best one." In Machine Learning, p. 25273. Morgan kaufmann, 2004.
Zhang Harry, The optimality of naive bayes. A A, 1(2):3, 2004.
Zuliani, Marco., "RANSAC for dummies." Vision Research Lab, University of California, Santa Barbara, 2009.

\* cited by examiner

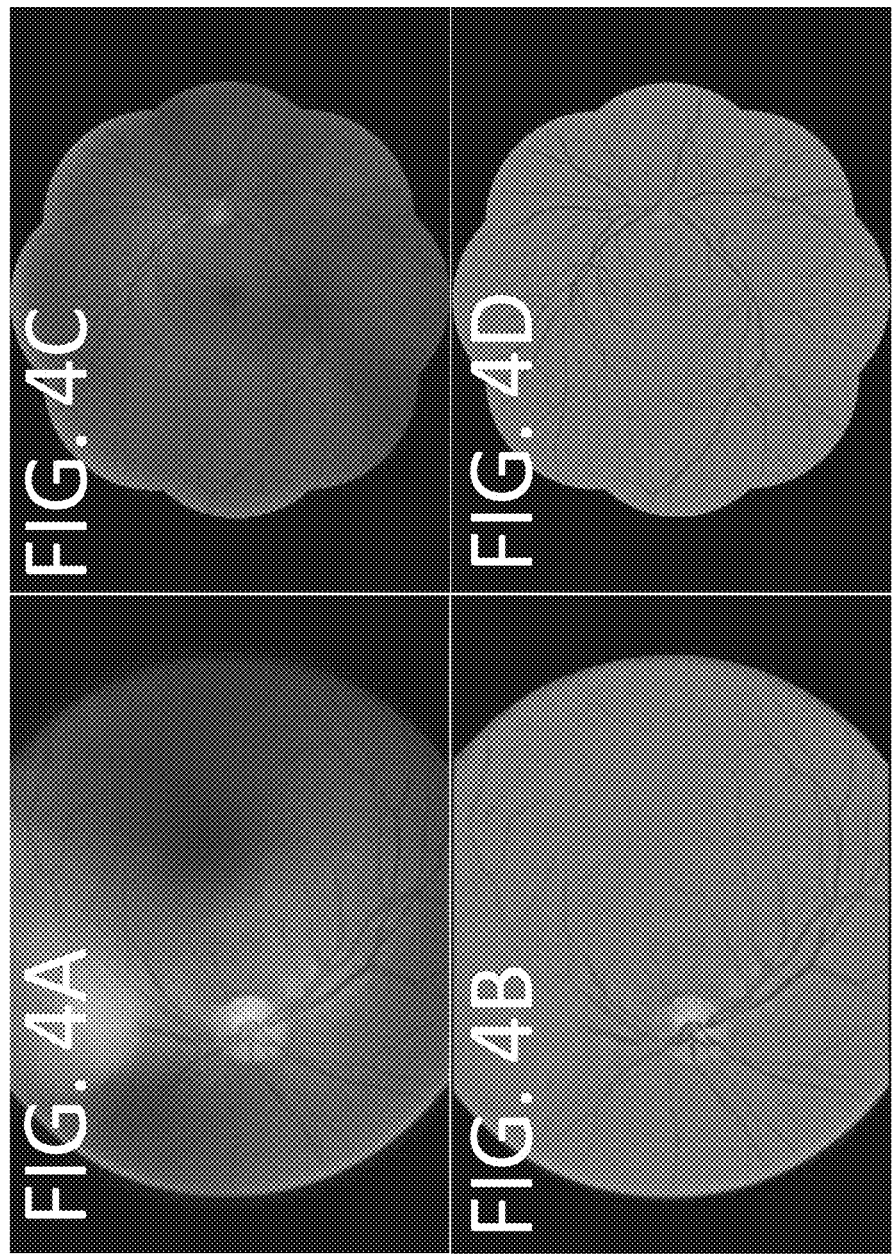

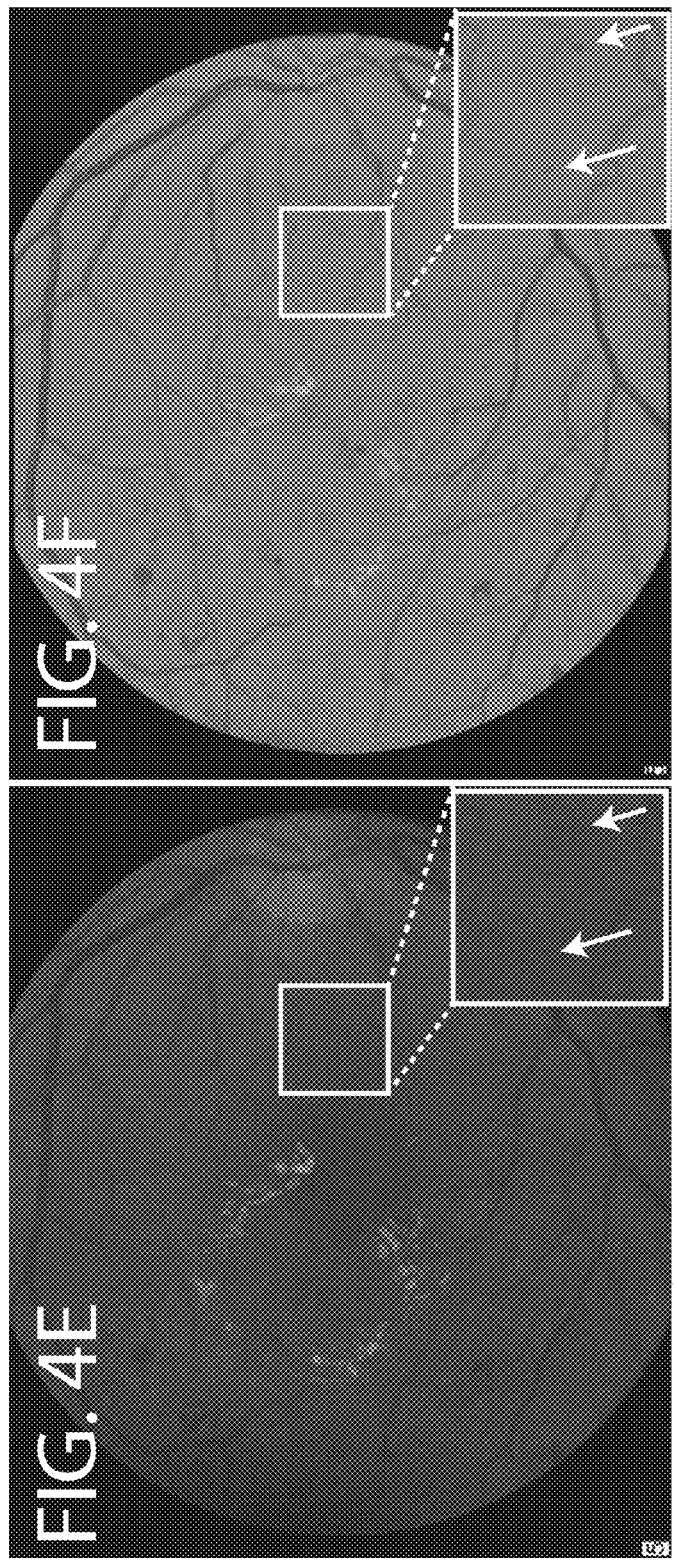

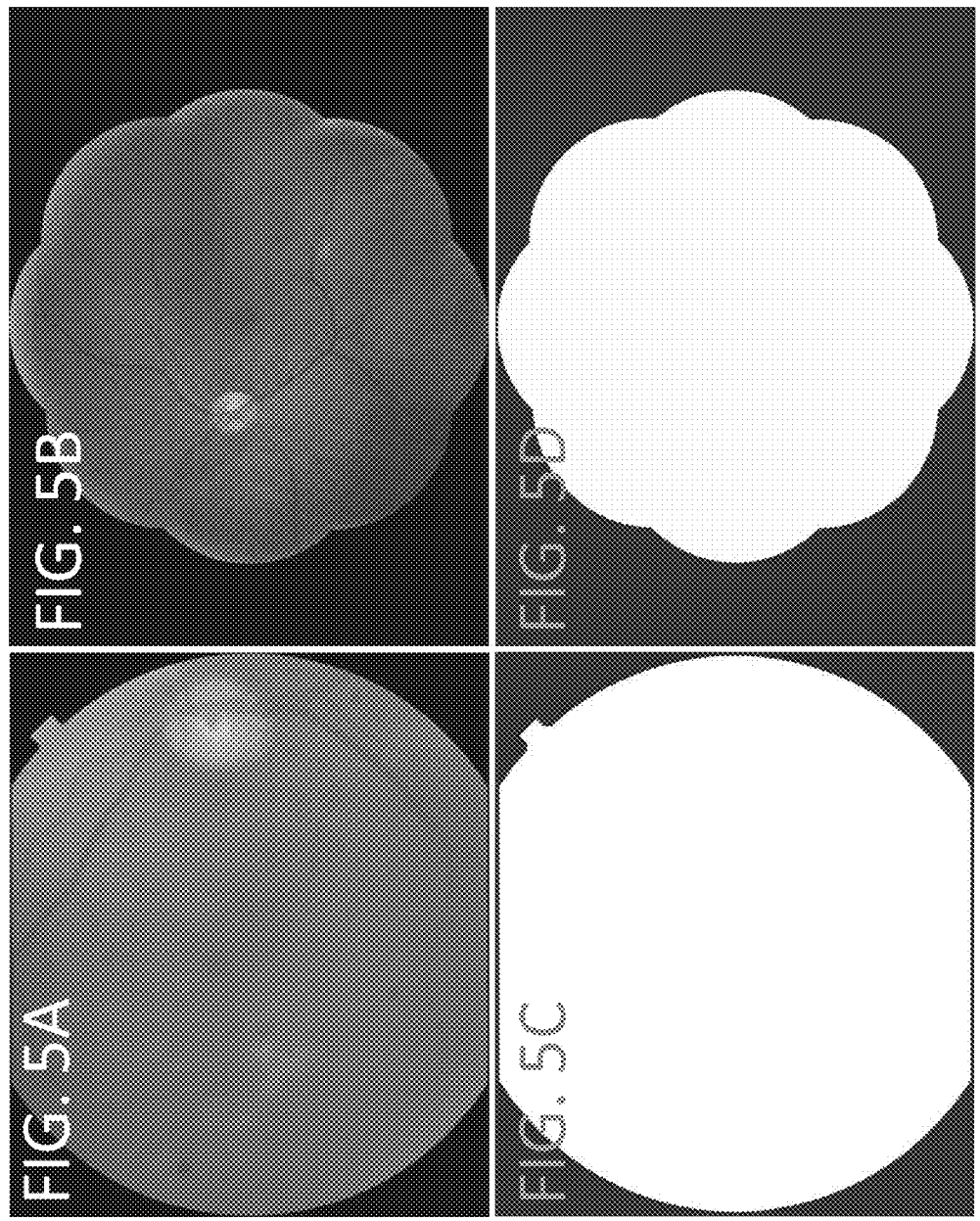

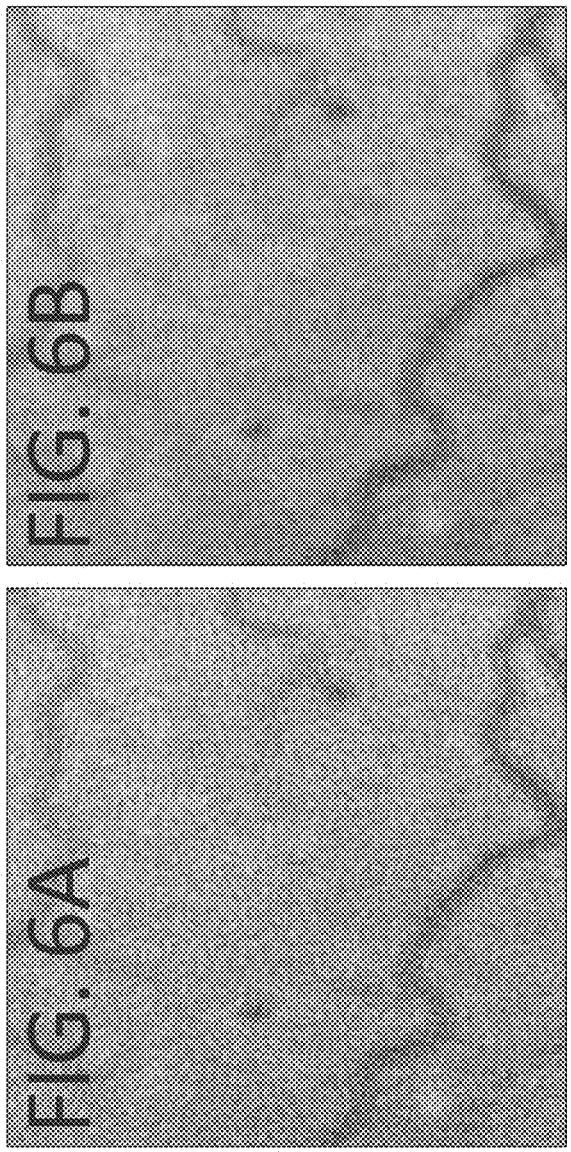

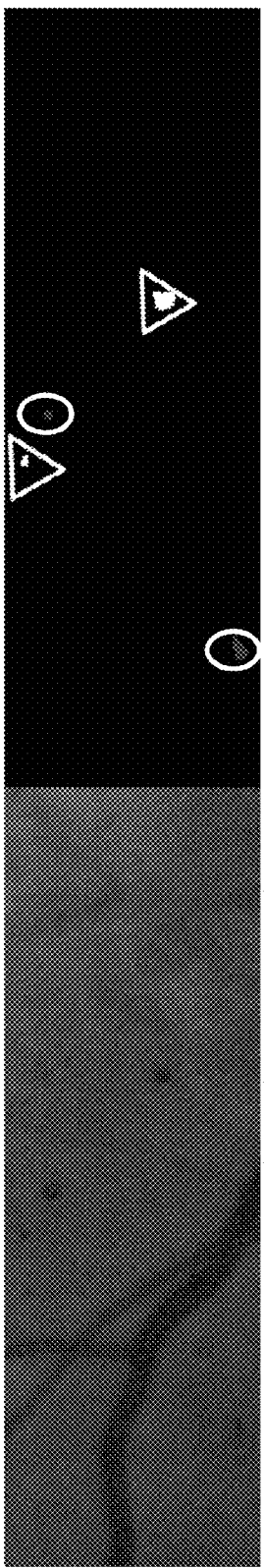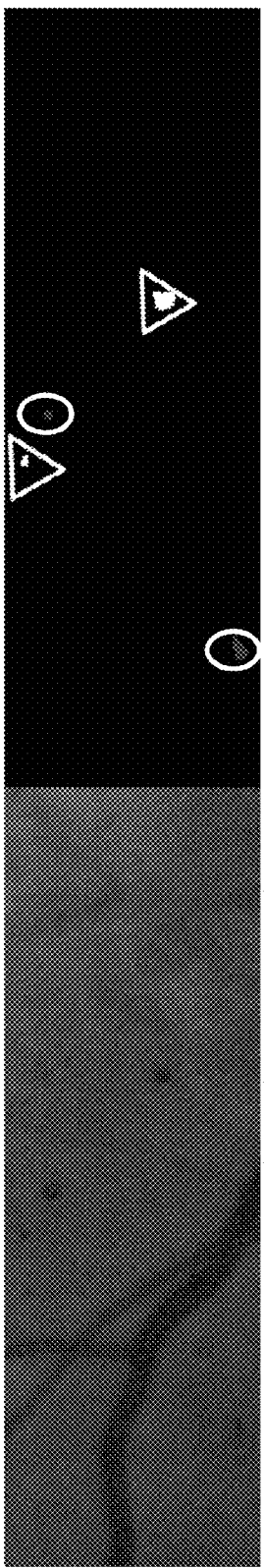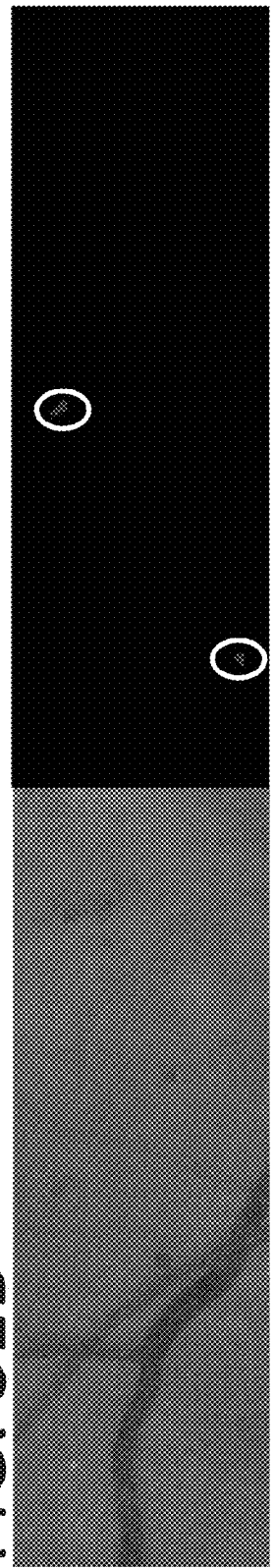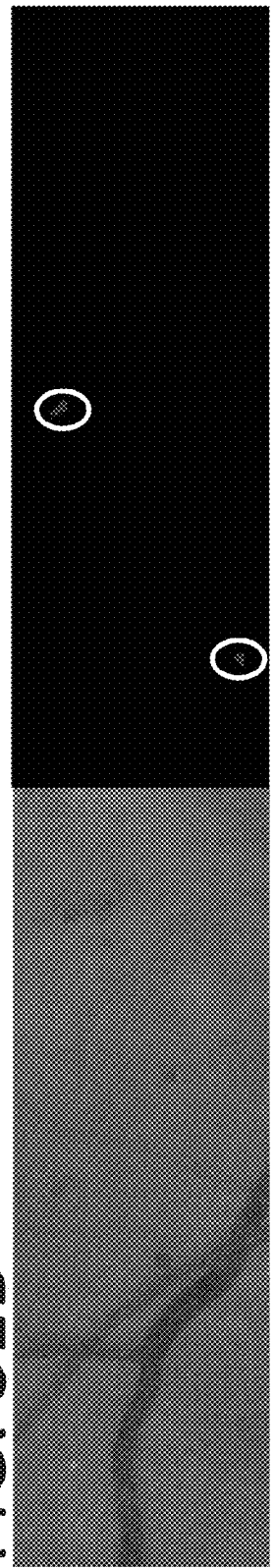

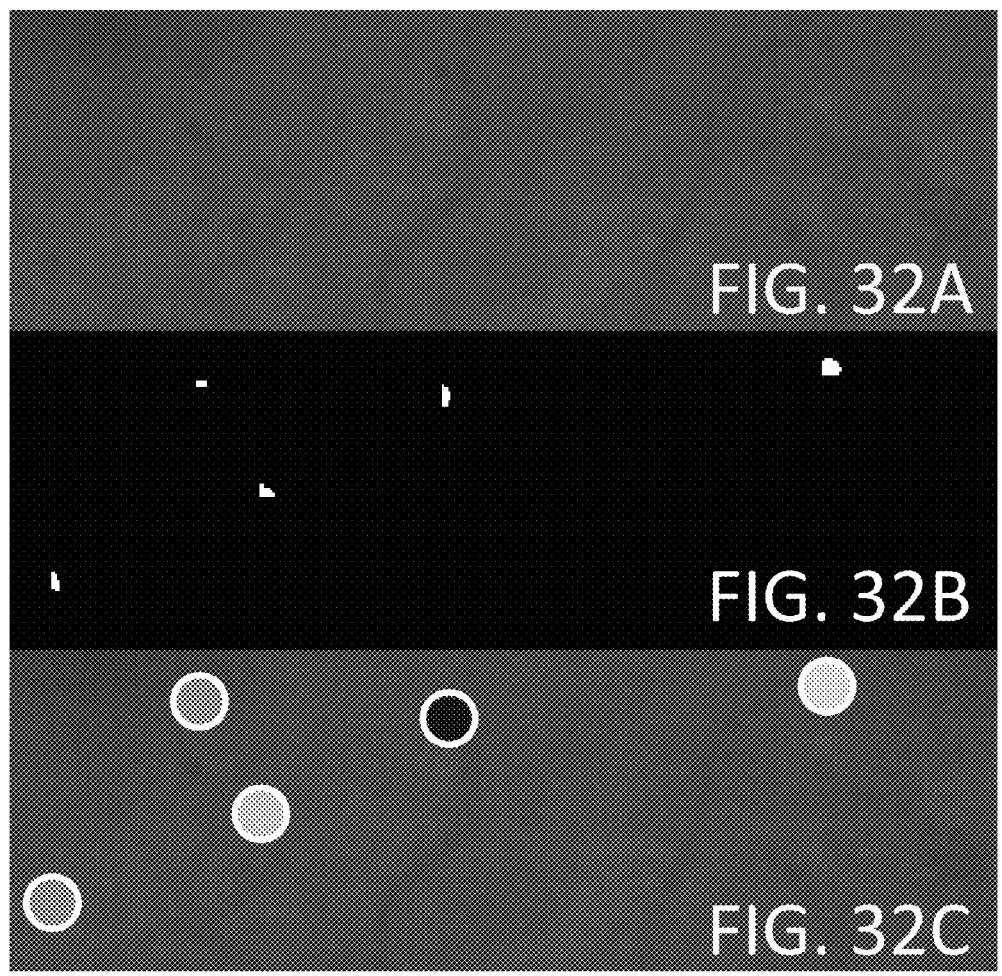

FIG. 36C

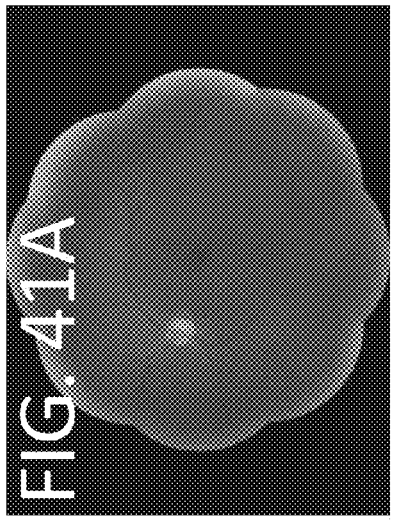
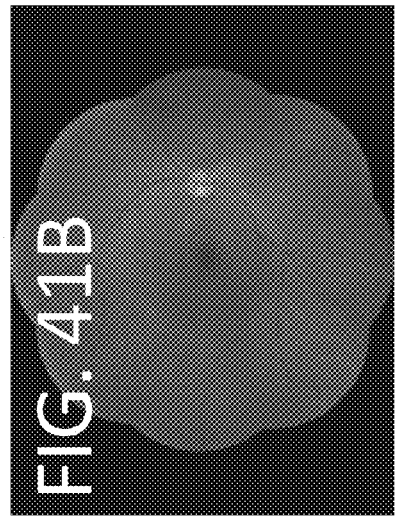
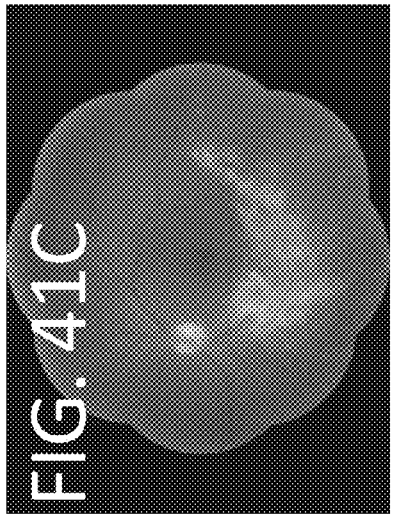
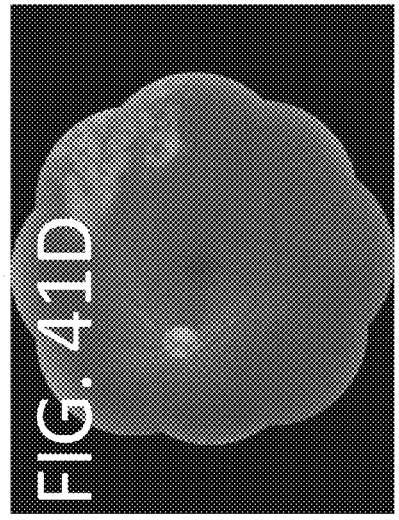
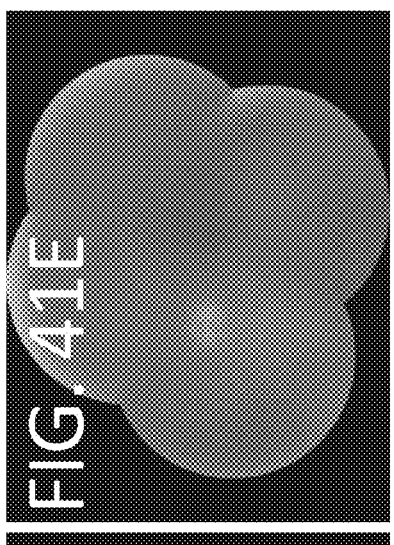
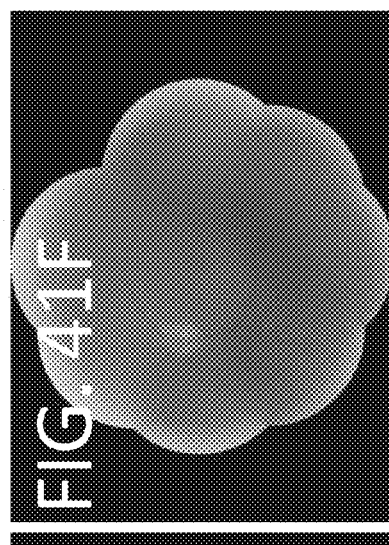

SYSTEMS AND METHODS FOR PROCESSING RETINAL IMAGES FOR SCREENING OF DISEASES OR ABNORMALITIES

PRIORITY INFORMATION

This application claims the benefit of priority under 35 U.S.C. §119(e) of U.S. Provisional Application No. 61/893,885, filed Oct. 22, 2013, entitled "SYSTEMS AND METHODS FOR COMPUTERIZED RETINAL IMAGE ANALYSIS AND COMPUTATION OF IMAGE-BASED BIOMARKERS," the entire content of which is hereby incorporated by reference herein in its entirety and should be considered a part of this specification. This application was filed on the same day as the following applications, U.S. patent application Ser. No. 14/266,688, titled System and Methods for Automated Enhancement of Retinal Images, U.S. patent application Ser. No. 14/266,749, titled Systems and Methods for Automated Interest Region Detection in Retinal Images, and U.S. patent application Ser. No. 14/266,746, titled Systems and Methods for Automatically Generating Descriptions of Retinal Images, all of which are hereby incorporated by reference in their entirety herein.

STATEMENT REGARDING FEDERALLY SPONSORED R&D

The inventions disclosed herein were made with government support under Grants EB013585 and TR000377 awarded by the National Institutes of Health. The government has certain rights in the invention.

BACKGROUND OF THE DISCLOSURE

Imaging of human organs plays a critical role in diagnosis of multiple diseases. This is especially true for the human retina, where the presence of a large network of blood vessels and nerves make it a near-ideal window for exploring the effects of diseases that harm vision (such as diabetic retinopathy seen in diabetic patients, cytomegalovirus retinitis seen in HIV/AIDS patients, glaucoma, and so forth) or other systemic diseases (such as hypertension, stroke, and so forth). Advances in computer-aided image processing and analysis technologies are essential to make imaging-based disease diagnosis scalable, cost-effective, and reproducible. Such advances would directly result in effective triage of patients, leading to timely treatment and better quality of life.

SUMMARY OF THE DISCLOSURE

In one embodiment a computing system for enhancing a retinal image is disclosed. The computing system may include one or more hardware computer processors; and one or more storage devices configured to store software instructions configured for execution by the one or more hardware computer processors in order to cause the computing system to: access a medial retinal image for enhancement, the medical retinal image related to a subject; compute a median filtered image $I_{Back,S}$ with a median computed over a geometric shape, at single or multiple scales; determine whether intensity at a first pixel location in the medical retinal image $I(x, y)$ is lower than intensity at a same position in the median filtered image $I_{Back,S}(x, y)$; if the intensities at the first pixel location is lower, then set a value at the first pixel location in an enhanced image to half of a maximum possible intensity value for the medical retinal image $C_{mid}$ scaled by a ratio of intensity at medical retinal image to intensity in the median filtered image as expressed by $$C_{mid} \cdot \frac{I(x, y)}{I_{Back,S}(x, y)};$$

and if the intensities at the first pixel location is not lower, then set a value at the first pixel location in the enhanced image to a sum of half a maximum possible intensity value for the medical retinal image, $C_{mid}$, and $(C_{mid}-1)$ scaled by a ratio of a difference of intensity of the median filtered image from intensity of the medical retinal original image to a difference of intensity of the median filtered image from a maximum possible intensity value $C_{max}$, expressed as $$C_{mid} + (C_{mid} - 1) \cdot \frac{I(x, y) - I_{Back,S}(x, y)}{C_{max} - I_{Back,S}(x, y)};$$

wherein the enhanced image is used to infer or further analyze, a medical condition of the subject.

In an additional embodiment, a computer-implemented method for enhancing a retinal image is disclosed. The method may include, as implemented by one or more computing devices configured with specific executable instructions, accessing a medial retinal image for enhancement, the medical retinal image related to a subject; computing a median filtered image $I_{Back,S}$ with a median computed over a geometric shape, at single or multiple scales; determining whether intensity at a first pixel location in the medical retinal image $I(x,y)$ is lower than intensity at a same position in the median filtered image $I_{Back,S}(x,y)$; if the intensities at the first pixel location is lower, then setting a value at the first pixel location in an enhanced image to half of a maximum possible intensity value for the medical retinal image $C_{mid}$ scaled by a ratio of intensity at medical retinal image to intensity in the median filtered image as expressed by $$C_{mid} \cdot \frac{I(x, y)}{I_{Back,S}(x, y)};$$

and it the intensities at the first pixel location is not lower, then setting a value at the first pixel location in the enhanced image to a sum of half a maximum possible intensity value for the medical retinal image, $C_{mid}$, and $(C_{mid}-1)$ scaled by a ratio of a difference of intensity of the median filtered image from intensity of the medical retinal original image to a difference of intensity of the median filtered image from a maximum possible intensity value $C_{max}$, expressed as $$C_{mid} + (C_{mid} - 1) \cdot \frac{I(x, y) - I_{Back,S}(x, y)}{C_{max} - I_{Back,S}(x, y)};$$

using the enhanced image to infer or further analyze, a medical condition of the subject.

In a further embodiment, non-transitory computer storage that stores executable program instructions is disclosed. The non-transitory computer storage may include instructions that, when executed by one or more computing devices, configure the one or more computing devices to perform operations including: accessing a medial retinal image for enhancement, the medical retinal image related to a subject; computing a median filtered image $I_{Back,S}$ with a median computed over a geometric shape, at single or multiple scales; determining whether intensity at a first pixel location in the medical retinal image I(x, y) is lower than intensity at a same position in the median filtered image $I_{Back,S}$ (x, y); if the intensities at the first pixel location is lower, then setting a value at the first pixel location in an enhanced image to half of a maximum possible intensity value for the medical retinal image $C_{mid}$ scaled by a ratio of intensity at medical retinal image to intensity in the median filtered image as expressed by $$C_{mid} \cdot \frac{I(x, y)}{I_{Back,S}(x, y)};$$

and if the intensities at the first pixel location is not lower, then setting a value at the first pixel location in the enhanced image to a sum of half a maximum possible intensity value for the medical retinal image, $C_{mid}$, and ($C_{mid}$−1) scaled by a ratio of a difference of intensity of the median filtered image from intensity of the medical retinal original image to a difference of intensity of the median filtered image from a maximum possible intensity value $C_{max}$, expressed $$C_{mid} + (C_{mid} - 1) \cdot \frac{I(x, y) - I_{Back,S}(x, y)}{C_{max} - I_{Back,S}(x, y)};$$

using the enhanced image to infer or further analyze, a medical condition of the subject.

In an additional embodiment, a computing system for automated detection of active pixels in retinal images is disclosed. The computing system may include one or more hardware computer processors; and one or more storage devices configured to store software instructions configured for execution by the one or more hardware computer processors in order to cause the computing system to: access a retinal image; generate a first median normalized image using the retinal image with a median computed over a first geometric shape of a first size; generate a second median normalized image using the retinal image with a median computed over the first geometric shape of a second size, the second size different from the first size; automatically generate a difference image by computing a difference between the first median normalized image and the second median normalized image; generate a binary image by computing a hysteresis threshold of the difference image using at least two thresholds to detect dark and bright structures in the difference image; apply a connected component analysis to the binary image to group neighboring pixels of the binary image into a plurality of local regions; compute the area of each local region in the plurality of local regions; and store the plurality of local regions in a memory of the computing system.

In a further embodiment, a computer-implemented method for automated detection of active pixels in retinal images is disclosed. The method may include, as implemented by one or more computing devices configured with specific executable instructions: accessing a retinal image; generating a first median normalized image using the retinal image with a median computed over a first geometric shape of a first size; generating a second median normalized image using the retinal image with a median computed over the first geometric shape of a second size, the second size different from the first size; automatically generating a difference image by computing a difference between the first median normalized image and the second median normalized image; generating a binary image by computing a hysteresis threshold of the difference image using at least two thresholds to detect dark and bright structures in the difference image; applying a connected component analysis to the binary image to group neighboring pixels of the binary image into a plurality of local regions; computing the area of each local region in the plurality of local regions; and storing the plurality of local regions in a memory.

In another embodiment, non-transitory computer storage that stores executable program instructions is disclosed. The non-transitory computer storage may include instructions that, when executed by one or more computing devices, configure the one or more computing devices to perform operations including: accessing a retinal image; generating a first median normalized image using the retinal image with a median computed over a first geometric shape of a first size; generating a second median normalized image using the retinal image with a median computed over the first geometric shape of a second size, the second size different from the first size; automatically generating a difference image by computing a difference between the first median normalized image and the second median normalized image; generating a binary image by computing a hysteresis threshold of the difference image using at least two thresholds to detect dark and bright structures in the difference image; applying a connected component analysis to the binary image to group neighboring pixels of the binary image into a plurality of local regions; computing the area of each local region in the plurality of local regions; and storing the plurality of local regions in a memory.

In an additional embodiment, a computing system for automated generation of descriptors of local regions within a retinal image is disclosed, the computing system may include one or more hardware computer processors; and one or more storage devices configured to store software instructions configured for execution by the one or more hardware computer processors in order to cause the computing system to: access a retinal image; generate a first morphological filtered image using the retinal image, with a the said morphological filter computed over a first geometric shape; generate a second morphological filtered image using the retinal image, with a morphological filter computed over a second geometric shape, the second geometric shape having one or more of a different shape or different size from the first geometric shape; generate a difference image by computing a difference between the first morphological filtered image and the second morphological filtered image; and assign the difference of image pixel values as a descriptor value, each descriptor value corresponding to given pixel location of the said retinal image.

In a further embodiment, a computer-implemented method for automated generation of descriptors of local regions within a retinal image is disclosed. The method may include, as implemented by one or more computing devices configured with specific executable instructions: accessing a retinal image; generating a first morphological filtered image using the retinal image, with a the said morphological filter computed over a first geometric shape; generating a second morphological filtered image using the retinal image, with a morphological filter computed over a second geometric shape, the second geometric shape having one or more of a different shape or different size from the first geometric shape; generating a difference image by computing a difference between the first morphological filtered image and the second morphological filtered image; and assigning the difference of image pixel values as a descriptor value, each descriptor value corresponding to given pixel location of the said retinal image.

In another embodiment, non-transitory computer storage that stores executable program instructions is disclosed. The non-transitory computer storage may include instructions that, when executed by one or more computing devices, configure the one or more computing devices to perform operations including: accessing a retinal image; generating a first morphological filtered image using the retinal image, with a the said morphological filter computed over a first geometric shape; generating a second morphological filtered image using the retinal image, with a morphological filter computed over a second geometric shape, the second geometric shape having one or more of a different shape or different size from the first geometric shape; generating a difference image by computing a difference between the first morphological filtered image and the second morphological filtered image; and assigning the difference of image pixel values as a descriptor value, each descriptor value corresponding to given pixel location of the said retinal image.

In an additional embodiment, a computing system for automated processing of retinal images for screening of diseases or abnormalities is disclosed. The computing system may include: one or more hardware computer processors; and one or more storage devices configured to store software instructions configured for execution by the one or more hardware computer processors in order to cause the computing system to: access retinal images related to a patient, each of the retinal images comprising a plurality of pixels; for each of the retinal images, designate a first set of the plurality of pixels as active pixels indicating that they include interesting regions of the retinal image, the designating using one or more of: conditional number theory, single- or multi-scale interest region detection, vasculature analysis, or structured-ness analysis; for each of the retinal images, compute descriptors from the retinal image, the descriptors including one or more of: morphological filterbank descriptors, median filterbank descriptors, oriented median filterbank descriptors, Hessian based descriptors, Gaussian derivatives descriptors, blob statistics descriptors, color descriptors, matched filter descriptors, path opening and closing based morphological descriptors, local binary pattern descriptors, local shape descriptors, local texture descriptors, local Fourier spectral descriptors, localized Gabor jets descriptors, edge flow descriptors, and edge descriptors such as difference of Gaussians, focus measure descriptors such as sum-modified Laplacian, saturation measure descriptors, contrast descriptors, or noise metric descriptors; and classify one or more of: a pixel in the plurality of pixels, an interesting region within the image, the entire retinal image, or a collection of retinal images, as normal or abnormal using supervised learning utilizing the computed descriptors, using one or more of: a support vector machine, support vector regression, k-nearest neighbor, naive Bayes, Fisher linear discriminant, neural network, deep learning, or convolution networks.

In a further embodiment, a computer implemented method for automated processing of retinal images for screening of diseases or abnormalities is disclosed. The method may include: accessing retinal images related to a patient, each of the retinal images comprising a plurality of pixels; for each of the retinal images, designating a first set of the plurality of pixels as active pixels indicating that they include interesting regions of the retinal image, the designating using one or more of: conditional number theory, single- or multi-scale interest region detection, vasculature analysis, or structured-ness analysis; for each of the retinal images, computing descriptors from the retinal image, the descriptors including one or more of: morphological filterbank descriptors, median filterbank descriptors, oriented median filterbank descriptors, Hessian based descriptors, Gaussian derivatives descriptors, blob statistics descriptors, color descriptors, matched filter descriptors, path opening and closing based morphological descriptors, local binary pattern descriptors, local shape descriptors, local texture descriptors, local Fourier spectral descriptors, localized Gabor jets descriptors, edge flow descriptors, and edge descriptors such as difference of Gaussians, focus measure descriptors such as sum-modified Laplacian, saturation measure descriptors, contrast descriptors, or noise metric descriptors; and classifying one or more of: a pixel in the plurality of pixels, an interesting region within the image, the entire retinal image, or a collection of retinal images, as normal or abnormal using supervised learning utilizing the computed descriptors, using one or more of: a support vector machine, support vector regression, k-nearest neighbor, naive Bayes, Fisher linear discriminant, neural network, deep learning, or convolution networks.

In another embodiment, non-transitory computer storage that stores executable program instructions is disclosed. The non-transitory computer storage may include instructions that, when executed by one or more computing devices, configure the one or more computing devices to perform operations including: accessing retinal images related to a patient, each of the retinal images comprising a plurality of pixels; for each of the retinal images, designating a first set of the plurality of pixels as active pixels indicating that they include interesting regions of the retinal image, the designating using one or more of: conditional number theory, single- or multi-scale interest region detection, vasculature analysis, or structured-ness analysis; for each of the retinal images, computing descriptors from the retinal image, the descriptors including one or more of: morphological filterbank descriptors, median filterbank descriptors, oriented median filterbank descriptors, Hessian based descriptors, Gaussian derivatives descriptors, blob statistics descriptors, color descriptors, matched filter descriptors, path opening and closing based morphological descriptors, local binary pattern descriptors, local shape descriptors, local texture descriptors, local Fourier spectral descriptors, localized Gabor jets descriptors, edge flow descriptors, and edge descriptors such as difference of Gaussians, focus measure descriptors such as sum-modified Laplacian, saturation measure descriptors, contrast descriptors, or noise metric descriptors; and classifying one or more of: a pixel in the plurality of pixels, an interesting region within the image, the entire retinal image, or a collection of retinal images, as normal or abnormal using supervised learning utilizing the computed descriptors, using one or more of: a support vector machine, support vector regression, k-nearest neighbor, naive Bayes, Fisher linear discriminant, neural network, deep learning, or convolution networks.

In an additional embodiment, a computing system for automated computation of image-based lesion biomarkers for disease analysis is disclosed. The computing system may include: one or more hardware computer processors; and one or more storage devices configured to store software instructions configured for execution by the one or more hardware computer processors in order to cause the computing system to: access a first set of retinal images related to one or more visits from a patient, each of the retinal images in the first set comprising a plurality of pixels; access a second set of retinal images related to a current visit from the patient, each of the retinal images in the second set comprising a plurality of pixels; perform lesion analysis comprising: detecting interesting pixels; computing descriptors from the images; and classifying active regions using machine learning techniques; conduct image-to-image registration of a second image from the second set and a first image from the first set using retinal image registration, the registration comprising: identifying pixels in the first image as landmarks; identifying pixels in the second image as landmarks; computing descriptors at landmark pixels; matching descriptors across the first image and the second image; and estimating a transformation model to align the first image and the second image; compute changes in lesions and anatomical structures in registered images; and quantify the changes in terms of statistics, wherein the computed statistics represent the image-based biomarker that can be used for one or more of: monitoring progression, early detection, or monitoring effectiveness of treatment or therapy.

In a further embodiment, a computer implemented method for automated computation of image-based lesion biomarkers for disease analysis is disclosed. The method may include: accessing a first set of retinal images related to one or more visits from a patient, each of the retinal images in the first set comprising a plurality of pixels; accessing a second set of retinal images related to a current visit from the patient, each of the retinal images in the second set comprising a plurality of pixels; performing lesion analysis comprising: detecting interesting pixels; computing descriptors from the images; and classifying active regions using machine learning techniques; conducting image-to-image registration of a second image from the second set and a first image from the first set using retinal image registration, the registration comprising: identifying pixels in the first image as landmarks; identifying pixels in the second image as landmarks; computing descriptors at landmark pixels; matching descriptors across the first image and the second image; and estimating a transformation model to align the first image and the second image; computing changes in lesions and anatomical structures in registered images; and quantifying the changes in terms of statistics, wherein the computed statistics represent the image-based biomarker that can be used for one or more of: monitoring progression, early detection, or monitoring effectiveness of treatment or therapy.

In another embodiment, non-transitory computer storage that stores executable program instructions is disclosed. The non-transitory computer storage may include instructions that, when executed by one or more computing devices, configure the one or more computing devices to perform operations including: accessing a first set of retinal images related to one or more visits from a patient, each of the retinal images in the first set comprising a plurality of pixels; accessing a second set of retinal images related to a current visit from the patient, each of the retinal images in the second set comprising a plurality of pixels; performing lesion analysis comprising: detecting interesting pixels; computing descriptors from the images; and classifying active regions using machine learning techniques; conducting image-to-image registration of a second image from the second set and a first image from the first set using retinal image registration, the registration comprising: identifying pixels in the first image as landmarks; identifying pixels in the second image as landmarks; computing descriptors at landmark pixels; matching descriptors across the first image and the second image; and estimating a transformation model to align the first image and the second image; computing changes in lesions and anatomical structures in registered images; and quantifying the changes in terms of statistics, wherein the computed statistics represent the image-based biomarker that can be used for one or more of: monitoring progression, early detection, or monitoring effectiveness of treatment or therapy.

In an additional embodiment, a computing system for identifying the quality of an image to infer its appropriateness for manual or automatic grading id disclosed. The computing system may include: one or more hardware computer processors; and one or more storage devices configured to store software instructions configured for execution by the one or more hardware computer processors in order to cause the computing system to: access a retinal image related to a subject; automatically compute descriptors from the retinal image, the descriptors comprising a vector of a plurality of values for capturing a particular quality of an image and including one or more of: focus measure descriptors, saturation measure descriptors, contrast descriptors, color descriptors, texture descriptors, or noise metric descriptors; and use the descriptors to classify image suitability for grading comprising one or more of: support vector machine, support vector regression, k-nearest neighbor, naive Bayes, Fisher linear discriminant, neural network, deep learning, or convolution networks.

In a further embodiment, a computer implemented method for identifying the quality of an image to infer its appropriateness for manual or automatic grading. The method may include: accessing a retinal image related to a subject; automatically computing descriptors from the retinal image, the descriptors comprising a vector of a plurality of values for capturing a particular quality of an image and including one or more of: focus measure descriptors, saturation measure descriptors, contrast descriptors, color descriptors, texture descriptors, or noise metric descriptors; and using the descriptors to classify image suitability for grading comprising one or more of: support vector machine, support vector regression, k-nearest neighbor, naive Bayes, Fisher linear discriminant, neural network, deep learning, or convolution networks.

In another embodiment, non-transitory computer storage that stores executable program instructions is disclosed. The non-transitory computer storage may include instructions that, when executed by one or more computing devices, configure the one or more computing devices to perform operations including: accessing a retinal image related to a subject; automatically computing descriptors from the retinal image, the descriptors comprising a vector of a plurality of values for capturing a particular quality of an image and including one or more of: focus measure descriptors, saturation measure descriptors, contrast descriptors, color descriptors, texture descriptors, or noise metric descriptors; and using the descriptors to classify image suitability for grading comprising one or more of: support vector machine, support vector regression, k-nearest neighbor, naive Bayes, Fisher linear discriminant, neural network, deep learning, or convolution networks.

In one embodiment of the system, a retinal fundus image is acquired from a patient, then active or interesting regions comprising active pixels from the image are determined using multi-scale background estimation. The inherent scale and orientation at which these active pixels are described is determined automatically. A local description of the pixels may be formed using one or more of median filterbank descriptors, shape descriptors, edge flow descriptors, spectral descriptors, mutual information, or local texture descriptors. One embodiment of the system provides a framework that allows computation of these descriptors at multiple scales. In addition, supervised learning and classification can be used to obtain a prediction for each pixel for each class of lesion or retinal anatomical structure, such as optic nerve head, veins, arteries, and/or fovea. A joint segmentation-recognition method can be used to recognize and localize the lesions and retinal structures. In one embodiment of the system, this lesion information is further processed to generate a prediction score indicating the severity of retinopathy in the patient, which provides context determining potential further operations such as clinical referral or recommendations for the next screening date. In another embodiment of the system, the automated detection of retinal image lesions is performed using images obtained from prior and current visits of the same patient. These images may be registered using the disclosed system. This registration allows for the alignment of images such that the anatomical structures overlap, and for the automated quantification of changes to the lesions. In addition, system may compute quantities including, but not limited to, appearance and disappearance rates of lesions (such as microaneurysms), and quantification of changes in number, area, perimeter, location, distance from fovea, or distance from optic nerve head. These quantities can be used as image-based biomarker for monitoring progression, early detection, or evaluating efficacy of treatment, among many other uses.

BRIEF DESCRIPTION OF THE DRAWINGS

FIGS. 4A and 4C show examples of embodiments of retinal images taken on two different retinal devices.

FIGS. 4B and 4D show examples of embodiments of median normalized images.

FIGS. 4E and 4F demonstrate an example of embodiments of improved lesion and vessel visibility after image enhancement.

FIGS. 5A and 5B show examples of embodiments of retinal images.

FIGS. 5C and 5D show examples of embodiments of a retinal fundus mask.

FIGS. 6A and 6B show an example of embodiments of before and after noise removal.

FIGS. 31A and 31B show patches of aligned image patches from two longitudinal images.

FIGS. 31C and 31D show persistent microaneurysms (MAs) along with the new and disappeared MAs.

FIG. 32A shows a patch of an image with MAs.

FIG. 32B shows ground truth annotations marking MAs.

FIG. 32C shows MAs detected by one embodiment with a confidence of the estimate depicted by the brightness of the disk.

FIG. 36C depicts an example of one embodiment of a user interface of a tool for screening for multiple encounters.

FIGS. 41A and 41B show embodiments of Cytomegalovirus retinitis screening results using one embodiment of the Cytomegalovirus retinitis detection module for "normal retina" category screened as "no refer".

FIGS. 41C and 41D show embodiments of Cytomegalovirus retinitis screening results using one embodiment of the Cytomegalovirus retinitis detection module for "retina with CMVR" category screened as "refer".

FIGS. 41E and 41F show embodiments of Cytomegalovirus retinitis screening results using one embodiment of the Cytomegalovirus retinitis detection module for "cannot determine" category screened as "refer".

DETAILED DESCRIPTION OF PREFERRED EMBODIMENTS

I. Rapid Increase in Retinal Disease

Figure 1:
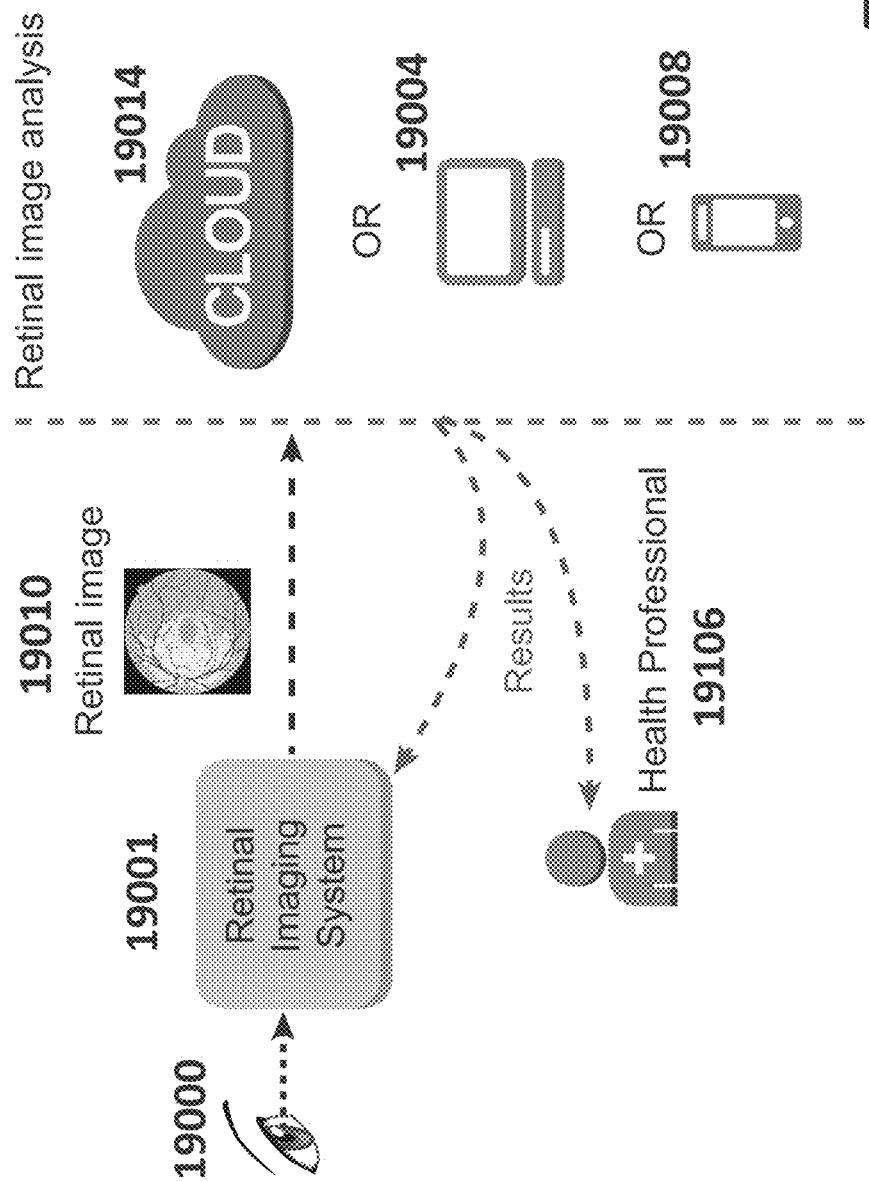
FIG. 1 shows one embodiment in which retinal image analysis can be applied.

Retinal diseases in humans can be manifestations of different physiological or pathological conditions such as diabetes that causes diabetic retinopathy, cytomegalovirus that causes retinitis in immune-system compromised patients with HIV/AIDS, intraocular pressure buildup that results in optic neuropathy leading to glaucoma, age-related degeneration of macula seen in seniors, and so forth. Of late, improved longevity and "stationary", stress-filled lifestyles have resulted in a rapid increase in the number of patients suffering from these vision threatening conditions. There is an urgent need for a large-scale improvement in the way in which these diseases are screened, diagnosed, and treated.

Diabetes mellitus (DM), in particular, is a chronic disease which impairs the body's ability to metabolize glucose. Diabetic retinopathy (DR) is a common microvascular complication of diabetes, in which damaged retinal blood vessels become leaky or occluded, leading to vision loss. Clinical trials have demonstrated that early detection and treatment of DR can reduce vision loss by 90%. Despite its preventable nature, DR is the leading cause of blindness in the adult working age population. Technologies that allow early screening of diabetic patients who are likely to progress rapidly would greatly help reduce the toll taken by this blinding eye disease. This is especially important because DR progresses without much pain or discomfort until the patient suffers actual vision loss, at which point it is often too late for effective treatment. Worldwide, 371 million people suffer from diabetes and this number is expected to grow to half a billion by 2030. The current clinical guideline is to recommend annual DR screening for everyone diagnosed with diabetes. However, the majority of diabetics do not get their annual screening, for many reasons, including lack of access to ophthalmology clinicians, lack of insurance, or lack of education. Even if the patients have knowledge and experience, the number of clinicians screening for DR is an order of magnitude less than that required to screen the current diabetic population. This is as true for first world countries, including America and Europe, as it is for the developing world. The exponentially growing need for DR screening can be met effectively by a computer-aided DR screening system, provided it is robust, scalable, and fast.

For effective DR screening of diabetics, telescreening programs are being implemented worldwide. These programs use fundus photography, using a fundus camera typically deployed at a primary care facility where the diabetic patients normally go for monitoring and treatment. Such telemedicine programs significantly help in expanding the DR screening, but are still limited by the need for human grading, of the fundus photographs, which is typically performed at a reading center.

II. High-Level Overview of an Automated Imaging System

Methods and systems are disclosed that provide automated image analysis allowing detection, screening, and/or monitoring of retinal abnormalities, including diabetic retinopathy, macular degeneration, glaucoma, retinopathy of prematurity, cytomegalovirus retinitis, and hypertensive retinopathy.

In some embodiments, the methods and systems can be used to conduct automated screening of patients with one or more retinal diseases. In one embodiment, this is accomplished by first identifying interesting regions in an image of a patient's eye for further analysis, followed by computation of a plurality of descriptors of interesting pixels identified within the image. In this embodiment, these descriptors are used for training a machine learning algorithm, such as support vector machine, deep learning, neural network, naive Bayes, and/or k-nearest neighbor. In one embodiment, these classification methods are used to generate decision statistics for each pixel, and histograms for these pixel-level decision statistics are used to train another classifier, such as one of those mentioned above, to allow screening of one or more images of the patient's eye. In one embodiment, a dictionary of descriptor sets are formed using a clustering method, such as k-means, and this dictionary is used to form a histogram of codewords for an image. In one embodiment, the histogram descriptors are combined with the decision statistics histogram descriptors before training image-level, eye-level, and/or encounter-level classifiers. In one embodiment, multiple classifiers are each trained for specific lesion types and/or for different diseases. A score for a particular element can be generated by computing the distance of the given element from the classification boundary. In one embodiment, the screening system is further included in a telemedicine system, and the screening score is presented to a user of the telemedicine system.

The methods and systems can also be used to conduct automated identification and localization of lesions related to retinal diseases, including but not limited to diabetic retinopathy, macular degeneration, retinopathy of prematurity, or cytomegalovirus retinitis.

The methods and systems can also be used to compute biomarkers for retinal diseases based on images taken at different time intervals, for example, approximately once every year or about six months. In one embodiment, the images of a patient's eye from different visits are co-registered. The use of a lesion localization module allows for the detection of lesions as well as a quantification of changes in the patient's lesions over time, which is used as an image-based biomarker.

The methods and systems can also be used to conduct co-registration of retinal images. In one embodiment, these images could be of different fields of the eye, and in another embodiment these images could have been taken at different times.

The methods and systems can also be used to enhance images to make it easier to visualize the lesions by a human observer or for analysis by an automated image analysis system.

FIG. 1 shows one embodiment in which retinal image analysis is applied. In this embodiment, the patient 19000 is imaged using a retinal imaging system 19001. The image/images 19010 captured are sent for processing on a computing cloud 19014, a computer or computing system 19004, or a mobile device 19008. The results of the analysis are sent back to the health professional 19106 and/or to the retinal imaging system 19001.

The systems and methods disclosed herein include an automated screening system that processes automated image analysis algorithms that can automatically evaluate fundus photographs to triage patients with signs of diabetic retinopathy (DR) and other eye diseases. An automated telescreening system can assist an at-risk population by helping reduce the backlog in one or more of the following ways.

Seamlessly connecting primary care facilities with image reading centers, so that an expert is not needed at the point of care;

Re-prioritizing expert appointments, so patients at greater risk can be seen immediately by ophthalmologists;

Allowing primary care physicians and optometrists to use the tools to make informed decisions regarding disease care; or Improving patient awareness through visualization tools based on lesion detection and localization.

For example, to screen an estimated 371 million diabetics worldwide, and to scale the screening operation as the diabetic population grows to over half a billion by 2030, one embodiment of the automated screening system can be deployed at massive scales. At these numbers, it is recognized that automation is not simply a cost-cutting measure to save the time spent by the ophthalmologists, but rather it is the only realistic way to screen such large, growing, patient population.

The critical need for computerized retinal image screening has resulted in numerous academic and a few commercial efforts at addressing the problem of identifying and triaging patients with retinal diseases using automatic analysis of fundus photographs. For successful deployment, automated screening systems may include one or more of the following features:

i. High Sensitivity at a Reasonably High Specificity

For automated telescreening to gain acceptance among clinicians and administrators, the accuracy, sensitivity and specificity should be high enough to match trained human graders, though not necessarily retina experts. Studies suggest that sensitivity of 85%, with high enough specificity, is a good target but other sensitivity levels may be acceptable.

ii. Invariance to the Training Data

Many prior approaches work by using algorithms that learn, directly or indirectly, from a set of examples of already graded fundus images. This training data could have a key influence on the sensitivity and specificity of the algorithm. An algorithm whose behavior varies significantly between datasets is not preferred in some embodiments. Instead, in some embodiments, the computerized screening algorithm performs well on cross-dataset testing, that is, the algorithm generalizes well, when trained on one dataset and tested on another. Hence, what is sometimes desired is a system that can generalize in a robust fashion, performing well in a cross-dataset testing scenario.

iii. Robustness Against Varying Conditions

In a deployed setup, an algorithm does not have control over the make or model of the camera, the illumination, the skill-level of the technician, or the size of the patient's pupil. Hence, in some embodiments, a computerized retinal disease screening system is configured to work in varying imaging conditions.

iv. Scalability to Massive Screening Setups:

In some embodiments, a screening system processes and grades large, growing databases of patient images. The speed at which the algorithm performs grading can be important. In addition, testing time for a new image to be screened remains constant even as the database grows, such that it does not take longer to screen a new test image as the database size increases as more patients are screened. What is sometimes desired is a method that takes a constant time to evaluate a new set of patient images even as the database size grows.

v. Interoperability with Existing Systems and Software:

In some embodiments, the system does not disrupt the existing workflow that users are currently used to. This means that the system inter-operates with a variety of existing software. What is sometimes desired is a system that can be flexibly incorporated into existing software and devices.

Customized methods for low-level description of medical image characteristics that can lead to accuracy improvement is another potential feature. Furthermore, approaches that leverage information such as local scale and orientation within local image regions in medical images, leading to greater accuracy in lesion detection could also provide many benefits.

In addition, the availability of an effective biomarker, a measurable quantity that correlates with the clinical progression of the disease and greatly enhances the clinical care available to the patients. It could also positively impact drug research, facilitating early and reliable determination of biological efficacy of potential new therapies. It will be a greatly added benefit if the biomarker is based only on images, which would lead to non-invasive and inexpensive techniques. Because retinal vascular changes often reflect or mimic changes in other end organs, such as the kidney or the heart, the biomarker may also prove to be a valuable assay of the overall systemic vascular state of a patient with diabetes.

Lesion dynamics, such as microaneurysm (MA) turnover, have received less attention from academia or industry. Thus, a system that improves the lesion detection and localization accuracy could be beneficial. Furthermore, a system and method for computation of changes in retinal image lesions over successive visits would also be of value by leading to a variety of image-based biomarkers that could help monitor the progression of diseases.

Certain aspects, advantages, and novel features of the systems and methods have been and are described herein. It is to be understood that not necessarily all such advantages or features may be achieved in accordance with any particular embodiment. Thus, for example, those skilled in the art will recognize that the systems and methods may be embodied or carried out in a manner that achieves one advantage/feature or group of advantages/features as taught herein without necessarily achieving other advantages/features as may be taught or suggested herein.

III. Automated Low-Level Image Processing

In some embodiments, the systems and methods provide for various features of automated low-level image processing, which may include image enhancement or image-level processing blocks.

A. Image Enhancement

In some embodiments, the system may also make it easier for a human or an automated system to evaluate a retinal image and to visualize and quantify retinal abnormalities. Retinal fundus images can be acquired from a wide variety of cameras, under varying amounts of illumination, by different technicians, and on different people. From an image processing point of view, these images have different colors levels, different dynamic ranges, and different sensor noise levels. This makes it difficult for a system to operate on these images using the same parameters. Human image graders or experts may also find it a hindrance that the images often look very different overall. Therefore, in some embodiments, the image enhancement process applies filters on the images to enhance them in such a way that their appearance is neutralized. After this image enhancement processing, the enhanced images can be processed by the same algorithms using identical or substantially similar parameters.

Figure 2:
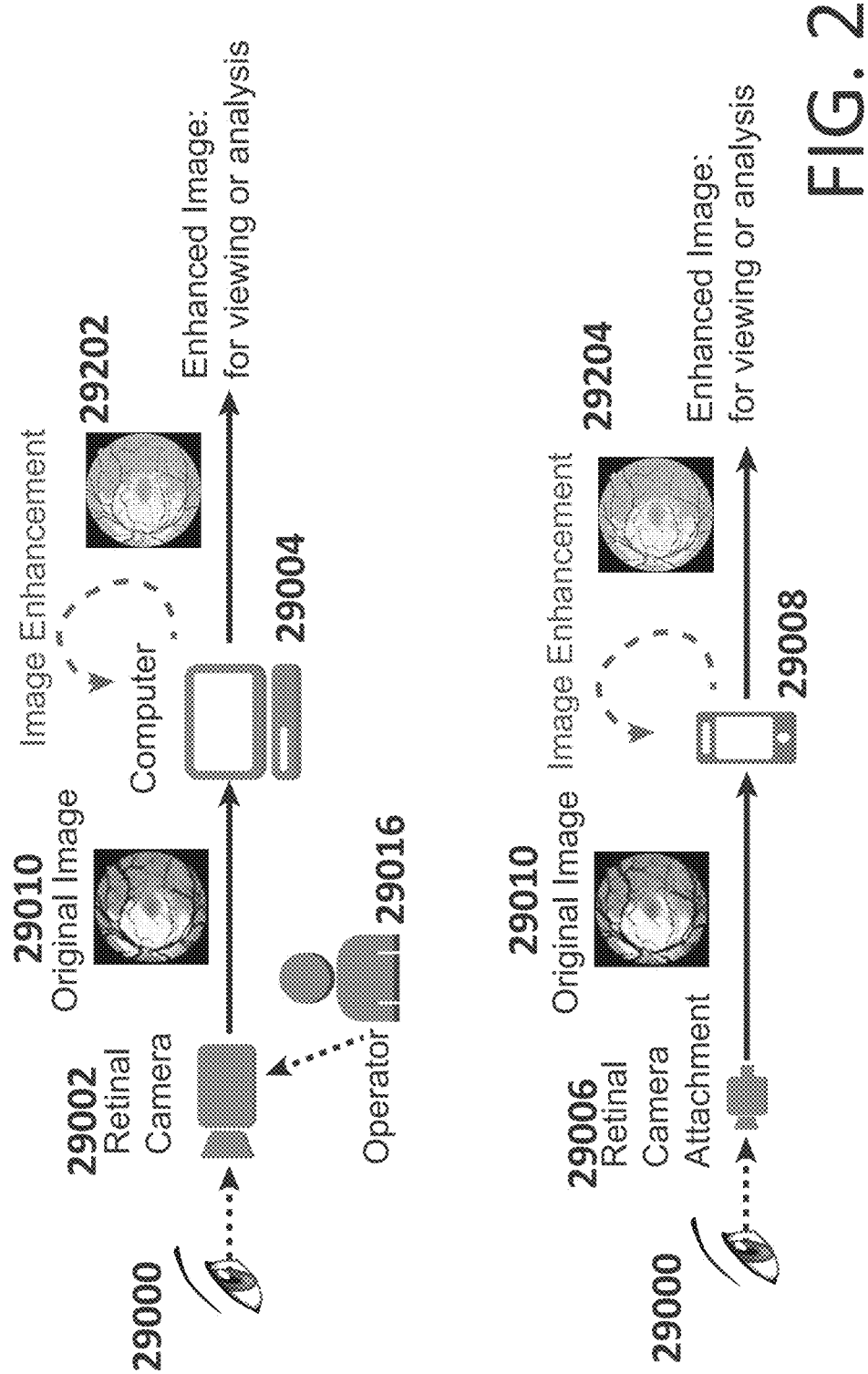
FIG. 2 illustrates various embodiments of an image enhancement system and process.

FIG. 2 shows one embodiment of a detailed view of the different scenarios in which image enhancement can be applied. In one scenario, the patient 29000 is imaged by an operator 29016 using an image capture device 29002. In this embodiment, the image capture device is depicted as a retinal camera. The images captured are sent to a computer or computing system 29004 for image enhancement. Enhanced images 29202 are then sent for viewing or further processing on the cloud 19014, or a computer or computing device 19004 or a mobile device 19008. In another embodiment, the images 29004 could directly be sent to the cloud 19014, the computer or computing device 19004, or the mobile device 19008 for enhancement and/or processing. In the second scenario, the patient 29000 may take the image himself using an image capture device 29006, which in this case is shown as a retinal camera attachment for a mobile device 29008. The image enhancement is then performed on the mobile device 29008. Enhanced images 29204 can then be sent for viewing or further processing.

Figure 3:
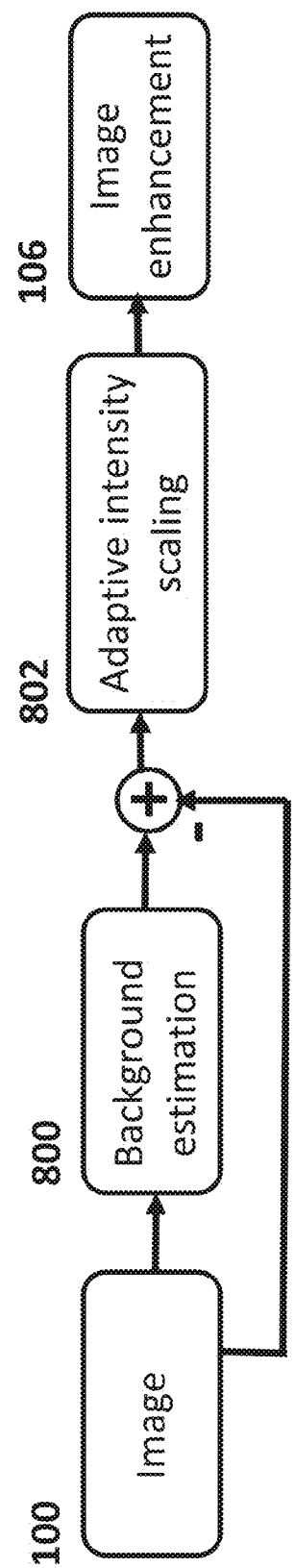
FIG. 3 is a block diagram of one embodiment for computing an enhanced image of an input retinal image.

FIG. 3 gives an overview of one embodiment of computing an enhanced image. The blocks shown here may be implemented in the cloud 19014, on a computer or computing system 19004, or a mobile device 19008, or the like. The image 100 refers in general to the retinal data, single or multidimensional, that has been captured using a retinal imaging device, such as camera for color image capture, fluorescein angiography (FA), adaptive optics, optical coherence tomography (OCT), hyperspectral imaging, scanning laser ophthalmoscope (SLO), wide-field imaging or ultra-wide-field imaging. Background estimation block 800 estimates the background of the image 100 at a given scale. Adaptive intensity scaling 802 is then applied to scale the image intensity based on local background intensity levels. Image enhancement module 106 enhances the image to normalize the effects of lighting, different cameras, retinal pigmentation and the like. An image is then created that excludes/ignores objects smaller than a given size.

In one embodiment, the images are first subjected to an edge-preserving bilateral filter such as the filter disclosed in Carlo Tomasi and Roberto Manduchi, "Bilateral Filtering for Gray and Color Images," in *Computer Vision, 1998. Sixth International Conference on*, 1998, 839-846; and Ben Weiss, "Fast Median and Bilateral Filtering," in *ACM Transactions on Graphics* (TOG), vol. 25, 2006, 519-526. The filter removes noise without affecting important landmarks such as lesions and vessels.

In one embodiment, the system then uses a median filter based normalization technique, referred to as median normalization, to locally enhance the image at each pixel using local background estimation. In some embodiments, the median normalized image intensity $I_{Norm,\mathcal{S}}$ at pixel location (x, y) is computed as, $$I_{Norm,S}(x,y) = \begin{cases} C_{mid} + (C_{mid} - 1) \cdot \frac{I(x,y) - I_{Back,S}(x,y)}{C_{max} - I_{Back,S}(x,y)} & \text{if } I(x,y) \geq I_{Back,S}(x,y), \\ C_{mid} \cdot \frac{I(x,y)}{I_{Back,S}(x,y)} & \text{otherwise} \end{cases} \quad \text{Equation 1}$$

where I is the input image with pixel intensities in the range $[C_{min}, C_{max}]=[0, 2^B-1]$, B is the image bit-depth, $I_{Back,\mathcal{S}}$ is background image obtained using a median filter over the area $\mathcal{S}$, and $C_{mid}=2^{B-1}$ is the "middle" gray pixel intensity value in image I. For an 8-bit image, $[C_{min}, C_{max}]=[0,255]$, and $C_{mid}=128$. In one embodiment, $\mathcal{S}$ is chosen to be a circle of radius r=100.

FIGS. 4B and 4D show embodiments of some example median normalized images for the input images shown in FIG. 4A and FIG. 4C respectively. Note that this normalization improves the visibility of structures such as lesions and vessels in the image as shown in FIG. 4E and FIG. 4F. The inset in FIGS. 4E and 4F show the improved visibility of microaneurysm lesions. The results of this image enhancement algorithm have also been qualitatively reviewed by retina experts at Doheny Eye Institute, and they concur with the observations noted here. The effectiveness of this algorithm is demonstrated by superior cross-dataset performance of the system described below in the section entitled "Screening Using Lesion Classifiers Trained On Another Dataset (Cross-Dataset Testing)."

B. Image-Level Processing

1. Image-Level Fundus Mask Generation

Typically, retinal fundus photographs have a central circular region of the eye visible, with a dark border surrounding it. Sometimes information pertaining to the patient, or the field number may also be embedded in the corners of the photograph. For retinal image analysis, these border regions of the photograph do not provide any useful information and therefore it is desirable to ignore them. In one embodiment, border regions of the retinal photographs are automatically identified using morphological filtering operations as described below.

In one embodiment, the input image is first blurred using a median filter. A binary mask is then generated by thresholding this image so that locations with pixel intensity values above a certain threshold are set to 1 in the mask, while other areas are set to 0. The threshold is empirically chosen so as to nullify the pixel intensity variations in the border regions, so that they go to 0 during thresholding. In one embodiment, this threshold is automatically estimated. The binary mask is then subjected to region dilation and erosion morphological operations, to obtain the final mask. In one embodiment, the median filter uses a radius of 5 pixels, and, the threshold for binary mask generation is 15 for an 8-bit image with pixel values ranging from [0,255], though other radii and thresholds can be used. The dilation and erosion operations can be performed using rectangular structuring elements, such as, for example, size 10 and 20 pixels respectively. FIG. 5A and FIG. 5B show two different retinal image types, and FIG. 5C and FIG. 5D show of fundus masks for these two images generated using the above described embodiment.

2. Optic Nerve Head Detection

In some embodiments, it may be beneficial to detect the optic nerve heard (ONH) within a retinal image. A ONH can be robustly detected using an approach that mirrors the one for lesions as described in section below entitled "Lesion Localization". In another embodiment, multi-resolution decomposition and template matching is employed for ONH localization.

In one embodiment, the ONH localization is performed on a full resolution retinal fundus image, or a resized version of the image, or the image (full or resized) processed using one or more morphological filters that can be chosen from minimum filter or maximum filter, dilation filter, morphological wavelet filter, or the like. An approximate location of the ONH is first estimated in the horizontal direction by filtering horizontal strips of the image whose height is equal to the typical ONH diameter and width is equal to the image width, with a filter kernel of size approximately equal to the typical ONH size. The filter kernel can be: a circle of specific radius, square of specific side and orientation, Gaussian of specific sigmas (that is, standard deviations), ellipse of specific orientation and axes, rectangle of specific orientation and sides, or a regular polygon of specific side. The filtered image strips are converted to a one-dimensional signal by collating the data along the vertical dimension by averaging or taking the maximum or minimum or the like. The largest N local maxima of the one-dimensional signal whose spatial locations are considerably apart are considered as likely horizontal locations of the ONH since the ONH is expected to be a bright region. In a similar fashion, the vertical position of the ONH is approximated by examining vertical image strips centered about the N approximate horizontal positions. This ONH position approximation technique produces M approximate locations for the ONH.

In one embodiment, the approximate sizes or radii of the possible ONHs can be estimated by using a segmentation algorithm such as the marker-controlled watershed algorithm. In one embodiment the markers are placed based on the knowledge of the fundus mask and approximate ONH location. In another embodiment, typical ONH sizes or radii can also be used as approximate ONH sizes or radii.

In one embodiment, these approximate locations and sizes for the ONH can be refined by performing template matching in a neighborhood about these approximate ONH locations and choosing the one location and size that gives the maximum confidence or probability of ONH presence.

In another embodiment, the ONH position can be estimated as the vertex of the parabola approximation to the major vascular arch.

3. Image Size Standardization

Different retinal fundus cameras capture images at varying resolutions and field of view. In order to process these different resolution images using the other blocks, in one embodiment the images are standardized by scaling them to have identical or near identical pixel pitch. The pixel pitch is computed using the resolution of the image and field of view information from the metadata. In one embodiment, if a field of view information is absent, then the pixel pitch is estimated by measuring the optic nerve head (ONH) size in the image as described in the section above entitled "Optic Nerve Head Detection." In one embodiment, an average ONH size of 2 mm can be used. The image at the end of size standardization is referred to as $I^{so}$. The fundus mask is generated for $I^{so}$ and can be used for further processing. In another embodiment, the diameter of the fundus mask is used as a standard quantity for the pitch. The diameter may be calculated as described in the section above entitled "Image-Level Fundus Mask Generation" or in the section below entitled "Encounter-Level Fundus Mask Generation."

4. Noise Removal

Fundus images usually have visible sensor noise that can potentially hamper lesion localization or detection. In order to reduce the effect of noise while preserving lesion and vessel structures, in one embodiment a bilateral filter may be used, such as, for example, the filter disclosed in Tomasi and Manduchi, "Bilateral Filtering for Gray and Color Images", and Weiss, "Fast Median and Bilateral Filtering." Bilateral filtering is a normalized convolution operation in which the weighting for each pixel p is determined by the spatial distance from the center pixel s, as well as its relative difference in intensity. In one embodiment, for input image I, output image J, and window Ω, the bilateral filtering operation is defined as follows:

$$J_s = \sum_{p \in \Omega} f(p-s)g(I_p - I_s)I_p \bigg/ \sum_{p \in \Omega} f(p-s)g(I_p - I_s)$$

where f and g are the spatial and intensity weighting functions respectively, which are typically Gaussian. In one embodiment, the parameters of the bilateral filter have been chosen to induce the smoothing effect so as not to miss small lesions such as microaneurysms. FIG. 6A shows one embodiment of an enlarged portion of a retinal image before noise removal and FIG. 6B shows one embodiment of the same portion after noise removal. It can be observed that the sensor noise is greatly suppressed while preserving lesion and vessel structures.

C. Encounter-Level Processing

While capturing images using commercial cameras, retinal cameras, or medical imaging equipment, several images could be captured in a short duration of time without changing the imaging hardware. These images will have certain similar characteristics that can be utilized for various tasks, such as image segmentation, detection, or analysis. However, the images possibly may have different fields of view or illumination conditions.

In particular, medical or retinal images captured during a patient visit are often captured using the same imaging set-up. The set of these images is termed an "encounter" of that patient on that date. For the specific case of retinal images, data from multiple images in an encounter can be used to produce fundus segmentation masks and detect image artifacts due to dust or blemishes as described in the sections that follow.

1. Encounter-Level Fundus Mask Generation

Many medical images such as those acquired using ultrasound equipment and those of the retina have useful information only in a portion of the rectangular image. In particular, most retinal fundus photographs have a central circle-like region of the eye visible, with the remainder of the photograph being dark. Information pertaining to the patient or the field number may be embedded in the regions of the photograph that do not contain useful image information. Therefore, before analysis of such photographs, it is desirable to identify regions of the photographs with useful image information using computer-aided processes and algorithms. One benefit of such identification is that it reduces the chances of false positives in the border regions. Additionally, this identification can reduce the analysis complexity and time for these images since a subset of pixels in the photographs is to be processed and analyzed.

Figure 7A:
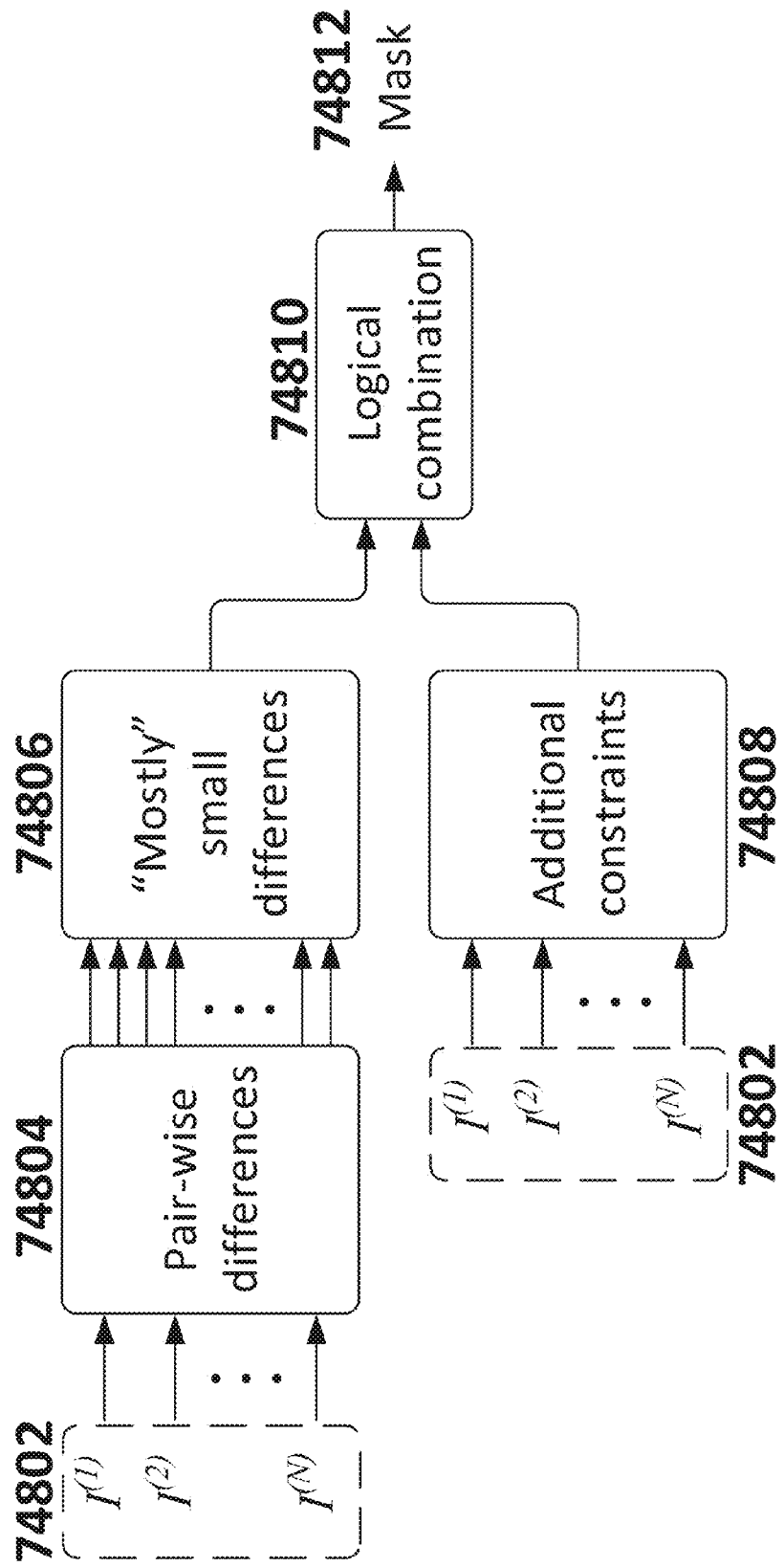
FIG. 7A is a block diagram of one embodiment of a system for identifying image regions with similar properties across multiple images.

FIG. 7A depicts one embodiment of an algorithmic framework to determine regions without useful image information from images captured during an encounter. The illustrated blocks may be implemented on the cloud 19014, a computer or computing device 19004, a mobile device 19008, the like as shown in FIG. 1. This analysis may be helpful when regions with useful information are sufficiently different across the images in an encounter compared to the outside regions without useful information. The N images 74802 in the encounter are denoted as $I^{(1)}, I^{(2)} \ldots I^{(N)}$. The regions that are similar across the images in the encounter are determined as those pixel positions where most of the pair-wise differences 74804 are small in magnitude 74806. The regions that are similar across most of the N images in the encounter include regions without useful image information. However, these regions also include portions of the region with useful image information that are also similar across most of the images in the encounter. Therefore, to exclude such similar regions with useful information, additional constraints 74808 can be included and logically combined 74810 with the regions determined to be similar and obtain the fundus mask 74812. For example, regions outside the fundus portion of retinal images usually have low pixel intensities and can be used to determine which region to exclude.

Figure 7B:
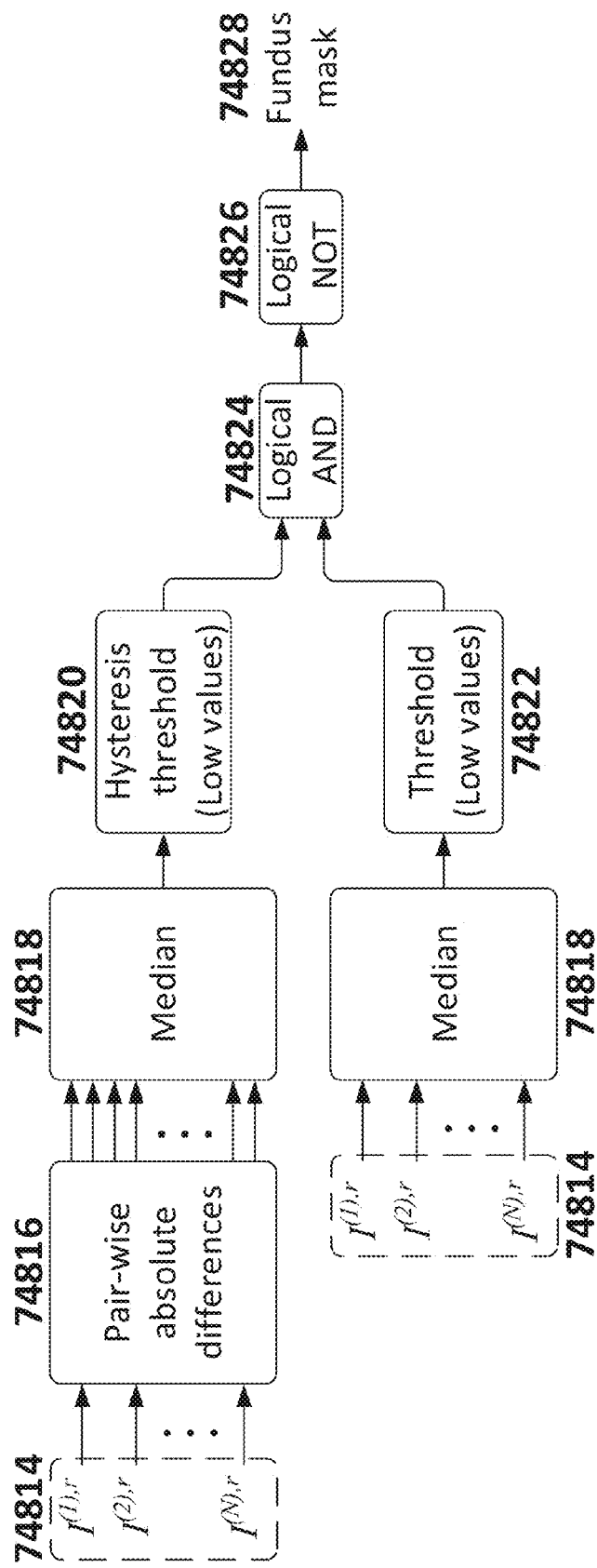
FIG. 7B is a block diagram of one embodiment of a system for identifying an encounter level fundus mask.

FIG. 7B depicts one embodiment of an algorithmic framework that determines a fundus mask for the retinal images in an encounter. In one embodiment, the encounter-level fundus mask generation may be simplified, with low loss in performance by using only the red channel of the retinal photographs denoted as $I^{(1),r}, I^{(2),r} \ldots I^{(N),r}$ 74814. This is because in most retinal photographs, the red channel has very high pixel values within the fundus region and small pixel values outside the fundus region. The noise may be removed from the red channels of the images in an encounter as described in the section above entitled "Noise Removal". Then, the absolute differences between possible pairs of images in the encounter are computed 74816 and the median across the absolute difference images is evaluated 74818. Pixels at a given spatial position in the images of an encounter are declared to be outside the fundus if the median of the absolute difference images 74818 at that position is low (for example, close to zero), 74820, and 74824 if the median of those pixel values is also small 74822. The fundus mask 74828 is obtained by logically negating 74826 the mask indicating regions outside the fundus.

Figure 8:
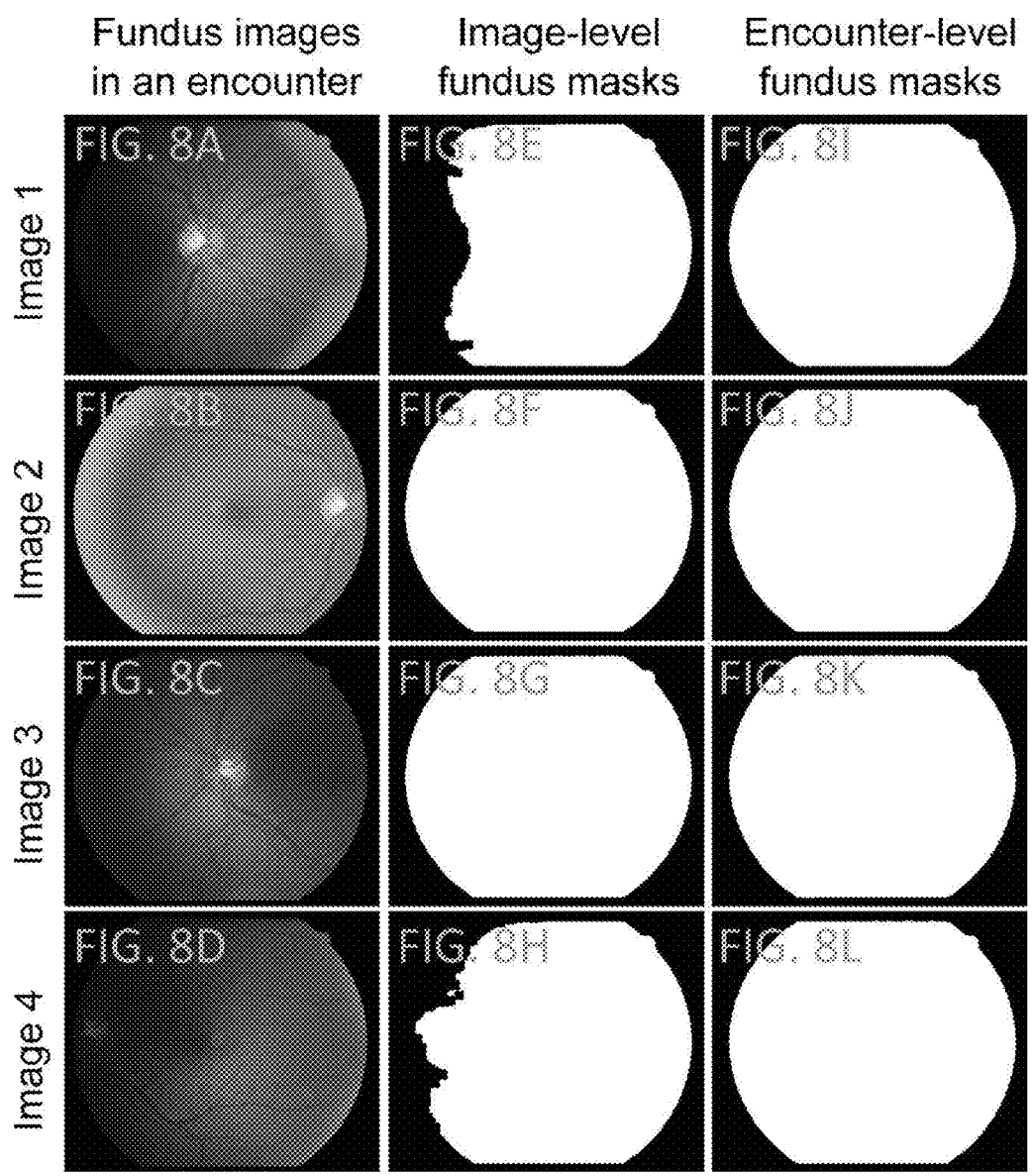
FIGS. 8A, 8B, 8C, and 8D show examples of embodiments of retinal images from a single patient encounter.
FIGS. 8E, 8F, 8G, and 8H show examples of embodiments of a retinal image-level fundus mask.
FIGS. 8I, 8J, 8K, and 8L show examples of embodiments of a retinal encounter-level fundus mask.

In particular, for retinal images, prior techniques to determine fundus masks include processing one retinal image at a time, which are based on thresholding the pixel intensities in the retinal image. Although these image-level fundus mask generation algorithms may be accurate for some retinal fundus photographs, they could fail for photographs that have dark fundus regions, such as those shown in FIG. 8. The failure of the image-level fundus mask generation algorithm as in FIG. 8E and FIG. 8H is primarily due to the pixel intensity thresholding operation that discards dark regions that have low pixel intensities in the images shown in FIG. 8A and FIG. 8D.

The drawbacks of image-level fundus mask generation can be overcome by computing a fundus mask using multiple images in an encounter, that is a given visit of a given patient. For example, three or more images in an encounter may be used if the images in the encounter have been captured using the same imaging hardware and settings and hence have the same fundus mask. Therefore, the encounter-level fundus mask computed using data from multiple images in an encounter will be more robust for low pixel intensities in the regions with useful image information.

Embodiments of encounter-level fundus masks generated using multiple images within an encounter are shown in FIGS. 8I, 8J, 8K, and 8L. It can be noted that in FIGS. 8A and 8D, pixels with low intensity values that are within the fundus regions are correctly identified by the encounter-level fundus mask shown in FIGS. 8I and 8L, unlike in the image-level fundus masks shown in FIGS. 8E and 8H.

In one embodiment, the fundus mask generation algorithm validates that the images in an encounter share the same fundus mask by computing the image-level fundus masks and ensuring that the two masks obtained differ in less than, for example, 10% of the total number of pixels in each image by logically "AND"-ing and "OR"-ing the individual image-level fundus masks. If the assumption is not validated, the image-level fundus masks are used and the encounter-level fundus masks are not calculated. Median values of absolute differences that are close to zero can be identified by hysteresis thresholding, for example by using techniques disclosed in John Canny, "A Computational Approach to Edge Detection," *Pattern Analysis and Machine Intelligence, IEEE Transactions on* no. 6 (1986): 679-698. In one embodiment, the upper threshold is set to −2, and the lower threshold is set to −3, such that medians of the pixel values are determined to be small if they are less than 15, the same value used for thresholding pixel values during image-level fundus mask generation.

2. Lens Or Sensor Dust And Blemish Artifact Detection

Dust and blemishes in the lens or sensor of an imaging device manifest as artifacts in the images captured using that device. In medical images, these dust and blemish artifacts can be mistaken to be pathological manifestations. In particular, in retinal images, the dust and blemish artifacts can be mistaken for lesions by both human readers and image analysis algorithms. However, detecting these artifacts using individual images is difficult since the artifacts might be indistinguishable from other structures in the image. Moreover, since images in an encounter are often captured using the same imaging device and settings, the blemish artifacts in these images will be co-located and similar looking. Therefore, it can be beneficial to detect the dust and blemish artifacts using multiple images within an encounter. Image artifacts due to dust and blemishes on the lens or in the sensor are termed as lens dust artifacts for simplicity and brevity, since they can be detected using similar techniques within the framework described below.

Figure 9A:
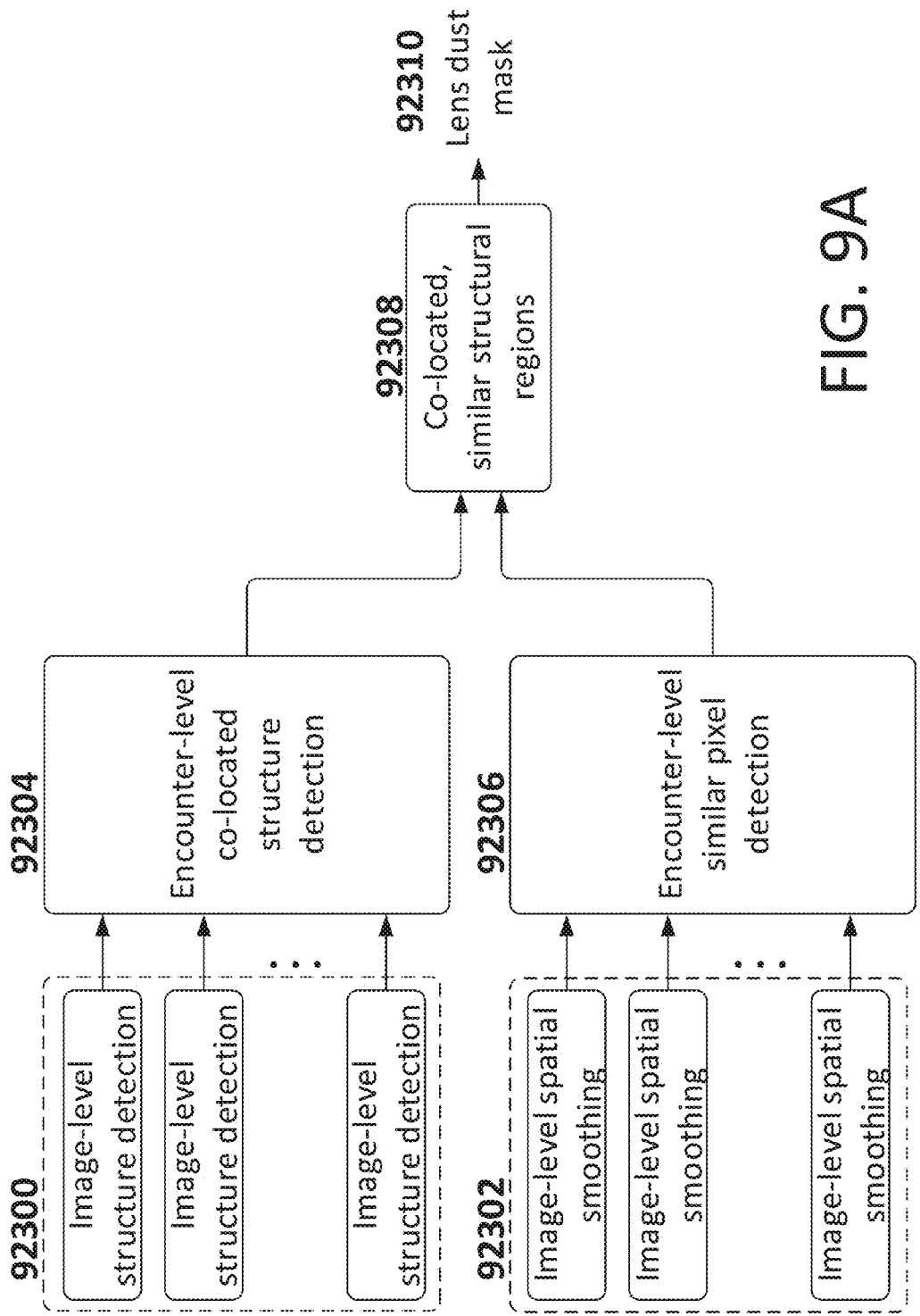
FIG. 9A depicts one embodiment of a process for lens dust artifact detection.

FIG. 9A depicts one embodiment of a process for lens dust artifact detection. The blocks for lens dust artifact detection may be implemented on the cloud 19014, or a computer or computing device 19004, a mobile device 19008, or the like, as shown in FIG. 1. The individual images are first processed 92300 to detect structures that could possibly be lens dust artifacts. Detected structures that are co-located across many of the images in the encounter are retained 92304, while the others are discarded. The images in the encounter are also independently smoothed 92302 and processed to determine pixel positions that are similar across many images in the encounter 92306. The lens dust mask 92310 indicates similar pixels that also correspond to co-located structures 92308 as possible locations for lens dust artifacts.

Additional information about embodiments of each of these blocks of the lens dust detection algorithm is discussed below. In one embodiment, lens dust detection is disabled if there are fewer than three images in the encounter, since in such a case, the lens dust artifacts detected may not be reliable. Moreover, the lens dust detection uses the red and blue channels of the photographs since vessels and other retinal structures are most visible in the green channel and can accidentally align in small regions and be misconstrued as lens dust artifacts. The lens dust artifacts are detected using multiple images in the encounter as described below and indicated by a binary lens dust mask which has true values at pixels most likely due to lens dust artifacts.

Figure 9B:
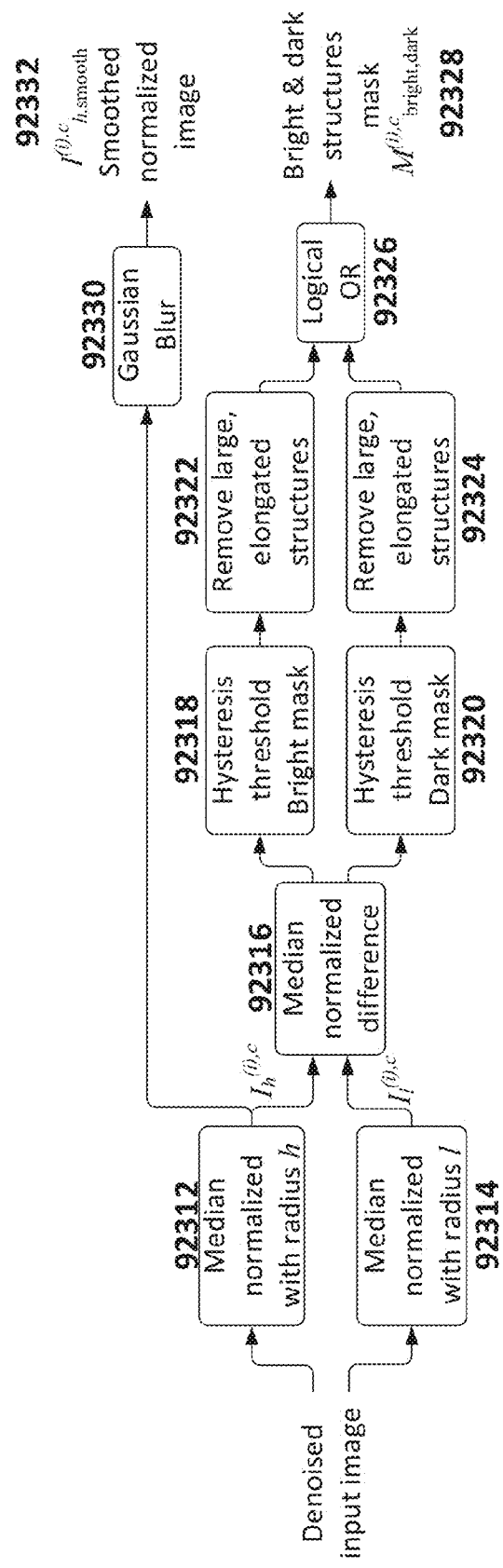
FIGS. 9B, 9C, 9D, and 9E are block diagrams of image processing operations used in an embodiment of lens dust artifact detection.

In one embodiment, noise may be removed from the images in the encounter using the algorithm described in the section above entitled "Noise Removal". These denoised images are denoted as $I^{(1)}, I^{(2)}, \ldots I^{(N)}$ where N is the total number of images in the encounter and the individual channels of the denoised images are denoted as $I^{(i),c}$ where c=r and b indicates which of the red or blue channels is being considered. If N≥3 and the image-level fundus masks are consistent, for example as determined by performing encounter-level fundus mask generation, the input images comprising the red and blue channels are individually normalized and/or enhanced using the processes described in the section above entitled "Image Enhancement." As shown in FIG. 9B, for each channel of each input image $I^{(i),c}$, two enhanced images are generated using different radii for the median filter: $I_h^{(i),c}$ with radius h 92312 and $I_l^{(i),c}$ with radius l 92314. The difference between the two enhanced images $I_{diff}^{(i),c} = (I_h^{(i),c} - I_l^{(i),c})$ is calculated 92316 and hysteresis thresholded using different thresholds 92318 and 92320 to detect dark and bright structures from which large and elongated structures are removed 92322 and 92324. The masks indicating the bright and dark structures are logically "OR"-ed 92326 to obtain the mask $M_{bright,dark}^{(i),c}$ 92328.

Figure 9C:
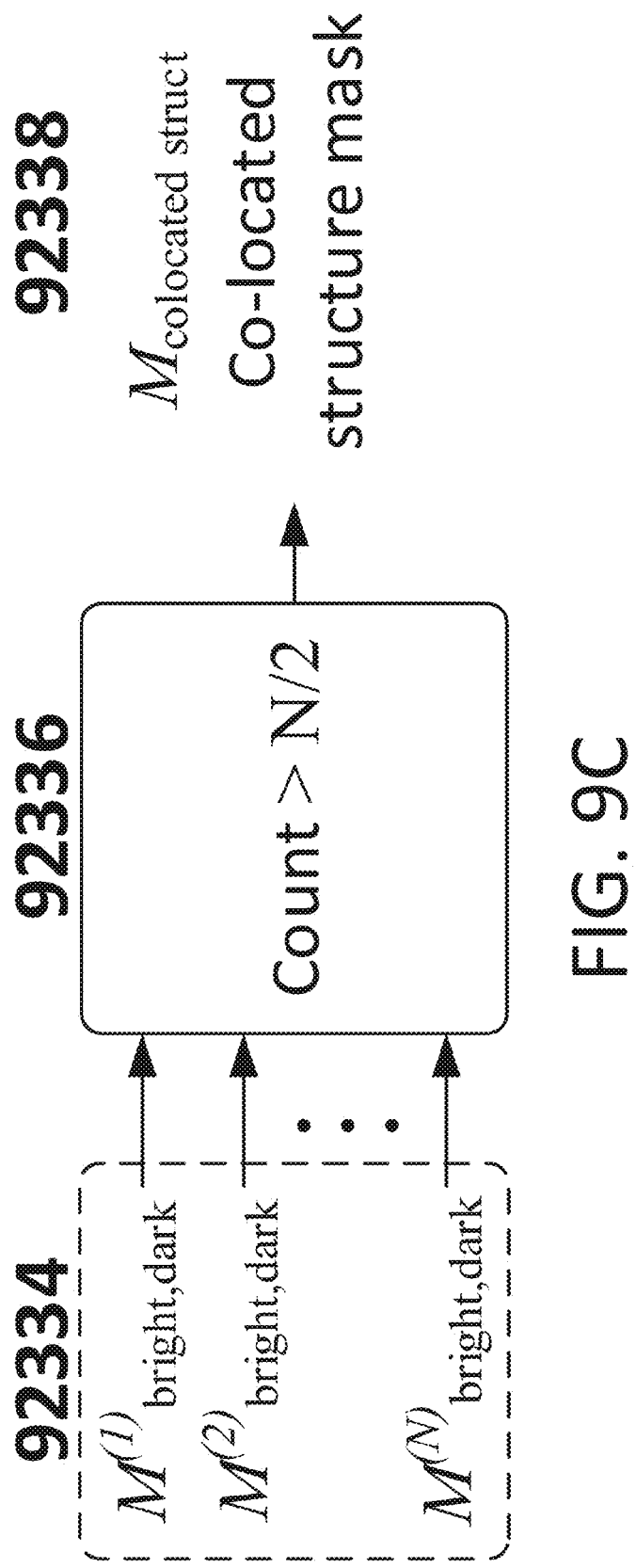

As shown in FIG. 9C, the mask $M_{bright,dark}^{(i),r}$ for the red channel and the mask $M_{bright,dark}^{(i),b}$ for the blue channel are further logically "OR"-ed to get a single mask $M_{Bright,dark}^{(i)}$ 92334 showing locations of bright and dark structures that are likely to be lens dust artifacts in the image $I^{(i)}$. If a spatial location is indicated as being part of a bright or dark structure in more than 50% of the images in the encounter 92336, it is likely that a lens dust artifact is present at that pixel location. This is indicated in a binary mask $M_{colocated\ struct}$ 92338.

Figure 9D:
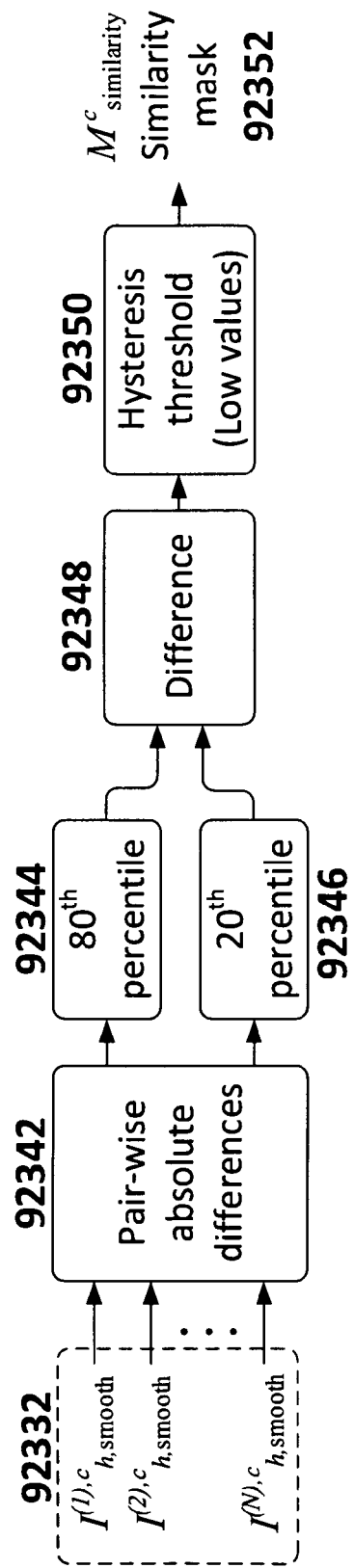

The normalized images $I_h^{(i),c}$, i=1,2, ..., N, c=r, b are processed using a Gaussian blurring filter 92330 to obtain smoothed versions $I_{h,smooth}^{(i),c}$ 92332 as shown in FIG. 9B. Then as shown in FIG. 9D, pair-wise absolute differences 92342 of these smoothed, normalized images are generated. In one embodiment, the difference 92348 between the 80th percentile a high percentile (for example, 92344) and 20th percentile a lower percentile (for example, 92346) of these absolute differences is computed as $I_{diff\ range}^c$ and hysteresis thresholded 92350 to obtain a mask $M_{similarity}^c$, c=r, b 92352 that indicates the spatial image locations where the images are similar within each of the red and blue channels.

Figure 9E:
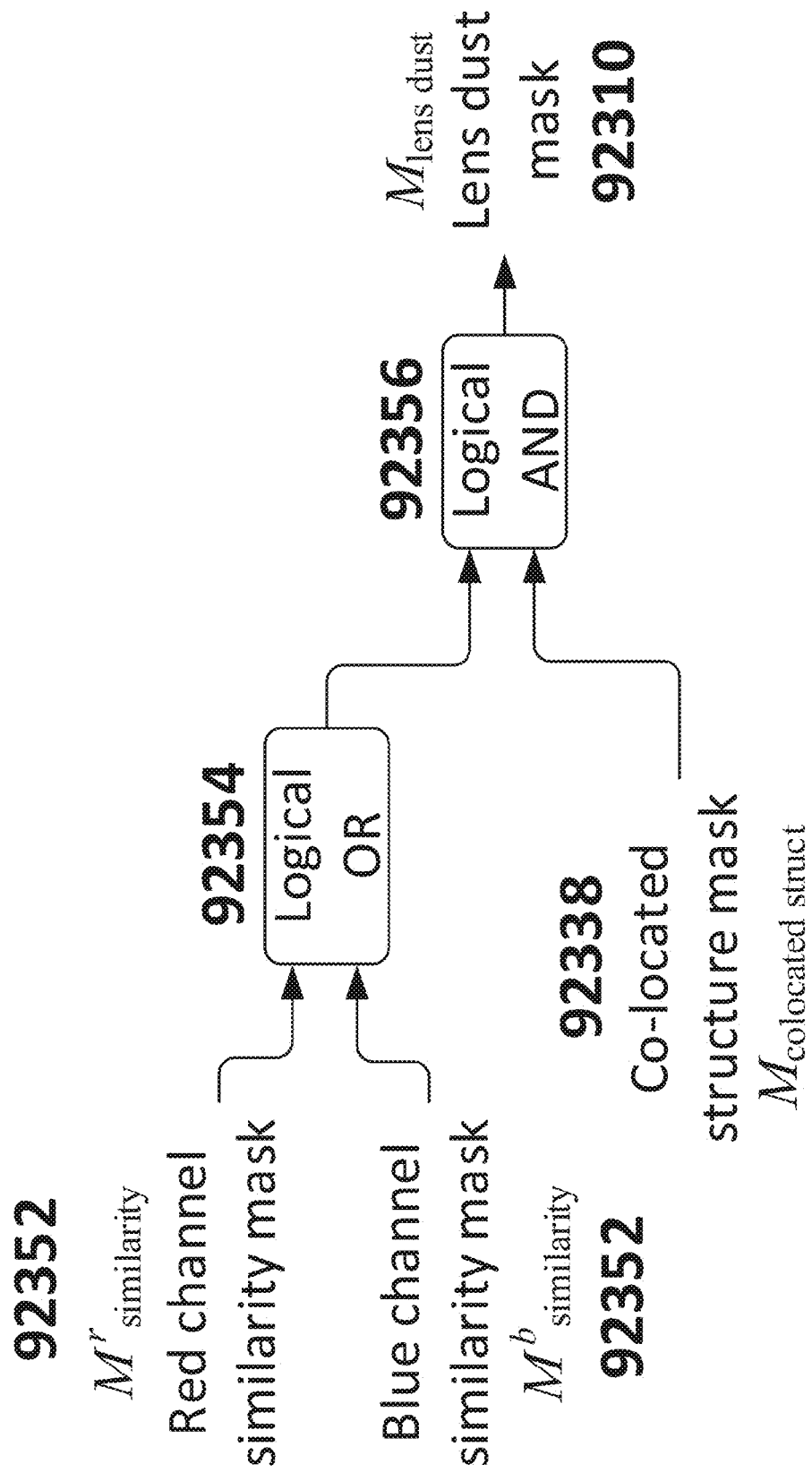

Finally as illustrated in FIG. 9E, the lens dust mask 92310 for the images in the encounter is obtained by logically "AND"-ing 92356 the mask $M_{colocated\ struct}$ 92338 indicating co-located structures and the logically "OR"-ed 92354 per-channel similarity masks $M_{similarity}^c$, c=r, b 92352.

Figure 10:
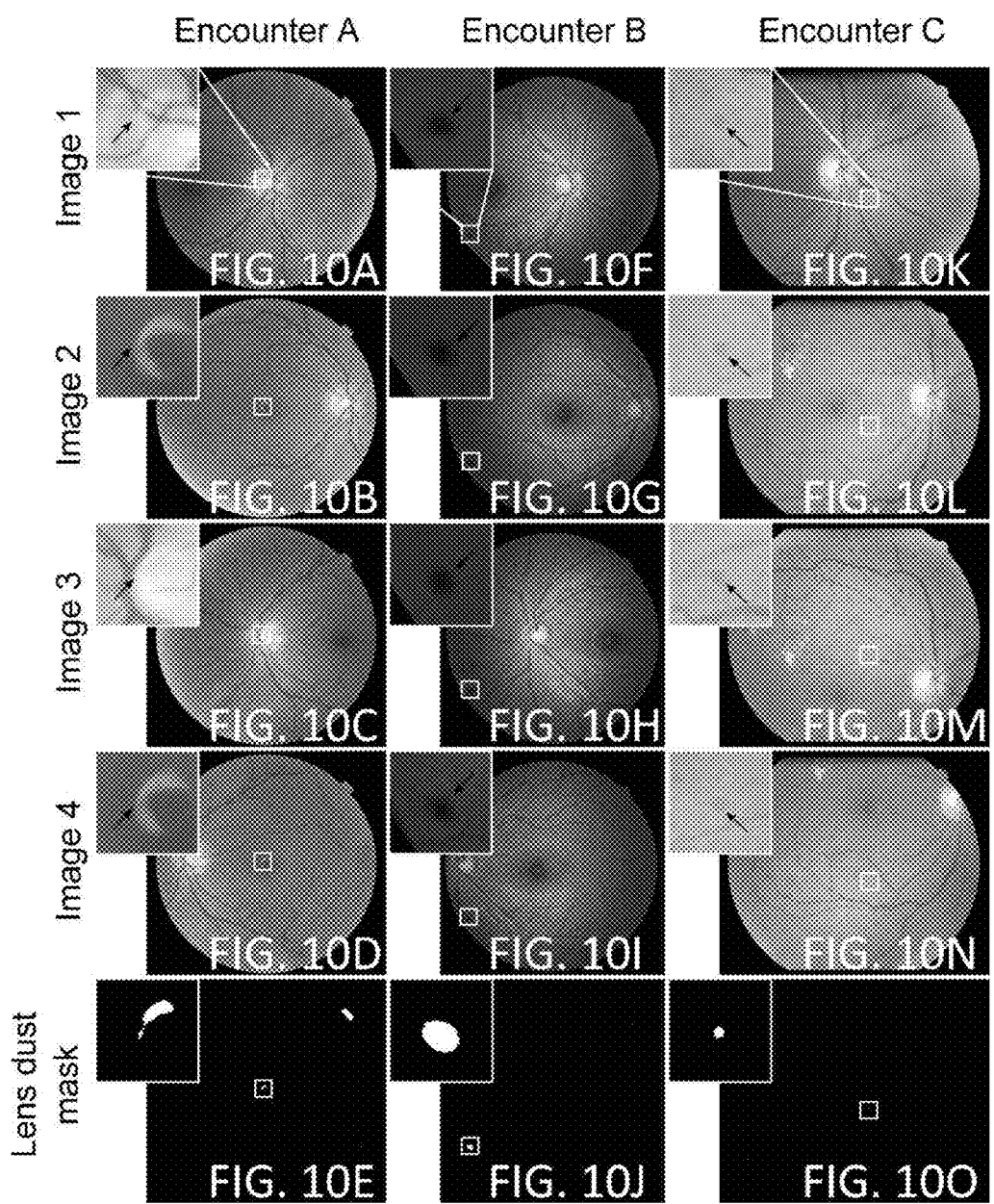
FIGS. 10A, 10B, 10C, and 10D show embodiments of retinal images from encounters with lens dust artifact displayed in the insets.
FIG. 10E shows an embodiment of an extracted lens dust binary mask using an embodiment of lens dust artifact detection.
FIGS. 10F, 10G, 10H, and 10I show embodiments of retinal images from one encounter with lens dust artifact displayed in the inset.
FIG. 10J shows an embodiment of an extracted lens dust binary mask using an embodiment of lens dust artifact detection.
FIGS. 10K, 10L, 10M, and 10N show embodiments of retinal images from one encounter with lens dust artifact displayed in the inset.
FIG. 10O shows an extracted lens dust binary mask using an embodiment of lens dust artifact detection.

FIG. 10 shows embodiments of retinal images from encounters with lens dust artifacts shown in the insets. Lens dust artifacts in images 1 through 4 of three different encounters are indicated by the black arrows within the magnified insets. The lens dust masks obtained for the three encounters using the above described process are shown in FIGS. 10E, 10J, and 10O. Encounter A (FIGS. 10A, 10B, 10C, and 10D) has a persistent bright light reflection artifact that is captured in the lens dust mask in FIG. 10E. The lens dust mask also incorrectly marks some smooth regions without lesions and vessels along the edge of the fundus that are similar across the images (top-right corner of FIG. 10E). However, such errors do not affect retinal image analysis since the regions marked do not have lesions nor vessels of interest. Encounter B (FIGS. 10F, 10G, 10H, and 10I) has a large, dark lens dust artifact that is captured in the lens dust mask in FIG. 10J. Encounter C (FIGS. 10K, 10L, 10M, and 10N) has a tiny, faint, microaneurysm-like lens dust artifact that is persistent across multiple images in the encounter. It is detected by the process and indicated in the lens dust mask in FIG. 10O.

In one embodiment, median filter radii of h=100 pixels and l=5 pixels are used to normalize the images. The hysteresis thresholding of the median normalized difference $I_{diff}^{(i),c}$ to obtain the bright mask is performed using an upper threshold that is the maximum of 50 and the 99th percentile of the difference values and a lower threshold that is the maximum of 40 and the 97th percentile of the difference values. The dark mask is obtained by hysteresis thresholding $-I_{diff}^{(i),c}$ (the negative of the median normalized difference) with an upper threshold; for example, the minimum of 60 and the 99th percentile of $-I_{diff}^{(i),c}$ and a lower threshold that is the minimum of 50 and the 97th percentile of $-I_{diff}^{(i),c}$. In one embodiment, groups of pixels with eccentricity less than 0.97 and with more than 6400 pixels are discarded. The smoothed normalized image $I_{h,smooth}^{(i),c}$ is obtained using a Gaussian smoothing filter with σ=2. To obtain the similarity mask as shown in FIG. 9D, $-I_{diff\_range}^{c}$ (the negative difference of the 80th and 20th percentile of the pair-wise absolute differences of $I_{h,smooth}^{(i),c}$) is hysteresis thresholded with an upper threshold that is the maximum of −5 and 95th percentile of $-I_{diff\_range}^{c}$ and a lower threshold that is the minimum of −12 and 90th percentile of $-I_{diff\_range}^{c}$. However, it is recognized that other values may be used to implement the processor.

D. Interest Region Detection

Typically, a large percentage of a retinal image comprises of background retina pixels which do not contain any interesting pathological or anatomic structures. Identifying interesting pixels for future processing can provide significant improvement in processing time, and in reducing false positives. To extract interesting pixels for a given query, multi-scale morphological filterbank analysis is used. This analysis allows the systems and methods to be used to construct interest region detectors specific to lesions of interest. Accordingly, a query or request can be submitted which has parameters specific to a particular concern. As one example, the query may request the system to return "bright blobs larger than 64 pixels in area but smaller than 400 pixels", or "red elongated structures that are larger than 900 pixels". A blob includes a group of pixels with common local image properties.

Figure 11:
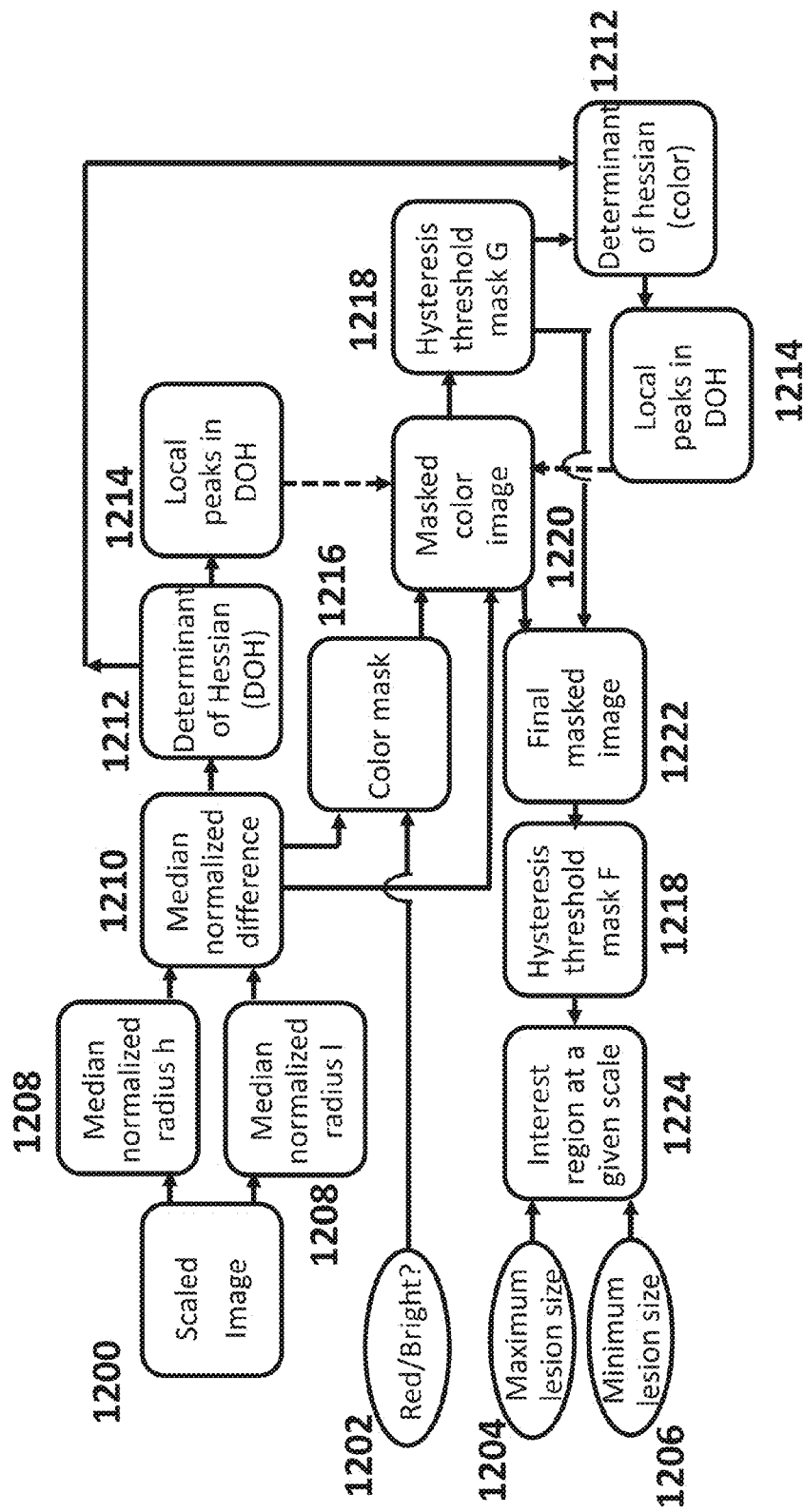
FIG. 11 is a block diagram of one embodiment for evaluating an interest region detector at a particular scale.

FIG. 11 depicts one embodiment of a block diagram for evaluating interest region pixels at a given scale. The illustrated blocks may be implemented either on the cloud 19014, a computer or computing device 19004, a mobile device 19008 or the like, as shown in FIG. 1. Scaled image 1200 is generated by resizing image 100 to a particular value. "Red/Bright?" 1202 indicates whether the lesion of interest is red or bright. Maximum lesion size 1204 indicates the maximum area (in pixels) of the lesion of interest. Minimum lesion size 1206 indicates the minimum area (in pixels) of the lesion of interest. Median normalized (radius r) 1208 is output of image enhancement block 106 when the background estimation is performed using a disk of radius r. Median normalized difference 1210 is the difference between two median normalized images 1208 obtained with different values of radius r. Determinant of Hessian 1212 is a map with the determinant of the Hessian matrix at each pixel. Local peaks in determinant of Hessian 1214 is a binary image with local peaks in determinant of Hessian marked out. Color mask 1216 is a binary image with pixels in the median normalized difference image 1210 over or below a certain threshold marked. Hysteresis threshold mask 1218 is a binary image obtained after hysteresis thresholding of input image. Masked color image 1220 is an image with just the pixels marked by color mask 1216 set to values as per median normalized difference image 1210. The pixel locations indicated by the local peaks in determinant of Hessian 1214 can be set to the maximum value in the median normalized difference image 1210 incremented by one. Final masked image 1222 is an image obtained by applying the hysteresis threshold mask 1218 to masked color image 1220. Interest region at a given scale 1224 is a binary mask marking interest regions for further analysis.

Retinal fundus image $I^{s_0}$ is scaled down by factor f, n times and scaled images $I^{s_0}, I^{s_1} \ldots I^{s_n}$ are obtained. In one embodiment, the ratio between different scales is set to 0.8 and 15 scales are used. At each scale $s_k$, the median normalized images $I_{Norm,r_h}^{s_k}$ and $I_{Norm,r_l}^{s_k}$ are computed with radius $r_h$ and $r_l$, $r_h > r_l$ as defined by Equation 1 where S defined as a circle of radius r. In one embodiment values of $r_h$=7 and $r_l$=3 can be used. Then, the difference image $I_{diff}^{s_k} = I_{Norm,r_h}^{s_k} - I_{Norm,r_l}^{s_k}$ is convolved with a Gaussian kernel, and gradients $L_{xx}(x,y)$, $L_{xy}(x,y)$, $L_{xy}(x,y)$ and $L_{yy}(x,y)$ are computed on this image. The Hessian H is computed at each pixel location (x, y) of the difference as:

$$H(x, y) = \begin{bmatrix} L_{xx}(x, y) & L_{xy}(x, y) \\ L_{xy}(x, y) & L_{yy}(x, y) \end{bmatrix} \quad \text{Equation 2}$$

where $L_{aa}$ (x, y) is second partial derivative in the a direction and $L_{ab}$ (x, y) is the mixed partial second derivative in the a and b directions. Determinant of Hessian map $L_{|H|}$ of the difference image $I_{diff}^{s_k}$ is the map of the determinant of H at each pixel. In one embodiment, given a query for red or bright lesion of minimum size $\min_{s_0}$ and maximum size $\max_{s_0}$ which are scaled to $\min_{s_k}$ and $\max_{S_k}$ respectively for scale $s_k$, the following operations are performed, as depicted in FIG. 11:

1. Mask M that marks red pixels in the scaled image $I^{s_k}$ is generated as follows.

$$M(x, y) = \begin{cases} 1 & \text{if } I_{diff}^{s_k}(x, y) < 0 \\ 0 & \text{otherwise} \end{cases}$$

Mask image M if bright pixels are to be marked.

$$M(x, y) = \begin{cases} 1 & \text{if } I_{diff}^{s_k}(x, y) > 0 \\ 0 & \text{otherwise} \end{cases}$$

2. Image with just red (or bright) pixels $I_{col}^{s_k}$ is generated by using mask M.

$$I_{col}^{s_k}(x,y) = I_{diff}^{s_k}(x,y) M(x,y)$$

3. Mask $P_{doh}$ containing the local peaks in determinant of Hessian $L_{|H|}$ is generated.

4. The maximum value $i_{max}^{s_k}$ in $I_{col}^{s_k}$ is found, and the pixels marked by mask $P_{doh}$ are set to $i_{max}^{s_k}+1$.

$$i_{max}^{s_k} = \max(I_{col}^{s_k})$$

$$I_{col}^{s_k}(x,y | P_{doh}(x,y)=1) = i_{max}^{s_k}+1$$

5. The resultant image $I_{col}^{s_k}$ is hysteresis thresholded with the high threshold $t^{hi}$ and low threshold $t^{lo}$ to obtain mask $G_{col}^{s_k}$. In one embodiment, $t^{hi}$ is set to the larger of 97 percentile of $I_{col}^{s_k}$ or 3, and $t^{lo}$ is set to the larger of 92 percentile of $I_{col}^{s_k}$ or 2.

6. The resulting mask $G_{col}^{s_k}$ is applied on determinant of Hessian map $L_{|H|}$ to obtain $L_{|H|,col}$.

$$L_{|H|,col}(x,y)=L_{|H|}(x,y)G_{col}^{s_k}(x,y)$$

7. Mask $P_{doh,col}$ containing the local peaks in determinant of Hessian $L_{|H|,col}$ is generated.
8. Pixels in $I_{col}^{s_k}$ marked by mask $P_{doh,col}$ are set to $i_{max}^{s_k}+1$.

$$I_{col}^{s_k}(x,y|P_{doh,col}(x,y)=1)=i_{max}^{s_k}+1$$

9. $I_{col}^{s_k}$ is then masked with $G_{col}^{s_k}$.

$$I_{col,masked}^{s_k}(x,y)=I_{col}^{s_k}(x,y)G_{col}^{s_k}(x,y)$$

10. The resultant image $I_{col,masked}^{s_k}$ is hysteresis thresholded with the high threshold $t^{hi}$ and low threshold $t^{lo}$ to obtain mask $F_{col}^{s_k}$. In one embodiment, $t^{hi}$ is set to the larger of $i_{max}^{s_k}$ or 3, and $t^{lo}$ is set to the larger of 92 percentile of $I_{col}^{s_k}$ or 2.
11. Locations with area larger than $max_{s_k}$ are removed from this mask $F_{col}^{s_k}$. Similarly locations with area smaller than $min_{s_k}$ are also removed. The locations indicated by the resulting pruned mask $Z_{col}^{s_k}$ are interesting regions scaled by $s_k$.

In another embodiment, $F_{col}^{s_k}$ is obtained after hysteresis thresholding $I_{col}^{s_k}$ in (3) above with the high threshold $t^{hi}$ and low threshold $t^{lo}$. This approach may lead to a larger number of interesting points being picked.

In another embodiment, the maximum number of interesting areas (or blobs) that are detected for each scale can be restricted. This approach may lead to better screening performance. Blobs can be ranked based on the determinant of Hessian score. Only the top M blobs per scale based on this determinant of Hessian based ranking are preserved in the interest region mask. Alternatively, a blob contrast number can be used to rank the blobs, where the contrast number is generated by computing mean, maximum, or median of intensity of each pixel within the blob, or by using a contrast measure including but not limited to Michelson contrast. The top M blobs per scale based on this contrast ranking are preserved in the interest region mask. Alternatively, at each scale, the union of the top M blobs based on contrast ranking and the top N blobs based on determinant of Hessian based ranking can be used to generate the interest region mask. Blobs that were elongated potentially belong to vessels and can be explicitly excluded from this mask. Blobs might be approximately circular or elongated. Approximately circular blobs may often represent lesions. Elongated blobs represent vasculature. The top blobs are retained at each scale and this is used to generate the $P_{doh,col}$ mask. The resultant $P_{doh,col}$ is then used to pick the detected pixels. Another variation used for $P_{doh,col}$ mask generation was logical OR of the mask obtained with top ranked blobs based on the doh score and the contrast score. Blot hemorrhages can be included by applying a minimum filter at each scale to obtain $G_{col}^{s_k}$ rather than using the median normalized difference image.

Figures 12A, 12B:
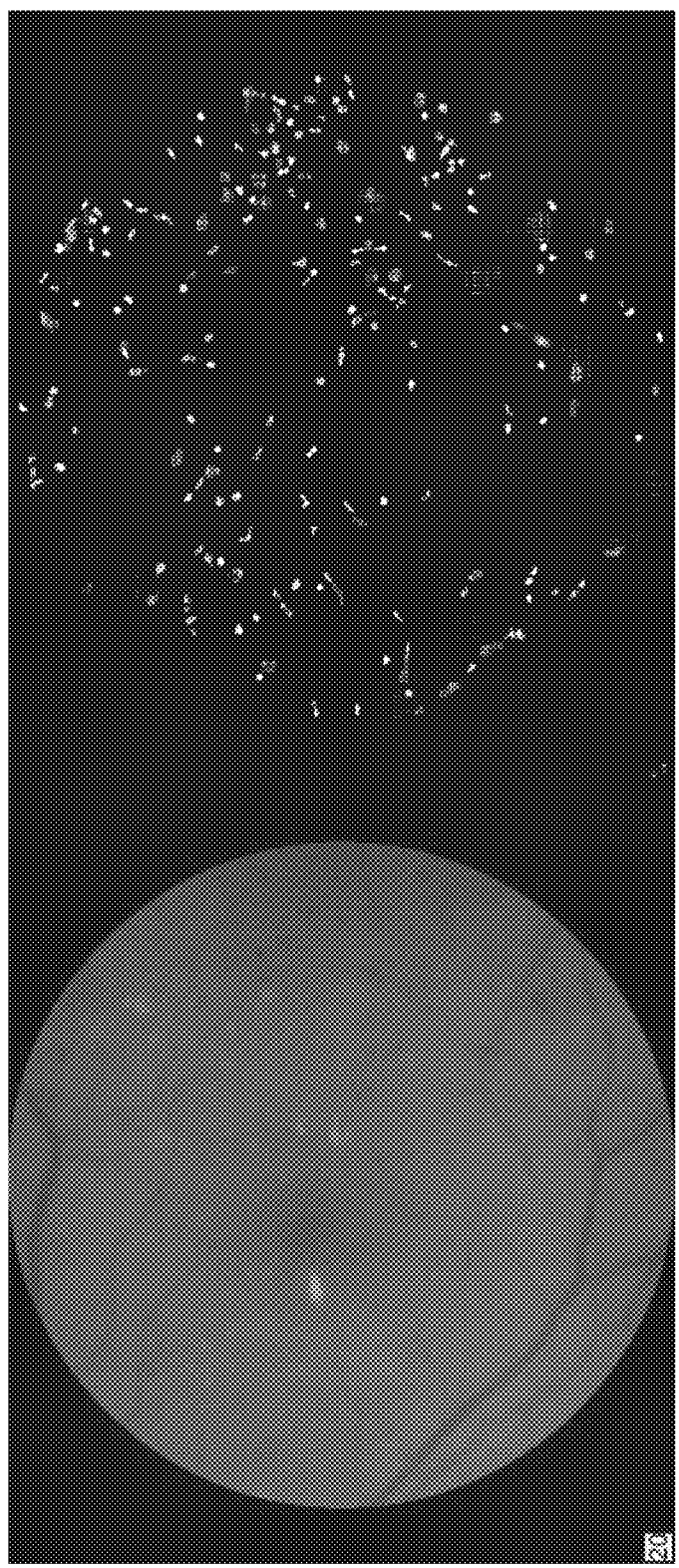
FIG. 12A shows one embodiment of an example retinal fundus image.
FIG. 12B shows one embodiment of an example of interest region detection for the image in FIG. 12A using one embodiment of the interest region detection block.

The pixels in the pruned mask $Z_{col}^{s_k}$ at each of the scale $s_k$ are rescaled to scale $s_0$ and the result is a set of pixels marked for further lesion analysis. This leads to natural sampling of large lesion blobs, choosing a subset of pixels in large blobs, rather than using all the pixels. In one embodiment, on average, retinal fundus images with over 5 million pixels can be reduced to about 25,000 "interesting" pixels leading to elimination of 99.5% of the total pixels. FIG. 12B shows the detected interest regions for an example retinal image of FIG. 12A.

As part of the automated detection, in one embodiment, the system may be configured to process the retinal image and during such processing progressively scale up or down the retinal image using a fixed scaling factor; designate groups of neighboring pixels within a retinal image as active areas; and include the active areas from each scale as interest regions across multiple scales.

E. Local Region Descriptors

The pixels or the local image regions flagged as interesting by the method described above in the section entitled "Interest Region Detection," can be described using a number or a vector of numbers that form the local region "descriptor". In one embodiment, these descriptors are generated by computing two morphologically filtered images with the morphological filter computed over geometric-shaped local regions (such as a structuring element as typically used in morphological analysis) of two different shapes or sizes and taking the difference between these two morphological filtered images. This embodiment produces one number (scalar) describing the information in each pixel. By computing such scalar descriptors using morphological filter structural elements at different orientations and/or image scales, and stacking them into a vector, oriented morphological descriptors and/or multi-scale morphological descriptors can be obtained. In one embodiment, a median filter is used as the morphological filter to obtain oriented median descriptors, and multi-scale median descriptors. In another embodiment, multiple additional types of local descriptors can be computed alongside the median and/or oriented median descriptors.

As part of the automated generation of descriptors, in one embodiment, the first geometric shape is either a circle or a regular polygon and the second geometric shape is an elongated structure with a specified aspect ratio and orientation, and the system is configured to generate a vector of numbers, the generation comprising: varying an orientation angle of the elongated structure and obtaining a number each for each orientation angle; and stacking the obtained numbers into a vector of numbers.

In another embodiment, the number or the vectors of numbers can be computed on a multitude of images obtained by progressively scaling up and/or down the original input image with a fixed scaling factor referred to as multi-scale analysis, and stacking the obtained vector of numbers into a single larger vector of numbers referred to as multi-scale descriptors.

These local region descriptors can be tailored to suit specific image processing and analysis applications such as, for example:
  i. describing landmark points for automated image registration (as described in the section below entitled "Detection And Description Of Landmark Points"),
  ii. evaluating the quality of images (as described in the section below entitled "Descriptors That Can Be Used For Quality Assessment"),
  iii. lesion localization (as described in the section below entitled "Processing That Can Be Used To Locate The Lesions").

IV. Automated Image Registration

A. General Description

This section describes embodiments directed to image-to-image registration. Image-to-image registration includes automated alignment of various structures of an image with another image of the same object possibly taken at a different time or different angle, different zoom, or a different field of imaging, where different regions are imaged with a small overlap. When applied to retinal images, registration can include identification of different structures in the retinal images that can be used as landmarks. It is desirable that these structures are consistently identified in the longitudinal images for the registration to be reliable. The input retinal images (Source image $I_{source}$, Destination image $I_{dest}$) can be split into two parts:

- constant regions in which structures are constant, for example, vessels ONH, and
- variable regions in which structures are changing, for example, lesions.

Figure 13A:
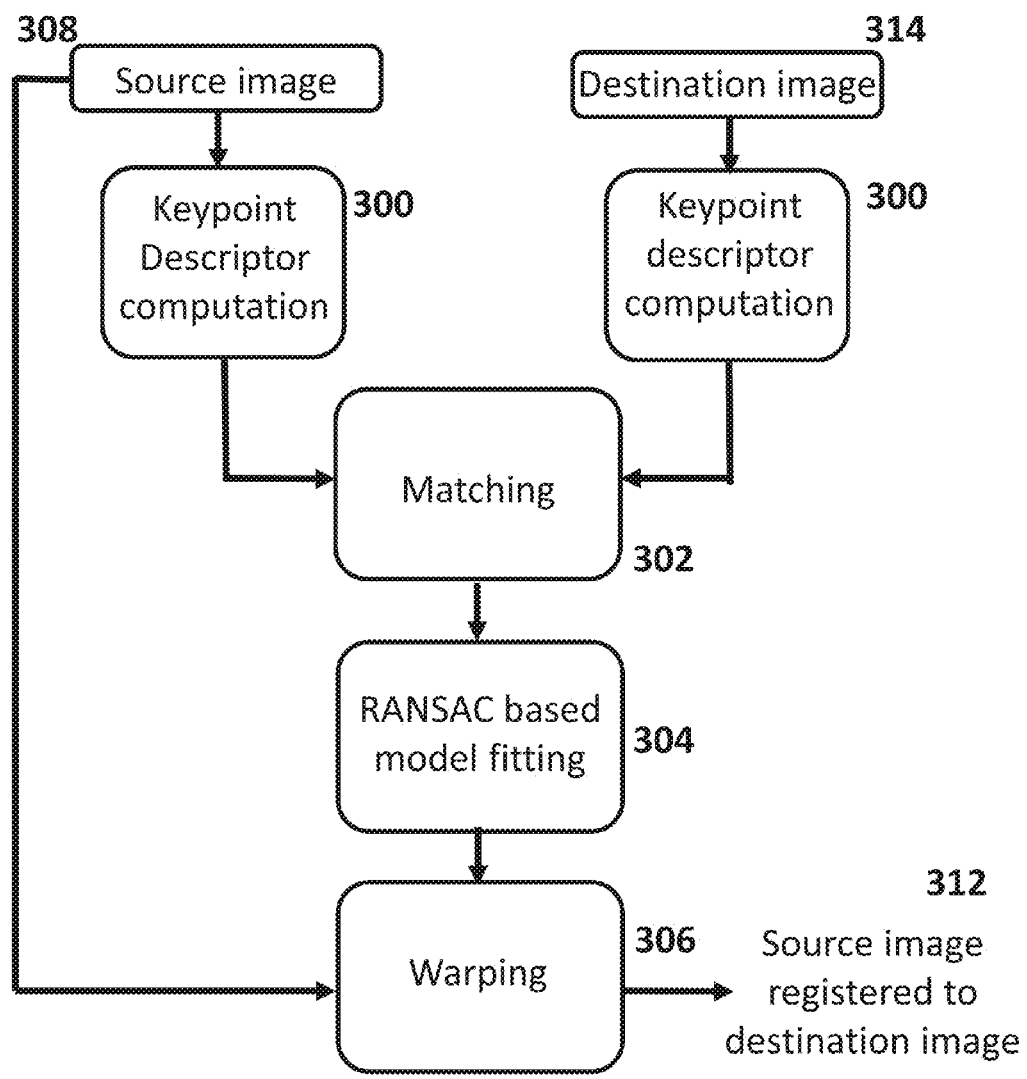
FIG. 13A is a block diagram of one embodiment of registration or alignment of a given pair of images.

Landmarks are detected at the constant regions and are matched using different features. These matches are then used to evaluate the registration model. FIG. 13A shows an overview of the operations involved in registering two images in one embodiment. The keypoint descriptor computation block 300 computes the descriptors used for matching image locations from different images. One embodiment of the keypoint descriptor computation block is presented in FIG. 13B. The blocks shown in FIGS. 13A and 13B here can be implemented on the cloud 19014, a computer or computing device 19004, a mobile device 19008, or the like as shown in FIG. 1. The matching block 302 matches image locations from different images. The RANdom Sample And Consensus (RANSAC) based model fitting block 304 estimates image transformations based on the matches computed by the matching block 302. The warping block 306 warps the image based on the estimated image transformation model evaluated by RANSAC based model fitting block 304. Source image 308 is the image to be transformed. Destination image 314 is the reference image to whose coordinates the source image 308 is to be warped using the warping block 306. Source image registered to destination image 312 is the source image 308 warped into the destination image 314 coordinates using the warping block 306.

B. Registration

1. Detection and Description of Landmark Points

Figure 13B:
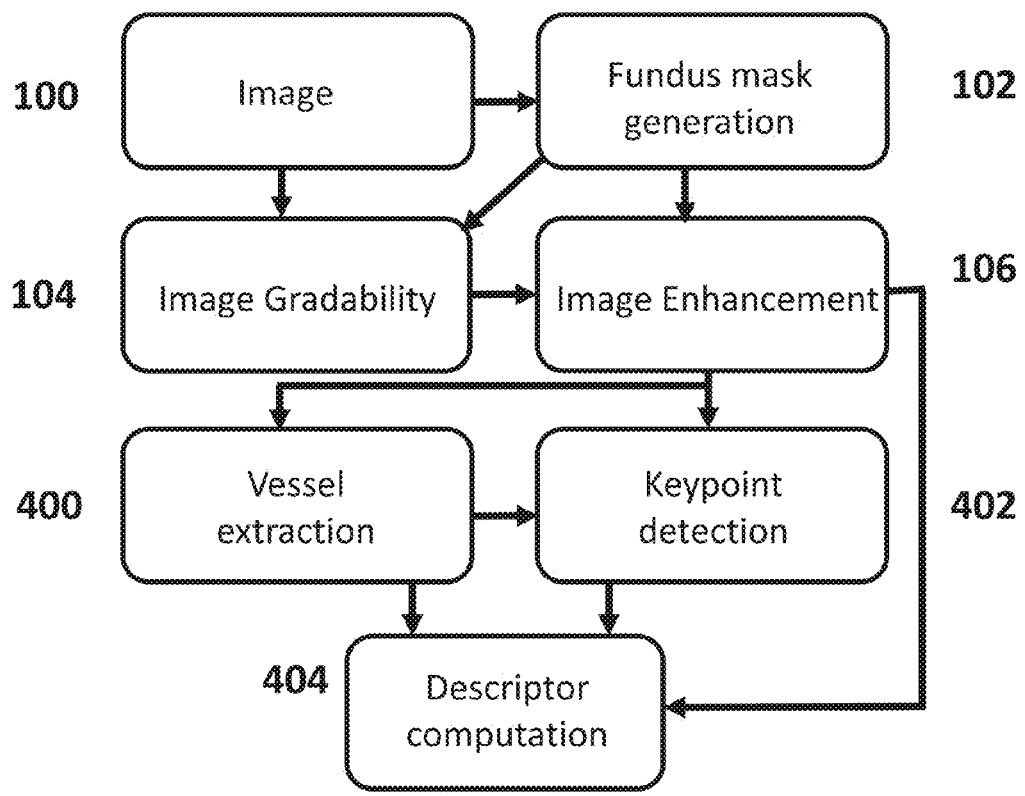
FIG. 13B is a block diagram of one embodiment of computation of descriptors for registering two images.

FIG. 13B provides an overview of descriptor computation for one embodiment of the image registration module. The image 100 can refer to the retinal data, single or multidimensional, that has been captured using a retinal imaging device, such as cameras for color image capture, fluorescein angiography (FA), adaptive optics, optical coherence tomography (OCT), hyperspectral imaging, scanning laser ophthalmoscope (SLO), wide-field imaging or ultra-wide-field imaging. Fundus mask generation block 102 can provide an estimation of a mask to extract relevant image sections for further analysis. Image gradability computation module 104 can enable computation of a score that automatically quantifies the gradability or quality of the image 100 in terms of analysis and interpretation by a human or a computer. Image enhancement module 106 can enhance the image 100 to normalize the effects of lighting, different cameras, retinal pigmentation, or the like. Vessel extraction block 400 can be used to extract the retinal vessels from the fundus image 100. Keypoint detection block 402 can evaluate image locations used for matching by matching block 302. Descriptor computation block 404 can evaluate descriptors at keypoint locations to be used for matching by matching block 302.

Branching of vessels can be used as reliable landmark points or keypoints for registration. By examining for blobs across multiple scales at locations with high vesselness, locations that are promising keypoints for registration can be extracted. In one embodiment, vesselness map is hysteresis thresholded with the high and low thresholds set at 90 and 85 percentiles respectively for the given image. These thresholds may be chosen based on percentage of pixels that are found to be vessel pixels on an average. The resulting binary map after removing objects with areas smaller than a predefined threshold, chosen, for example, based on the smallest section of vessels that are to be preserved, $V_{thresh}$, is used as a mask for potential keypoint locations. For example, 1000 pixels are used as the threshold in one embodiment, a value chosen based on the smallest section of vessels to be preserved.

In one embodiment, the fundus image can be smoothed with Gaussian filters of varying sigma, or standard deviation. In one implementation, the range of sigmas, or standard deviations, can be chosen based on vessel widths. For example, sigmas (σ) of 10, 13, 20 and 35 pixels can be used to locate vessel branches at different scales. Scale normalized determinant of Hessian can be computed at pixel locations labeled by V thresh at each of these scales. In one embodiment, local peaks in the determinant of Hessian map, evaluated with the minimum distance between the peaks, for example, $D=1+(\sigma-0.8)/0.3$, are chosen as keypoints for matching.

The local image features used as descriptors in some embodiments are listed below. Some descriptors are from a patch of N×N points centered at the keypoint location. In one embodiment, N is 41 and the points are sampled with a spacing of σ/10. Local image features used as descriptors for matching in one embodiment can include one or more of the following:

- Vector of normalized intensity values (from the green channel);
- Vector of normalized vesselness values;
- Histogram of vessel radius values from the defined patch at locations with high vesselness, for example, greater than 90 percentile vesselness over the image. (Using locations with high vesselness can ensure that locations with erroneous radius estimates are not used.)
- Oriented median descriptors (OMD): Vector of difference in responses between an oriented median filter and median filtered image These descriptors can provide reliable matches across longitudinal images with varying average intensities.

Figure 14:
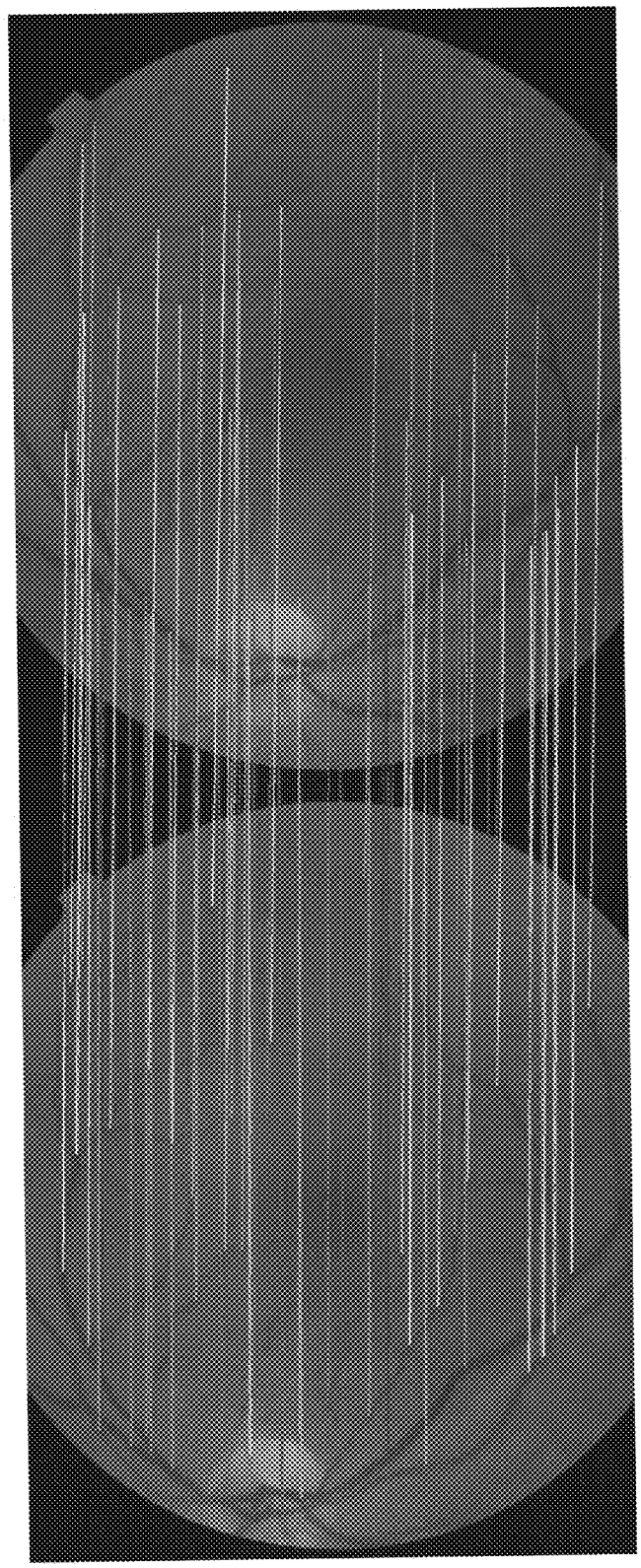
FIG. 14 shows embodiments of an example of keypoint matches used for defining a registration model, using one embodiment of the image registration module.

In one embodiment, the keypoints in the source and destination images are matched using the above defined descriptors. FIG. 14 shows matched keypoints from the source and destination images. In one embodiment, Euclidean distance is used to measure similarity of keypoints. In one embodiment, brute-force matching is used get the best or nearly best matches. In one embodiment, matches that are significantly better than the second best or nearly best match are preserved. The ratio of the distance between the best possible match and the second best or nearly best possible match is set to greater than 0.9 for these preserved matches. In one embodiment, the matches are then sorted based on the computed distance. The top M matches can be used for model parameter search using, for example, the RANSAC algorithm. In one embodiment, M can be 120 matches.

2. Model Estimation Using RANSAC

Some embodiments pertain to the estimation of the model for image to image registration. The RANSAC method can be used to estimate a model in the presence of outliers. This method is helpful even in situations where many data points are outliers, which might be the case for some keypoint matching methods used for registration. Some embodiments disclose a framework for model estimation for medical imaging. However, the disclosed embodiments are not limited thereto and can be used in other imaging applications.

The RANSAC method can include the following actions performed iteratively (hypothesize-and-test framework).

1. Hypothesize: Randomly select minimal sample sets (MSS) from the input dataset (the size of the MSS, k, can be the smallest number of data points sufficient to estimate the model). Compute the model parameters using the MSS.
2. Test: For the computed model, classify the other data points (outside the MSS) into inliers and outliers. Inliers can be data points within a distance threshold t of the model. The set of inliers constitutes the consensus set (CS).

These two actions can be performed iteratively until the probability of finding a better CS drops below a threshold. The model that gives the largest cardinality for the CS can be taken to be the solution. The model can be re-estimated using the points of the CS. The RANSAC method used can perform one or more of the following optimizations to help improve the accuracy of estimation, and efficiency of computation, in terms of number of the iterations.

Instead of using a fixed threshold for the probability of finding a better CS, the threshold is updated after each iteration of the algorithm.

For two iterations producing CS of the same size, the CS with lower residue or estimation error (as defined by the algorithm used for model estimation), is retained.

The random selection of points for building the MSS could result in degenerate cases from which the model cannot be reliably estimated. For example, homography computation might use four Cartesian points (k=4), but if three of the four points are collinear, then the model may not be reliably estimated. These degenerate samples can be discarded. Checks performed during image registration to validate the MSS can prevent or minimize the occurrence of three or more of collinear chosen points, as well as allowing the three points to be at a certain distance from each other to obtain good spatial distribution over the image.

3. Image Registration Models

Other processes for obtaining retinal image registration can be used. Customizations usable with the RANSAC method in order to compute the models are also provided.

A point on an image can be denoted as a 2D vector of pixel coordinates $[x\ y]^T \in \mathcal{R}^2$. It can also be represented using homogeneous coordinates as a 3D vector $[wx\ wy\ w]^T$ in projective space where all vectors that differ only by a scale are considered equivalent. Hence the projective space can be represented as $\mathcal{P}^2 = \mathcal{R}^3 - [0\ 0\ 0]$. The augmented vector $[x\ y\ 1]^T$ can be derived by dividing the vector components of the homogeneous vector by the last element w. The registration models can be discussed using this coordinate notation, with $[x\ y\ 1]^T$, the point in the original image, and $[x'\ y'\ 1]^T$, the point in the "registered" image.

The rotation-scaling-translation (RST) model can handle scaling by a factor s, rotation by an angle φ, and translation by $[t_x\ t_y]^T$. In one embodiment, the transformation process can be expressed as:

$$\begin{bmatrix} x' \\ y' \\ 1 \end{bmatrix} = \underbrace{\begin{bmatrix} s\cos\varphi & -s\sin\varphi & t_x \\ s\sin\varphi & s\cos\varphi & t_y \\ 0 & 0 & 1 \end{bmatrix}}_{T_\theta} \begin{bmatrix} x \\ y \\ 1 \end{bmatrix}. \qquad \text{Equation 3}$$

This model, denoted by $T_\theta$, can be referred to as a similarity transformation since it can preserve the shape or form of the object in the image. The parameter vector $\theta = [s\cos\varphi\ s\sin\varphi\ t_x\ t_y]^T$ can have 4 degrees of freedom: one for rotation, one for scaling, and two for translation. The parameters can be estimated in a least squares sense after reordering Equation 3 as:

$$\underbrace{\begin{bmatrix} x' \\ y' \end{bmatrix}}_{b} = \underbrace{\begin{bmatrix} x & -y & 1 & 0 \\ y & x & 0 & 1 \end{bmatrix}}_{A} \theta$$

The above matrix equation has the standard least squares form of Aθ=b, with θ being the parameter vector to be estimated. Each keypoint correspondence contributes two equations, and since total number of parameters is four, at least two such point correspondences can be used to estimate θ. In this example, the cardinality of MSS is k=2. The equations for the two point correspondences are stacked over each other in the above form Aθ=b, with A being a matrix of size 4×4, and b being vector of size 4×1. In this example, at each hypothesize operation of RANSAC, two point correspondences are randomly chosen and the parameters are estimated. The error between the ith pair of point correspondences $x_i$ and $x'_i$ for the computed model $T_\theta$ can be defined as:

$$e_i^2 \stackrel{def}{=} \underbrace{(\|x'_i - T_\theta(x_i)\|^2)}_{\text{reprojection error}} + \|x_i - T_\theta^{-1}(x'_i)\|^2 \qquad \text{Equation 4}$$

The first term in the above equation can be called the reprojection error and $e_i$ as a whole can be referred to as the symmetric reprojection error (SRE). In one embodiment, point correspondences whose SRE are below a certain threshold can be retained as inliers in the test operation of RANSAC. The average SRE over the points in the CS can be used as the residue to compare two CS of the same size.

The affine model can handle shear and can be expressed as:

$$\begin{bmatrix} x' \\ y' \\ 1 \end{bmatrix} = \underbrace{\begin{bmatrix} a_{11} & a_{12} & t_x \\ a_{21} & a_{22} & t_y \\ 0 & 0 & 1 \end{bmatrix}}_{T_\theta} \begin{bmatrix} x \\ y \\ 1 \end{bmatrix}.$$

In one embodiment, the parameter vector for affine model, θ, can be of size 6, and can be implemented with three point correspondences (k=3). In this example, the above equation can be re-written into the standard least squares form Aθ=b, with A being a matrix of size 6×6, and b being vector of size 6×1 for the three point correspondences. As before, θ can then be estimated using least squares. The selection of points for MSS can be done to avoid the degenerate cases by checking for collinearity of points. The SRE can then be computed (with T being the affine model), and used to validate inliers for CS and compute the residue for comparison of two CS of the same size.

The homography model can handle changes in view-point (perspective) in addition to rotation, scaling, translation, and shear and represented as:

$$\begin{bmatrix} x' \cdot w' \\ y' \cdot w' \\ w' \end{bmatrix} = \underbrace{\begin{bmatrix} \theta_1 & \theta_4 & \theta_7 \\ \theta_2 & \theta_5 & \theta_8 \\ \theta_3 & \theta_6 & \theta_9 \end{bmatrix}}_{H} \begin{bmatrix} x \\ y \\ 1 \end{bmatrix}.$$

In this example, even though the homography matrix H is a 3×3 matrix, it has only 8 degrees of freedom due to the w' scaling factor in the left-hand-side of the above equation. In order to fix the 9th parameter, an additional constraint of $\|\theta\|=1$ can be imposed, where $\theta=[\theta_1, \theta_2, \ldots, \theta_9]^T$. Estimation of this parameter vector can be performed with four point correspondences and done using the normalized direct linear transform (DLT) method/algorithm, which can produce numerically stable results. For the MSS selection, one or more of the following actions can be taken to avoid degenerate cases:

- Checking for collinearity of three or more points by computing the area of the triangle formed by the three points and checking if it is less than a predefined threshold, for example, 2 pixel-squared;
- Choosing distances between the chosen points greater than a threshold, for example, 32 pixels; or
- Preserving the order of points after transformation, for example, using techniques discussed in Pablo Marquez-Neila et al., "Speeding-up Homography Estimation in Mobile Devices," *Journal of Real-Time Image Processing* (Jan. 9, 2013).

The SRE can be used to form and validate the CS.

The quadratic model can be used to handle higher-order transformations such as x-dependent y-shear, and y-dependent x-shear. Since the retina is sometimes modeled as being almost spherical, a quadratic model is more suited for retinal image registration. In one embodiment, the model can be represented as:

$$\begin{bmatrix} x' \\ y' \end{bmatrix} = \underbrace{\begin{bmatrix} \theta_1 & \theta_2 & \theta_3 & \theta_4 & \theta_5 & \theta_6 \\ \theta_7 & \theta_8 & \theta_9 & \theta_{10} & \theta_{11} & \theta_{12} \end{bmatrix}}_{Q} \Psi\left(\begin{bmatrix} x \\ y \end{bmatrix}\right),$$

where $\Psi([x\ y]^T)$ is $[x^2\ xy\ y^2\ x\ y\ 1]^T$. Unlike RST, affine, or homography models, the quadratic model may not be invertible. In one embodiment, the model can have 12 parameters and 6 keypoint correspondences for estimation, that is, the size of MSS is k=6. The above equation can be rewritten in the standard least squares form $A\theta=b$, where the parameter vector $\theta=[\theta_1, \theta_2, \ldots, \theta_{12}]^T$, A is a matrix of size 12×12, and b is a vector of size 12×1 for the six point correspondences. $\theta$ can be estimated using least squares.

As with homography, MSS selection may be done to avoid degenerate cases. Since the transform may not be invertible, the reprojection error, that is, the first term on the right-hand-side of Equation 4, is computed and used to form and validate the CS.

The models discussed above present a set of models that can be used in one or more embodiments of the image registration module. This does not preclude the use of other models or other parameter values in the same methods and systems disclosed herein.

4. Registration Model Refinement

In one embodiment, an initial estimate of homography is computed as described in the section above entitled "Model Estimation Using RANSAC". Using the initial homography estimate, the keypoint locations in the source image, $I_{source}$ are transformed to the destination image, $I_{dest}$ coordinates. In one embodiment, the keypoint matching operation can be repeated with an additional constraint that the Euclidean distance between the matched keypoints in the destination image coordinates be lesser than the maximum allowable registration error $R_e$. In one embodiment, $R_e$ can be fixed at 50 pixels. This process constrains the picked matches and results, and can improve registration between the source and destination images.

Using the refined matches, various registration models can be fitted including Rotation-Scale-Translation (RST), Homography and Quadratic. In one embodiment, for each model, the minimum number of matches may be subtracted from the size of the obtained consensus set. In one embodiment, the model with the maximum resulting quantity can be chosen as the best model. If two models end up with identical values, then the simpler model of the two can be chosen as the best model.

5. Image Warping

Figure 15:
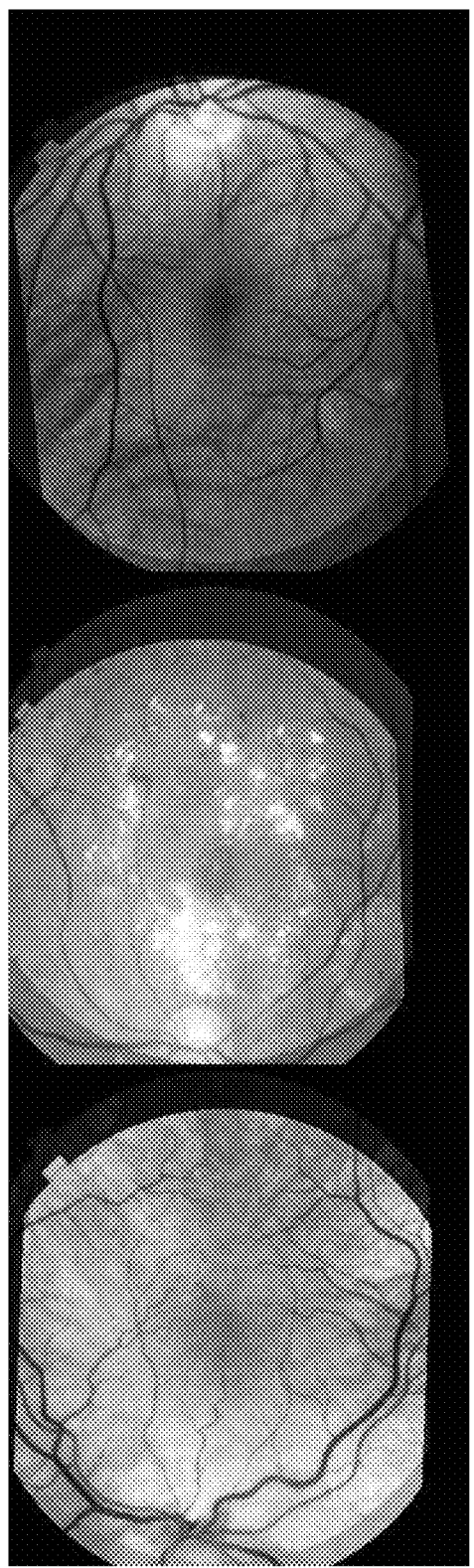
FIG. 15 shows embodiments of an example set of registered images using one embodiment of the image registration module.

An aspect of the image registration module may involve warping of the image to the coordinate system of the base image. FIG. 15 shows examples of source and destination images that are registered, warped, and overlaid on each other. In one embodiment, the computed registration models can be used to transform the pixel locations from the original image to the registered image. When transformation is applied directly, the integer pixel locations in the input image can map to non-integer pixel locations in the registered image, resulting in "holes" in the registered image, for example, when the registered image dimensions are larger than that of the input image. The "holes" can be filled by interpolating the transformed pixels in the registered image. Alternatively, inverse transform can be used to map registered pixel locations to the input image. For pixels that land at integer locations after inverse mapping, the intensity values can be copied from the input image, while the intensity values at non-integer pixels in input image can be obtained by interpolation.

The above approach can be applied to the invertible registration models such as RST, affine, or homography. If the non-invertible quadratic model is used, a forward transform $T_\theta$ can be used to build a mapping of the integer pixel locations in the input image to the registered image. To find the pixel intensity at an integer location in the registered image, the forward mapping can be checked for any input location maps to the registered location under consideration. If such a mapping exists, the intensity value is copied. In the absence of such a value, the n-connected pixel locations in an m×m neighborhood around the registered pixel can be checked. In one embodiment, n is 8 and m is 3. In one embodiment, the closest n pixels in the input image are found, and the pixel intensity at their centroid location is interpolated to obtain the intensity value at the required pixel location. This analysis may be helpful when pixels in a neighborhood in the input image stay in almost the same relative positions even in the registered image for retinal image registration. In another embodiment, the estimated quadratic model can be used to compute the forward mapping, swapping the input and registered pixel locations, and estimating the inverse mapping $\hat{T}_\theta^{-1}$ using least squares can be used to compute the forward mapping. A mapping can be applied to the integer locations in the registered image to generate the corresponding mapping from the input image.

V. Automated Image Assessment

In some embodiments, automated image assessment can be implemented using one or more features of the automated low-level image processing, and/or image registration techniques described above; however, using these techniques is not mandatory nor necessary in every embodiment of automated image assessment.

A. Lens Shot Image Classification

Figure 16:
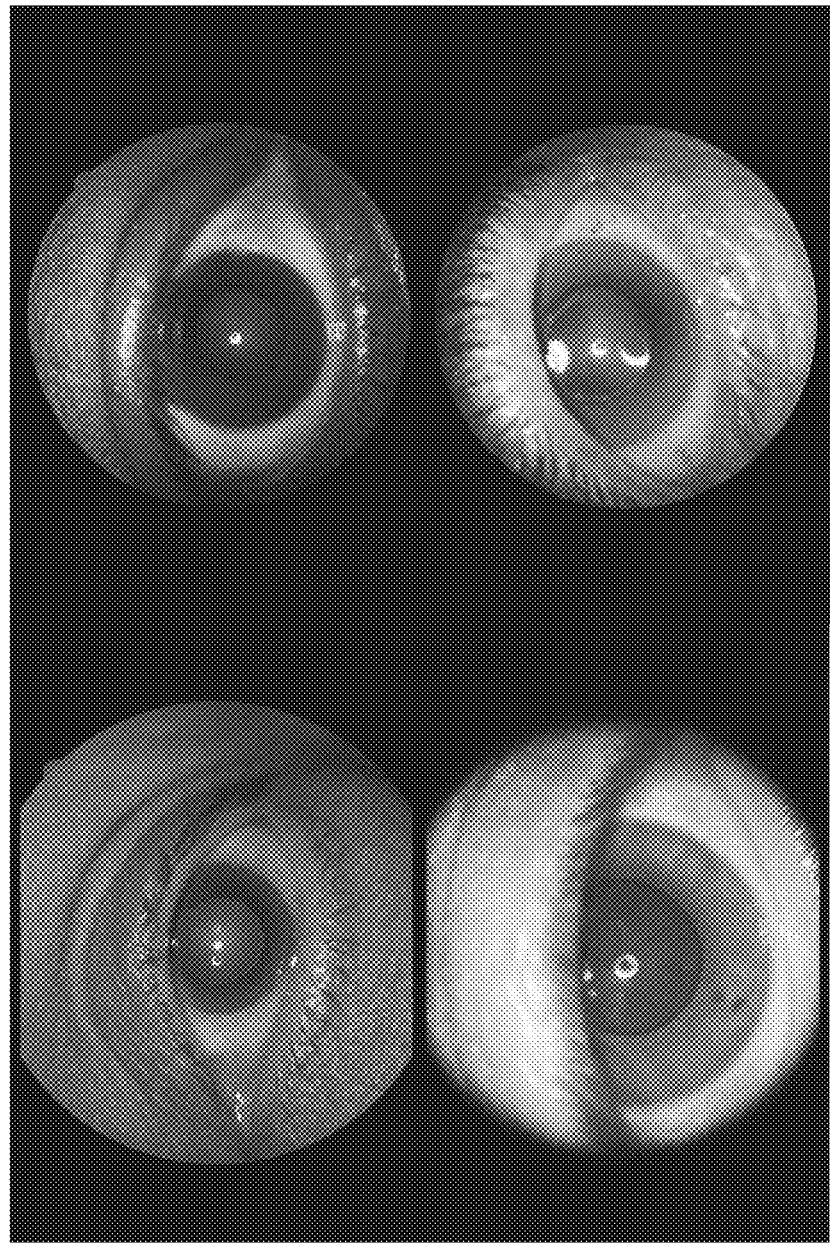
FIG. 16 shows example embodiments of lens shot images.

Typically multiple images of the fundus from various fields and both eyes are collected from a patient during a visit. In addition to the color fundus images, photographs of the patient's eye's lens may also be added to the patient encounter images, as illustrated in FIG. 16. In one embodiment, an automated DR screening system automatically and reliably separates these lens shot images from the actual color fundus images.

In one embodiment, lens shot image classification is achieved by primarily using structural and color descriptors. A given image is resized to a predetermined size. The histogram of orientations (HoG) feature is computed on the green channel to capture the structure of the image. The vesselness maps for images are computed, using for example the processes disclosed in the section below entitled "Vessel Extraction". The vesselness maps are hysteresis thresholded with the lower and higher thresholds set, for example, to 90 and 95 percentiles respectively to obtain a mask. The color histograms of the pixels within the mask are computed. The final descriptor is obtained by appending the color histogram descriptors to the HoG descriptors.

The order in which the images were obtained is also sometimes an indicator of an image being a lens shot image. This was encoded as a binary vector indicating absolute value of the difference between the image index and half the number of images in an encounter.

On a dataset of 10,104 images with over 2000 lens shot images on 50-50 train-test splits area under receiver operating characteristics (ROC) curve (AUROC) of over 0.998 were obtained.

B. Image Quality Assessment

1. General Description

In one embodiment, the system may include computer-aided assessment of the quality or gradability of an image. Assessment of image gradability or image quality can be important to an automated screening system. The factors that reduce quality of an image may include, for example, poor focus, blurred image due to eye or patient movement, large saturated and/or under-exposed regions, or high noise. In addition, the quality of image can be highly subjective. In the context of retinal image analysis, "image characteristics that allow for effective screening of retinopathy by a human grader or software" are preferred, whereas images with hazy media are flagged as being of insufficient quality for effective grading. Quality assessment can allow the clinician to determine whether he needs to immediately reimage the eye or refer the patient to a clinician depending on the screening setup employed.

Figure 17:
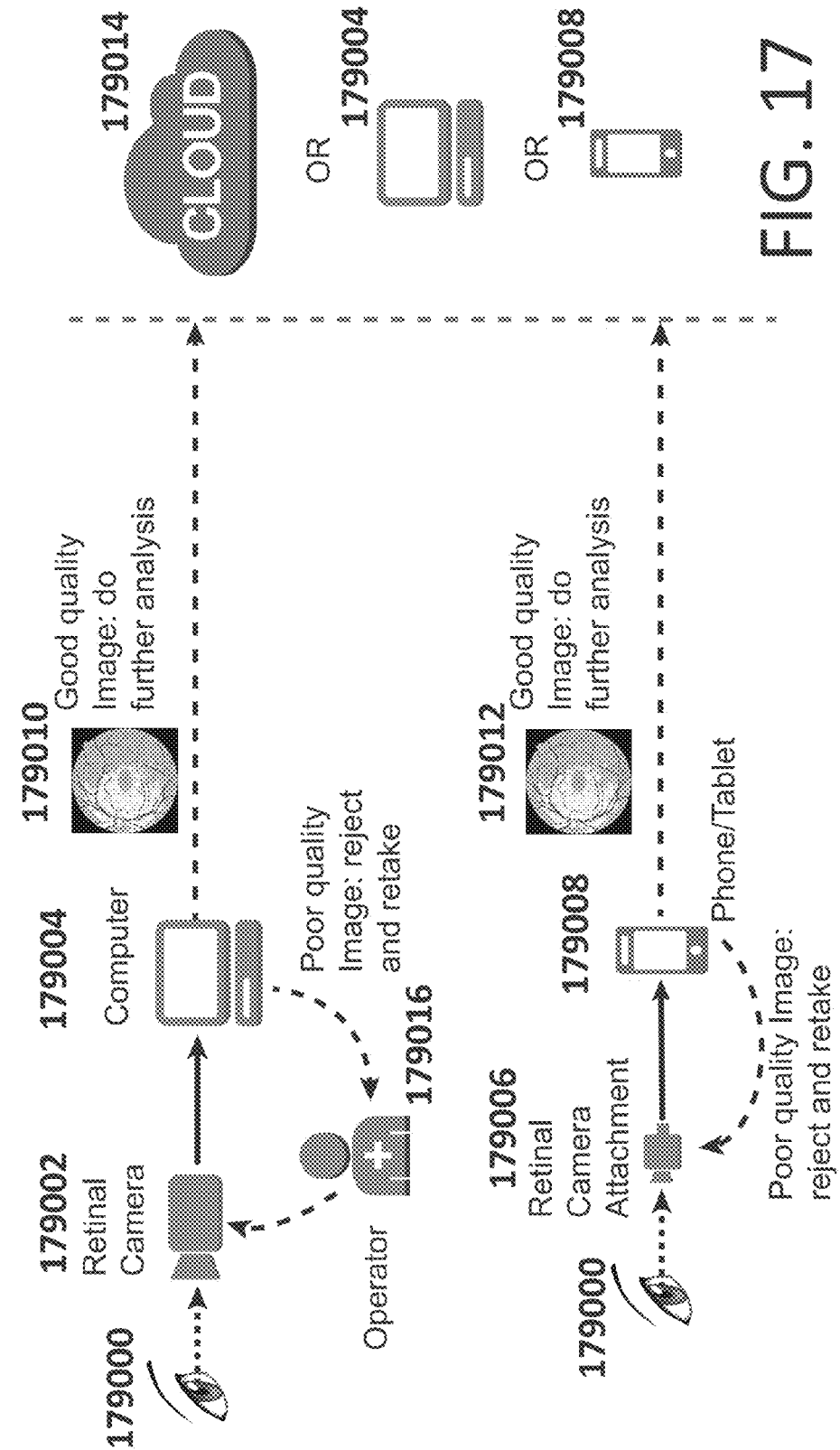
FIG. 17 illustrates various embodiments of an image quality analysis system and process.

FIG. 17 shows a detailed view of one embodiment of scenarios in which image quality assessment can be applied. The patient 179000 is imaged by an operator 179016 using an image capture device 179002. In this embodiment, the image capture device is depicted as a retinal camera. The images captured are sent to a computer or computing device 179004 for image quality analysis. Good quality images 179010 are sent for further processing for example on the cloud 179014, a computer or computing device 179004, a mobile device 179008, or the like. Poor quality images are rejected and the operator is asked to retake the image. In one embodiment a number is computed that reflects the quality of the image rather than simply classifying the image as of poor quality or not. In another embodiment, all captured images are sent to the cloud 179014, a computer or computing device 179004, a mobile device 179008, or the like, where the quality analysis takes place and the analysis results are sent back to the operator or the local computer or computing device 179004. In another embodiment, the computer itself could direct the image capture device to retake the image. In the second scenario, the patient 179000 takes the image himself using an image capture device 179006, which in this case is shown as a retinal camera attachment for a mobile device 179008. Quality analysis is done on the mobile device. Poor quality images are discarded and the image capture device is asked to retake the image. Good quality images 179012 are sent for further processing.

Figure 18:
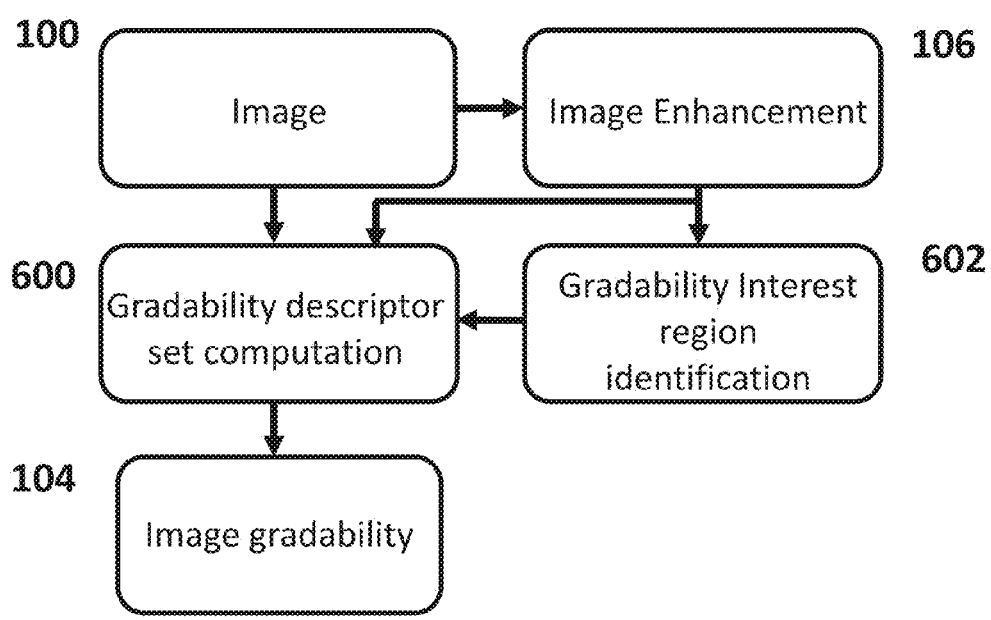
FIG. 18 is a block diagram of one embodiment for evaluating gradability of a given retinal image.

FIG. 18 gives an overview of one embodiment of a process for performing image quality computation. The illustrated blocks may be implemented on the cloud 179014, a computer or computing device 179004, a mobile device 179008, or the like, as shown in FIG. 17. The gradability interest region identification block 602 evaluates an indicator image that is true or false for each pixel in the original image and indicates or determines whether the pixel is interesting or represents an active region, so that it should be considered for further processing to estimate gradability of the image. Gradability descriptor set computation block 600 is configured to compute a single-dimensional or multi-dimensional float or integer valued vector that provides a description of an image region to be used to evaluate gradability of the image.

Figure 19:
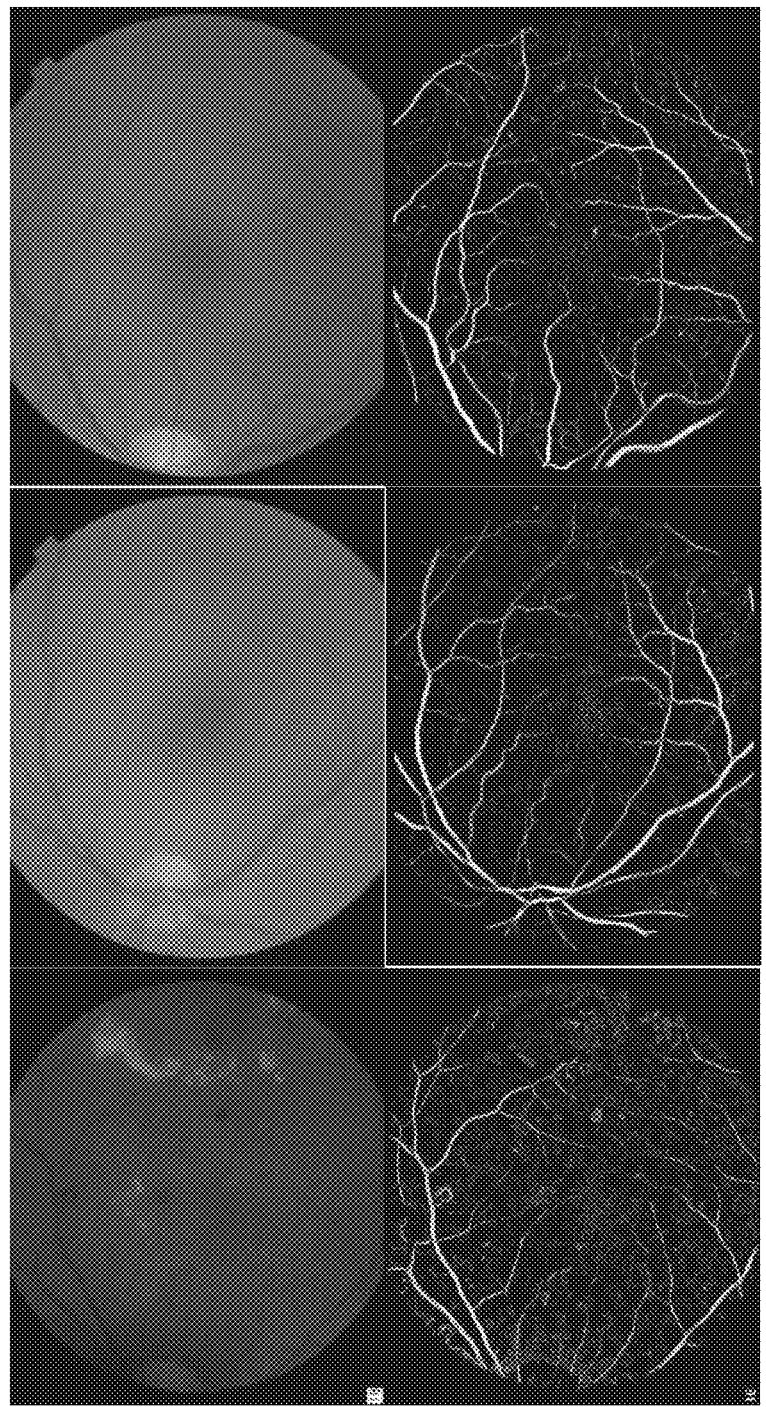
FIG. 19 shows one embodiment of example vessel enhancement images computed using one embodiment of the vesselness computation block.

In one embodiment, the images are first processed using a Hessian based interest region and "vesselness" map detection technique as shown in FIG. 19. The obtained image is then converted to a binary mask by employing hysteresis thresholding, followed by morphological dilation operation. The application of this binary mask to the original image greatly reduces the number of pixels to be processed by the subsequent blocks of the quality assessment pipeline, without sacrificing the accuracy of assessment.

Next, image quality descriptors are extracted using the masked pixels in the image. Table 1 is one embodiment of example descriptors that may be used for retinal image quality assessment.

TABLE 1

| Descriptor Name | Length | How it contributes |
|---|---|---|
| Local sum-modified Laplacian | 20 | Captures the degree of local focus/blur in an image |
| Local saturation descriptor | 20 × 2 | Captures the #pixels with "right" exposure |
| Local Michelson contrast | 20 | Captures the local contrast in an image |
| R,G,B color descriptors | 20 × 3 | Captures the degree of local focus/blur in an image |
| Local entropy descriptors | 20 | Captures the local texture |
| Local binary pattern descriptors | 20 | Captures the local texture |
| Local noise metric descriptors | 20 × 3 | Captures the local noise |

Figure 20:
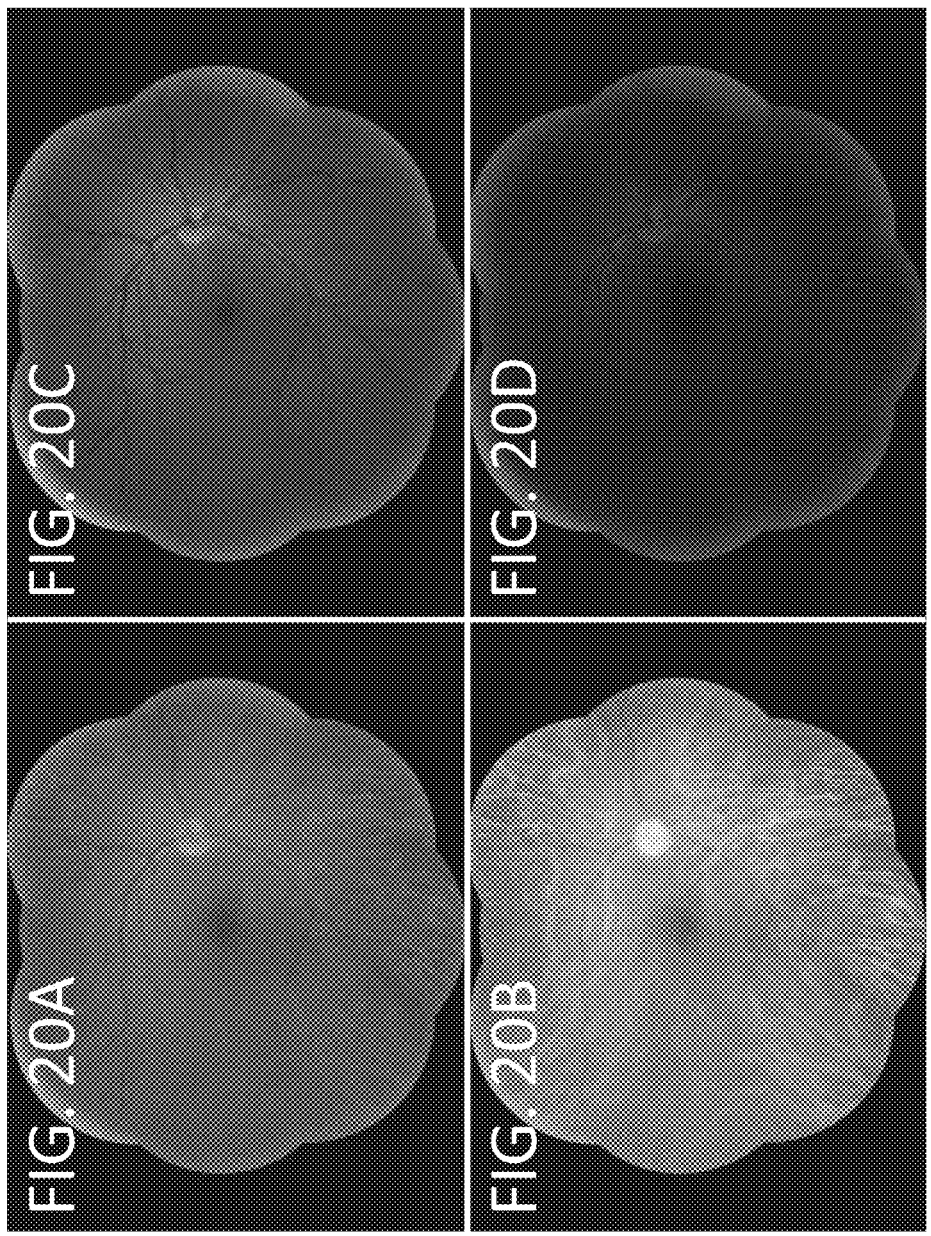
FIG. 20A shows an example of embodiments of visibility of retinal layers in different channels of an image-color fundus image.
FIG. 20B shows one embodiment of a red channel of a retinal image displaying vasculature from the choroidal layers.
FIG. 20C shows one embodiment of a green channel of a retinal image which captures the retinal vessels and lesions.
FIG. 20D shows one embodiment of a blue channel of a retinal image which does not capture much retinal image information.

In one embodiment, using 3-channel (RGB) color retinal fundus images, the green channel is preferred over red or blue channels for retinal analysis. This is because the red channel predominantly captures the vasculature in the choroidal regions, while the blue channel does not capture much information about any of the retinal layers. This is illustrated for an example color fundus image, shown in FIG. 20A as grayscale, with the red channel, shown in FIG. 20B as grayscale, the green channel, shown in FIG. 20C as grayscale, and the blue channel, shown in FIG. 20D as grayscale. Hence, in one embodiment, the green channel of the fundus image is used for processing. In other embodiments, all the 3 channels or a subset of them are used for processing.

In one embodiment, the system classifies images based on one or more of the descriptors discussed below:

2. Descriptors That Can Be Used For Quality Assessment a. Focus Measure Descriptors In one embodiment, for measuring the degree of focus or blur in the image, the sum-modified Laplacian is used. This has shown to be an extremely effective local measure of the quality of focus in natural images, as discussed in S. K. Nayar and Y. Nakagawa, "Shape from Focus," *IEEE Transactions on Pattern Analysis and Machine Intelligence* 16, no. 8 (1994): 824-831. For the input image I, the sum-modified Laplacian $I_{ML}$ at a pixel location (x, y) can be computed as $$I_{ML}(x,y) = |2I(x,y) - I(x-1,y) - I(x+1,y)| + |2I(x,y) - I(x,y-1) - I(x,y+1)|$$

A normalized histogram can be computed over the sum-modified Laplacian values in the image to be used as focus measure descriptor. In practice, $I_{ML}$ values that are too low, or too high may be unstable for reliably measuring focus in retinal images and can be discarded before the histogram computation. In one embodiment, the low and high thresholds are set to 2.5 and 20.5 respectively, which was empirically found to give good results. The computed descriptor has a length of 20. In practice, computing the focus descriptors on the image obtained after enhancement and additional bilateral filtering provides better gradability assessment results.

b. Saturation Measure Descriptors

In one embodiment, the local saturation measure captures the pixels that have been correctly exposed in a neighborhood, by ignoring pixels that have been under-exposed or over-exposed. The correctly exposed pixels are determined by generating a binary mask M using two empirically estimated thresholds, $S_{lo}$ for determining under-exposed pixels and $S_{hi}$ for determining over-exposed pixels. At a pixel location (x, y) the binary mask is determined as:

$$M(x, y) = \begin{cases} 1 & \text{if } S_{lo} < I(x, y) < S_{hi}, \\ 0 & \text{otherwise.} \end{cases}$$

The local saturation measure at location (x, y) is then determined as:

$$I_{Sat}(x, y) = \sum_{i,j \in \mathcal{D}} M(x-i, y-j),$$

where $\mathcal{D}$ is a neighborhood of pixels about the location (x, y). In one embodiment, $\mathcal{D}$ is a circular patch of radius r pixels. In one embodiment, the following values can be used for an 8-bit image: $S_{lo}=40$, $S_{hi}=240$, r=16. A normalized histogram is then computed over $I_{Sat}$ to generate the saturation measure descriptors. In one embodiment, the computed descriptor has a length of 20 for each channel. In addition to the saturation measure for the green channel, the inclusion of saturation measure for the blue channel was empirically found to improve the quality assessment.

c. Contrast Descriptors

In one embodiment, contrast is the difference in luminance and/or color that makes an object (or its representation in an image) distinguishable. The contrast measure may include Michelson-contrast, also called visibility, as disclosed in Albert A. Michelson, *Studies in Optics* (Dover Publications. com, 1995). The local Michelson-contrast at a pixel location (x,y) is represented as:

$$I_{MC}(x, y) = \frac{I_{max} - I_{min}}{I_{max} + I_{min}},$$

where $I_{min}$ and $I_{max}$ are the minimum and maximum pixel intensities in a neighborhood $\mathcal{D}$. In one embodiment, $\mathcal{D}$ is a circular patch of radius r pixels. A normalized histogram is then computed over $I_{MC}$ to obtain the contrast descriptors. In one embodiment, the computed descriptor has a length of 20.

d. RGB Color Descriptors

In one embodiment, normalized RGB color histograms are computed over the whole image and used as descriptors of color. In one embodiment, the computed descriptor has a length of 20 for each of the R, G, and B channels.

e. Texture Descriptors

In one embodiment, descriptors based on local entropy, for example using techniques disclosed in Rafael C. Gonzalez and Woods E. Richard, "Digital Image Processing," *Prentice Hall* Press, ISBN 0-201-18075-8 (2002), are incorporated to characterize the texture of the input image. For an image of bit-depth, B, the normalized histogram $p_i$ at pixel location (x, y), is first computed considering the pixels that lie in a neighborhood $\mathcal{D}$ around location (x, y). In one embodiment, $\mathcal{D}$ is a circular patch of radius r pixels. Denoting, the local normalized histogram as $p_i(x,y), i=0,1,\ldots,2^B-1$, the local entropy is obtained as:

$$I_{Ent}(x, y) = -\sum_{i=0}^{2^B-1} p_i(x, y) \cdot \log_2(p_i(x, y)),$$

A normalized histogram of the local entropy image $I_{Ent}$ is then used as a local image texture descriptor. In one embodiment, the computed descriptor would have a length of 20.

In addition to entropy, in another embodiment, local binary patterns (LBP) based descriptors are also computed to capture the texture in the image. The LBP can be computed locally for every pixel, and in one embodiment, the normalized histogram of the LBP image can be used as a descriptor of texture. The computed descriptor would still have a length of 20.

f. Noise Metric Descriptor

In one embodiment, since noise also affects the quality of an image, a noise metric descriptor for retinal images is also incorporated using, for example, techniques disclosed in Noriaki Hashimoto et al., "Referenceless Image Quality Evaluation for Whole Slide Imaging," *Journal of Pathology Informatics* 3 (2012):9. For noise evaluation, an unsharp masking technique may be used. The Gaussian filtered (blurred) retinal image G, is subtracted from the original retinal image, I, to produce a difference image D with large intensity values for edge or noise pixels. In one embodiment, to highlight the noise pixels, the center pixel in a 3×3 neighborhood $\mathcal{B}$ is replaced with the minimum difference between it and the 8 surrounding pixels as:

$$D_{min}(x, y) = \min_{i,j \in \{\mathcal{B}, (i,j) \neq (x,y)\}} |D(i, j) - D(x, y)|,$$

where (x, y) is the pixel location in the image. The resulting $D_{min}$ image has high intensity values for noise pixels. In one embodiment, a 20-bin normalized histogram of this image can be used as a noise metric descriptor. The descriptor can be computed for the three channels of the input retinal image.

3. Image Quality Classification or Regression

Figure 21:
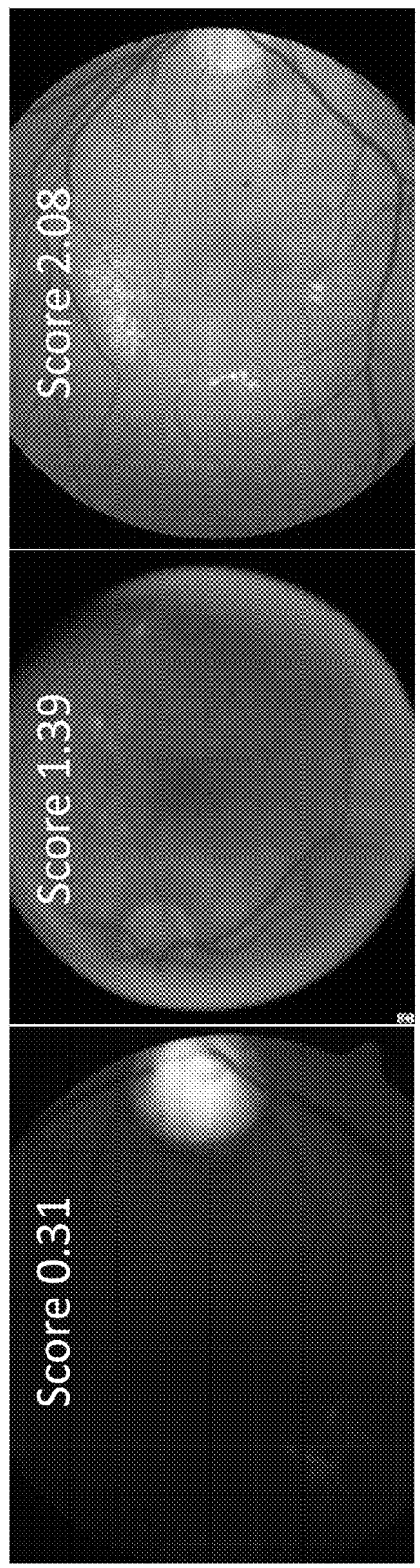
FIG. 21 shows an example of one embodiment of an automatic image quality assessment with a quality score output overlaid on retinal images.

In one embodiment, the system includes a classification action for image quality assessment. In another embodiment, regression analysis is conducted to obtain a number or value representing image quality. One or more quality descriptors discussed above are extracted and concatenated to get a single N-dimensional descriptor vector for the image. It is then subjected to dimensionality reduction, new dimension, M, using principal component analysis (PCA) to consolidate the redundancy among the feature vector components, thereby making quality assessment more robust. The PCA may include techniques disclosed in Hervé Abdi and Lynne J. Williams, "Principal Component Analysis," *Wiley Interdisciplinary Reviews: Computational Statistics* 2, no. 4 (2010): 433-459. In one embodiment the PCA-reduced descriptor then train a support vector regression (SVR) engine to generate a continuous score to be used for grading the images, for example, as being of poor, fair, or adequate quality. The SVR may include techniques disclosed in Harris Drucker et al., "Support Vector Regression Machines," Advances in Neural Information Processing Systems (1997): 155-161. In one embodiment, the parameters of the SVR were estimated using a 5-fold cross validation on a dataset of 125 images (73 adequate, 31 fair and 21 poor) labeled for retinopathy gradability by experts. FIG. 21 shows example images of varying quality that have been scored by the system. In another embodiment a support vector classifier (SVC) is trained to classify poor quality images from fair or adequate quality images. On the 125 image dataset, the adequate and fair quality images were classified from the poor quality images with accuracy of 87.5%, with an area under receiver operating characteristics (AUROC) of 0.90. Further improvements are expected with the incorporation of texture descriptors. In one embodiment, the descriptor vector has a length of N=140, which gets reduced to M=⌈N/8⌉ after PCA. In another embodiment, the entire descriptor vector is used, without the PCA reduction, to train a support vector classifier to distinguish poor quality images from good quality ones. This setup obtained an average accuracy of 87.1%, with an average AUROC of 0.88, over 40 different test-train splits of a retinal dataset of 10,000 images.

C. Vasculature Extraction

1. General Description

In one embodiment, the system is configured to identify retinal vasculature, for example, the major arteries and veins in the retina, in retinal images by extracting locations of vasculature in images. Vasculature often remains fairly constant between patient visits and can therefore be used to identify reliable landmark points for image registration. Additionally, vessels in good focus are indicative of good quality images, and hence these extracted locations may be useful during image quality assessment.

2. Identification Of Vessels a. Vessel Extraction

Figure 22:
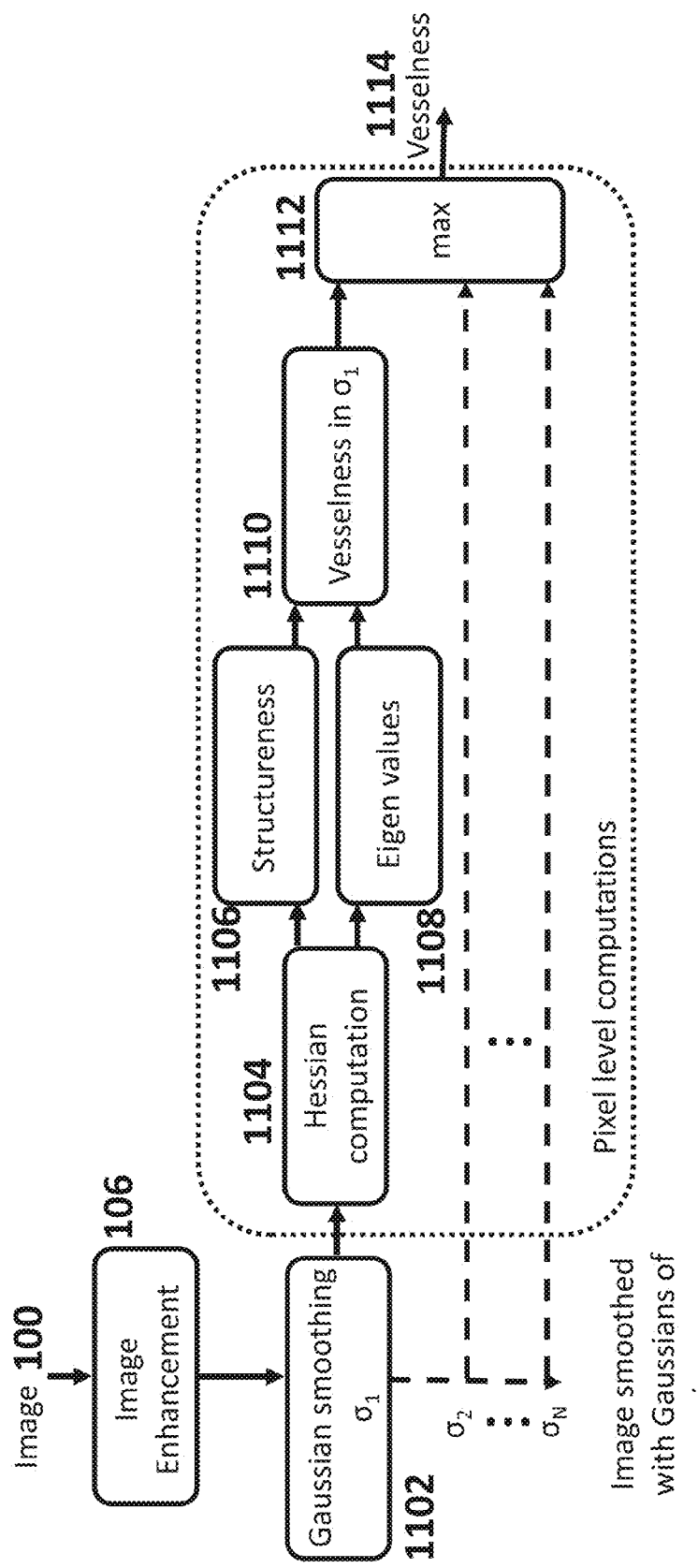
FIG. 22 is a block diagram of one embodiment for generating a vessel enhanced image.

One embodiment for vesselness computation is provided in FIG. 22. σ refers to the standard deviation of the Gaussian used for smoothing. Gaussian smoothing 1102 convolves the image with a Gaussian filter of standard deviation σ. This operation is repeated at different values of σ. Hessian computation 1104 computes the Hessian matrix (for example, using Equation 2) at each pixel. Structureness block 1106 computes the Frobenius norm of the Hessian matrix at each pixel. Eigen values 1108 of the Hessian matrix are computed at each pixel. Vesselness in $\sigma_1$ 1110 (Equation 5) is computed at a given pixel after smoothing the image with Gaussian smoothing block 1102 of standard deviation $\sigma_1$. The maximum 1112 at each pixel over multiple values of vesselness is computed at different smoothing. Vesselness 1114 indicates the vesselness of the input image 100.

In one embodiment, the vessels in the green channel of the color fundus image can be enhanced after pre-processing using a modified form of Frangi's vesselness using, for example, techniques disclosed in Alejandro F. Frangi et al., "Multiscale Vessel Enhancement Filtering," in *Medical Image Computing and Computer-Assisted Interventation—MICCAI'98* (Springer, 1998), 130-137 (Frangi et al. (1988)). The input image is convolved with Gaussian kernels at a range of scales. Gradients $L_{xx}$ (x,y), $L_{xy}$(x, y), $L_{xy}$(x, y) and $L_{yy}$(x, y) are then computed on these images and Hessian $H_s$ is computed at multiple scales using, for example, Equation 2.

A measure for tubular structures $$R_T = \frac{|\lambda_1|}{|\lambda_2|},$$

where $\lambda_1$ and $\lambda_2$ are the Eigen values of $H_s$ and $|\lambda_1| \le \lambda_2$ is computed. Structureness S is evaluated as the Frobenius norm of the Hessian. The vesselness measure at a particular scale is computed for one embodiment as follows:

$$V = \begin{cases} 0, & \text{if } \lambda_2 > 0, \\ e^{-\frac{R_T^2}{2\beta^2}}\left(1 - e^{-\frac{S^2}{2c^2}}\right) & \text{otherwise} \end{cases} \quad \text{Equation 5}$$

Figure 23:
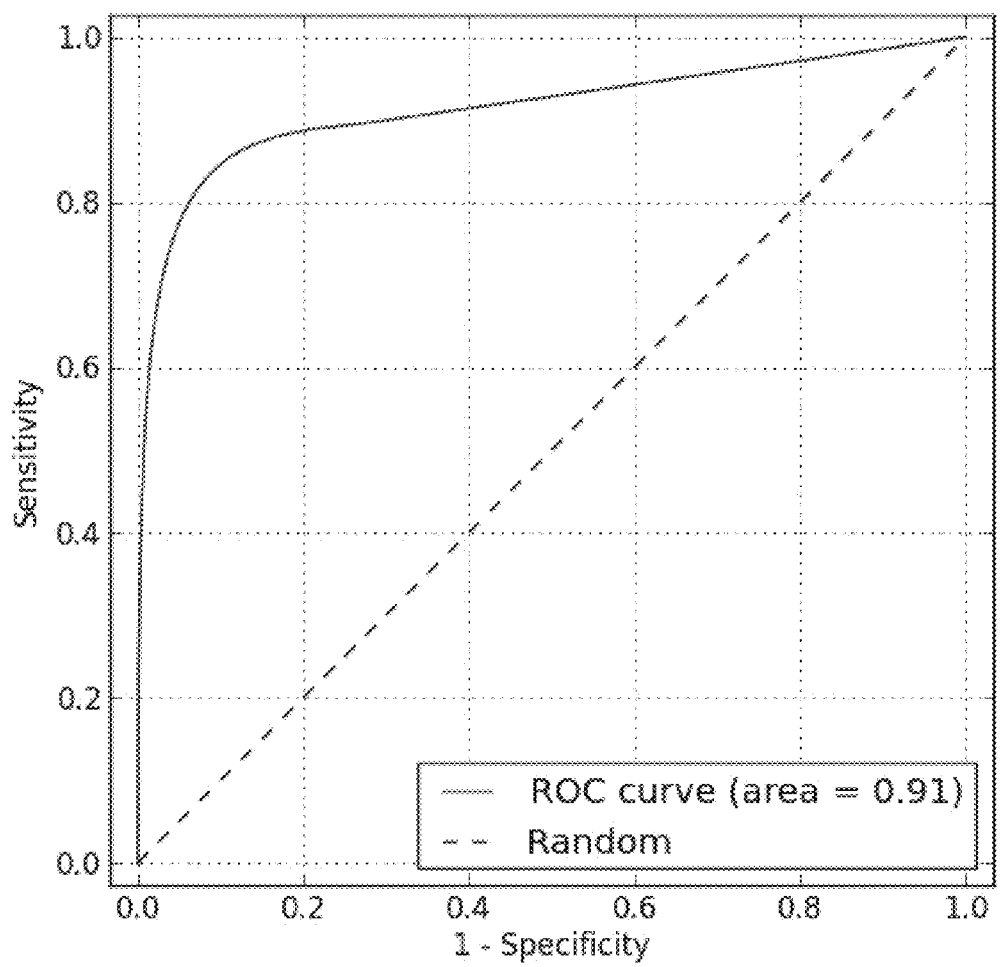
FIG. 23 shows one embodiment of a receiver operating characteristics (ROC) curve for vessel classification obtained using one embodiment of a vesselness computation block on a STARE (Structured Analysis of the Retina) dataset.

In one embodiment, β is fixed at 0.5 as per Frangi et al. (1998), and c is fixed as the 95 percentile of the structureness S. The vesselness measure across multiple scales is integrated by evaluating the maximum across all the scales. Vesselness over multiple standardized datasets were evaluated using, for example, DRIVE, as disclosed in Joes Staal et al., "Ridge-Based Vessel Segmentation in Color Images of the Retina," *IEEE Transactions on Medical Imaging* 23, no. 4 (April 2004): 501-509, and STARE, as disclosed in A. Hoover, V. Kouznetsova, and M. Goldbaum, "Locating Blood Vessels in Retinal Images by Piecewise Threshold Probing of a Matched Filter Response," *IEEE Transactions on Medical Imaging* 19, no. 3 (2000): 203-210. The combination of the custom image enhancement and modified Frangi vesselness computation can result in performance that is close to the state of the art. In one embodiment, the unsupervised, non-optimized implementation takes less than 10s on a 605×700 pixel image. Some example vessel segmentations are shown in FIG. 19. The receiver operating characteristics (ROC) curve of one embodiment on the STARE dataset is shown in FIG. 23. Table 2 compares the AUROC and accuracy of one embodiment of the system on the DRIVE and STARE datasets with human segmentation. This embodiment has better accuracy with respect to gold standard when compared to secondary human segmentation.

TABLE 2

| | Accuracy (%) | | |
|---|---|---|---|
| | EyeTrace | Human | AUROC |
| DRIVE | 95.3% | 94.7% | 0.932 |
| STARE | 95.6% | 93.5% | 0.914 |

Figure 24:
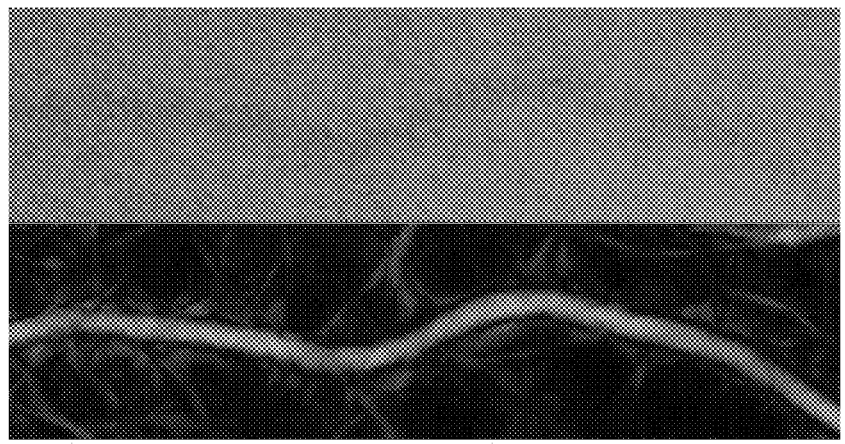
FIG. 24 shows one embodiment of images generated using one embodiment of a vesselness computation block.

In one embodiment, the vesselness map is then processed by a filterbank of oriented median filters. In one embodiment, the dimensions of the median filters are fixed based on the characteristics of the vessels to be preserved, for example, Height=3 pixels, Length=30 pixels, or 8 orientations. At each pixel, the difference between the maximum and median filter response across orientations was evaluated. This provides a vasculature estimate that is robust to identify the presence of blob lesions or occlusions. FIG. 24 shows an example vessel extraction using the custom morphological filterbank analysis on a poor quality image.

b. Vessel Tracing

In one embodiment, level-set methods such as fast marching are employed for segmenting the vessels and for tracing them. For example, fast marching can be used with techniques disclosed in James A. Sethian, "A Fast Marching Level Set Method for Monotonically Advancing Fronts," *Proceedings of the National Academy of Sciences* 93, no. 4 (1996): 1591-1595. The vessel tracing block may focus on utilizing customized velocity functions, based on median filterbank analysis, for the level-sets framework. At each pixel location the velocity function is defined by the maximum median filter response. This embodiment leads to an efficient, mathematically sound vessel tracing approach. In one embodiment, automatic initialization of start and end points for tracing the vessels in the image is performed using automated optic nerve head (ONH) identification within a framework that provides a lesion localization system.

D. Lesion Localization

1. General Description

Figure 25:
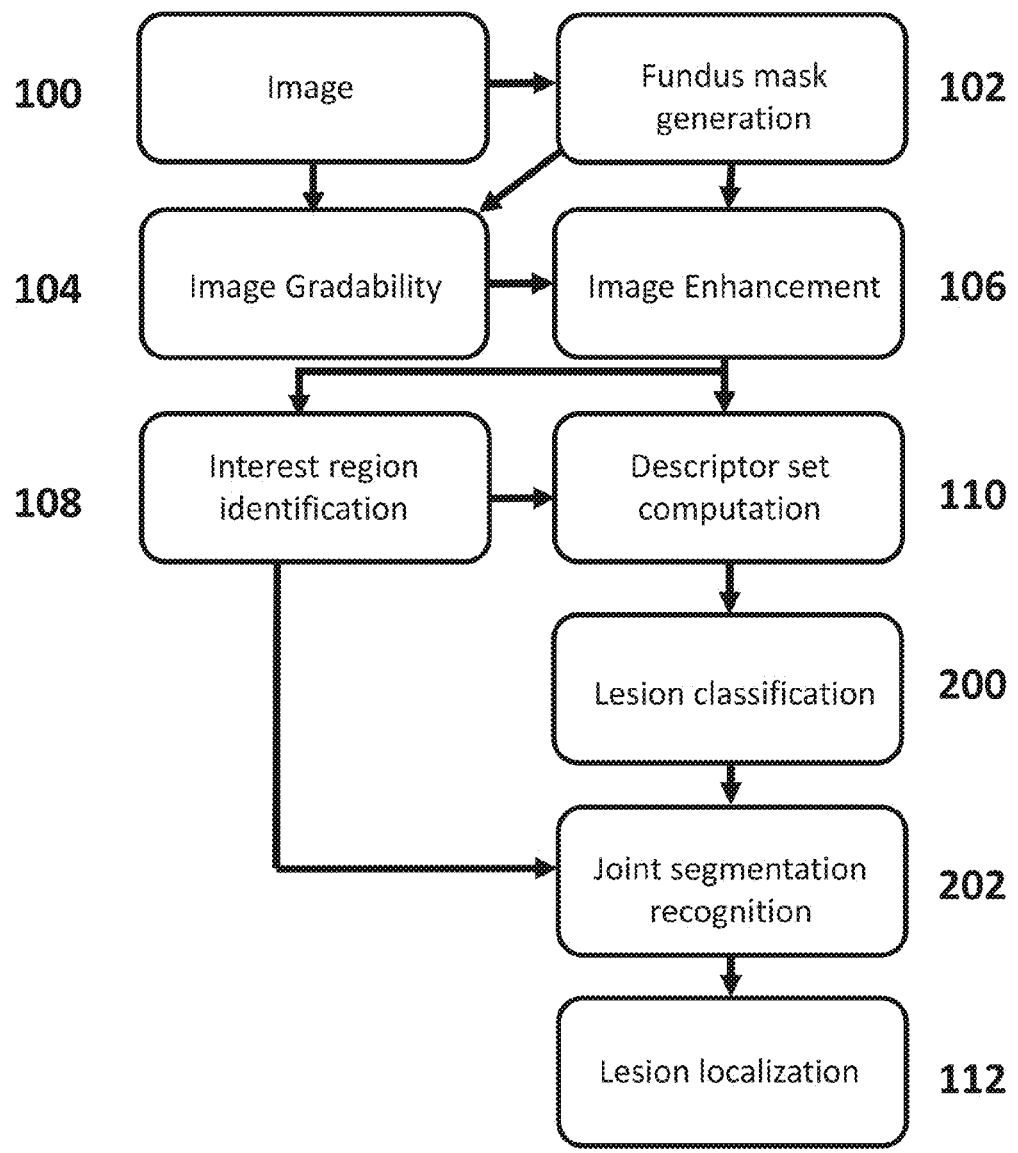
FIG. 25 is a block diagram of one embodiment of a setup to localize lesions in an input retinal image.

In one embodiment, the system is configured to localize lesions in retinal images. The lesions may represent abnormalities that are manifestations of diseases, including diabetic retinopathy, macular degeneration, hypertensive retinopathy, and so forth. FIG. 25 depicts one embodiment of a lesion localization process. The illustrated blocks may be implemented on the cloud 19014, a computer or computing system 19004, a mobile device 19008, or the like, as shown in FIG. 1. The image 100 refers in general to the retinal data, single or multidimensional, that has been captured using a retinal imaging device, such as cameras for color image capture, fluorescein angiography (FA), adaptive optics, optical coherence tomography (OCT), hyperspectral imaging, scanning laser ophthalmoscope (SLO), wide-field imaging or ultra-wide-field imaging. Fundus mask generation block 102 estimates the mask to extract relevant image sections for further analysis. Image gradability computation module 104 computes a score that automatically quantifies the gradability or quality of the image 100 in terms of analysis and interpretation by a human or a computer. Image enhancement module 106 enhances the image 100 to normalize the effects of lighting, different cameras, retinal pigmentation, or the like. Interest region identification block 108 generates an indicator image with a true or false value for each pixel in the original image, that indicates or determines whether the pixel is interesting or represents active regions that may be considered for further processing. Descriptor set computation block 110 computes a single- or multi-dimensional float or integer valued vector that provides a description of an image region. Examples include shape, texture, spectral, or other descriptors. Lesion classification block 200 classifies each pixel marked by interest region identification block 108 using descriptors computed using descriptor set computation block 110 into different lesions. Joint segment recognition block 202 analyzes the information and provides an indicator of any recognized lesions.

2. Processing That Can Be Used To Locate The Lesions a. Interest Region Detection In some embodiments, interest region detection techniques described in the section above entitled "Interest Region Detection" can be used to locate lesions.

b. Descriptor Computation

In one embodiment, a set of descriptors that provide complementary evidence about presence or absence of a lesion at a particular location can be used. Embodiments of the disclosed framework developed can effectively describe lesions whose sizes vary significantly (for example hemorrhages and exudates) due to local description of interest regions at multiple scales.

Table 3 lists one embodiment of pixel level descriptors used for lesion localization and how the descriptors may contribute to lesion classification.

TABLE 3

| Descriptor Name | Length | How it contributes |
| --- | --- | --- |
| Median filterbank | 90 | Bandpass median filter responses at multiple scales. Robustly characterizes interesting pixels |
| Oriented median filterbank | 120 | Robustly distinguish elongated structures from blob-like structures |
| Hessian based descriptors | 70 | Describes local image characteristics of blobs and tubes, such as local sharpness |
| Blob statistics descriptors | 80 | Detects blob like structures with statistics on blob shape, size, and color |
| Gaussian derivative | 20 | Useful in extracting structures such as microaneurysms |
| Color descriptor | 30 | Average color in RGB space in a local neighborhood |
| Filterbank of Fourier spectral descriptors | 20 | Extracts edge layout and local textures, independent of local intensity |
| Localized Gabor jets descriptors | 400 | Extracts local spectral information concerning form and texture without sacrificing information about global spatial relationships |
| Filterbank of matched filters | 80 | Allows localization of small lesions such as microaneurysms. Can also be adapted for vessels |
| Path opening and closing based morphological descriptors filterbank | 20 | Effectively captures local structures, such as "curvy" vessels |
| Filterbank of local binary patterns descriptors | 200 | Captures local texture information, can help achieve distinction between lesion and background or other anatomical structures |

Many of the descriptor sets are developed specifically for retinal images, with a focus on low-level image processing. Measures of local image properties alongside with some retinal fundus image specific measures at multiple scales can be used. Each of the descriptors listed below can be computed on scaled images $I^{s_0}, I^{s_1} \ldots I^{s_n}$. In one embodiment, the ratio between different scales is set to 0.8 and 10 scales are used. Examples of multi-scale descriptors that can be used for lesion localization and/or screening at each interest pixel $(X_{int}, y_{int})$ are listed above in Table 3. The following provides information about one or more descriptors that may be used.

Morphological Filterbank Descriptors:

At each scale $s_k$ a morphological filter can be applied to the image with the morphological filter computed over circles, squares, or regular polygons or different sizes. For example, circles of different radii can be used. In one embodiment, the median filtering is used as the said morphological filter. In this embodiment, at each scale $s_k$ the median normalized RGB images $A_{Norm,r_j}^{s_k}$ are computed (for example, using Equation 1) with medians computed within circles of different values of radius $r_j$, such that $r_j > r_{j-1}$.

$$A_{diff,j-1}^{s_k} = A_{Norm,r_j}^{s_k} - A_{Norm,r_{j-1}}^{s_k}$$

In one embodiment, median filterbank descriptor is $A_{diff,j-1}^{s_k}$ $(x_{int}, y_{int})$ for all values of j. In one embodiment, $r_j = \{7, 15, 31\}$, $j=1,2,3$, and $r_0=3$.

In one embodiment, the morphological filterbank descriptors are computed employing the following: generating a first morphological filtered image using the retinal image, with a the said morphological filter computed over a first geometric shape; generating a second morphological filtered image using the retinal image, with a morphological filter computed over a second geometric shape, the second geometric shape having one or more of a different shape or different size from the first geometric shape; generating a difference image by computing a difference between the first morphological filtered image and the second median filtered image; and assigning the difference image pixel values as a descriptor value each corresponding to given pixel location of the said retinal image. In one embodiment, the morphological filter employed is a median filter. In one embodiment these descriptors are evaluated on a set of images obtained by progressively resizing the original image up and/or down by a set of scale-factors, so as to obtain a number or a vector of numbers for each scale ("multi-scale analysis"), which are then concatenated to make a composite vector of numbers ("multi-scale descriptors").

Oriented Morphological Filterbank Descriptors:

At each scale $s_k$ the oriented morphological filtered images are computed using structuring elements (geometric shapes) that resemble elongated structures, such as rectangles, ellipse, or the like. These filters are applied at different orientations representing angular steps of $\Delta\theta$. Two different parameters of the structuring element (for example, length and width in case of a rectangular structuring element) are used to compute two morphological filtered images at each orientation. Taking the difference of these two images gives us the quantity of interest at each pixel, which then forms part of the said oriented morphological filterbank descriptors. In one embodiment, median filters are used as the said morphological filter. In this embodiment, at each scale $s_k$ the oriented median normalized images $I_{Norm,\mathcal{R}}^{s_k}$ are computed (for example, using Equation 1) with medians computed within rectangular area $\mathcal{R}$ of length l and width w at angular steps of $\Delta\theta$. In one embodiment, length l=30 and width w=2, and angular steps of $\Delta\theta=15$ degrees are used. At each scale $s_k$ the median normalized images $I_{Norm,\mathcal{C}}^{s_k}$ are computed (for example, using Equation 1) with medians computed within circle $\mathcal{C}$ of radius r. In one embodiment, a radius of r=3 is used.

$$I_{diff}^{s_k} = I_{Norm,\mathcal{R}}^{s_k} - I_{Norm,\mathcal{C}}^{s_k}$$

Oriented median filterbank descriptor is $I_{diff}^{s_k}(x_{int}, y_{int})$ at the different orientations. These descriptors can distinguish elongated structures from blob-like structures. The maximum or minimum value of the filterbank vector is identified and the vector elements are rearranged by shifting each element by P positions until the said maximum or minimum value is in the first position, while the elements going out of the vector boundary are pulled back into the first position sometimes referred to as circular shifting.

In one embodiment, the oriented morphological filterbank descriptors are computed employing the following:

a. Computing morphological filtered image with the morphological filter computed over a circle or regular polygon ("structuring element" of the median filter)

b. Computing another morphological filtered image with the morphological filter computed over a geometric shape elongated structure, such as a rectangle of specified aspect ratio (width, height) and orientation (angle) or an ellipse of specified foci and orientation (angle) of its principal axis c. Computing the difference image between the morphological filtered images computed in (a) and in (b), and assign the difference image value at a given pixel as its descriptor.

d. Computing a vector of numbers ("oriented median descriptors") by (a) varying the orientation angle of the elongated structure and obtaining one number each for each orientation angle, and (b) stacking thus computed numbers into a vector of numbers.

In one embodiment, the maximum or minimum value of the oriented morphological filterbank descriptor vector is identified and the vector elements are rearranged by shifting each element by P positions until the said maximum or minimum value is in the first position, while the elements going out of the vector boundary are pulled back into the first position ("circular shifting").

In one embodiment, these descriptors are evaluated on a set of images obtained by progressively resizing the original image up and/or down by a set of scale-factors, so as to obtain a number or a vector of numbers for each scale ("multi-scale analysis"), which are then concatenated to make a composite vector of numbers ("multi-scale descriptors").

Gaussian Derivatives Descriptors:

Median normalized difference image is computed with radii $r_h$ and $r_l$, such that $r_h > r_l$ at each scale $s_k$.

$$I_{diff}^{s_k} = I_{Norm, r_h}^{s_k} - I_{Norm, r_l}^{s_k}$$

The difference image $I_{diff}^{s_k}$ is then filtered using Gaussian filters G.

$$F_0 = I_{diff}^{s_k} * G$$

The image after filtering with second derivative of the Gaussian is also computed.

$$F_2 = F_0''$$

The Gaussian derivative descriptors are then $F_0(x_{int}, y_{int})$ and $F_2(x_{int}, y_{int})$. These descriptors are useful in capturing circular and ring shaped lesions (for example, microaneurysms).

Hessian-Based Descriptors:

Median normalized difference image with bright vessels is computed with radii $r_h$ and $r_1$, such that $r_h > r_l$ at each scale $s_k$.

$$I_{diff}^{s_k} = I_{Norm, r_l}^{s_k} - I_{Norm, r_h}^{s_k}$$

Then, Hessian H is computed at each pixel of the difference image $I_{diff}^{s_k}$. Determinant of Hessian map $L_{|H|}$ of the difference image $I_{diff}^{s_k}$ is the map of the determinant of Hessian H at each pixel. The sum modified Laplacian is computed to describe the local image focus. Vesselness and structureness may be computed, for example, as shown in FIG. 22. The Eigen values $\lambda_1$ and $\lambda_2$ of H, such that $|\lambda_1\lambda_2|\leq\lambda_2$ and their ratio $|\lambda_1|/\lambda_2$, are evaluated. The Hessian based descriptor vector is collated from these values at the interest pixel locations ($X_{int}$, $Y_{int}$). These describe local image characteristics of blobs and tubes, such as local sharpness.

Blob Statistics Descriptors:

Using the interest regions mask $Z_{col}^{s_k}$ computed at scale $s_k$, the region properties listed in are measured at each blob. The interest pixels within a particular blob region are assigned with the same blob statistics descriptor.

Table 4 is one embodiment of blob properties used as descriptors.

TABLE 4

| Blob property | Description |
| --- | --- |
| Area | Number of pixels in the blob region |
| Filled Area | Number of pixels in the filled region |
| Perimeter | Perimeter of the blob which approximates the contour as a line through the centers of border pixels using a 4-connectivity |

TABLE 4-continued

| Blob property | Description |
|---|---|
| Extent | Ratio of pixels in the blob region to pixels in the total bounding box for the blob |
| Eccentricity | Eccentricity of the ellipse that has the same second-moments as the region. |
| Maximum intensity | Value of greatest intensity in the blob region |
| Minimum intensity | Value of lowest intensity in the blob region |
| Average intensity | Value of mean intensity in the blob region |

Color Descriptors:

Average color is measured in a square block of length 1 centered at the pixel of interest. The color in RGB space is used as the color descriptor for the pixel. In one embodiment, smoothing square of length l=5 is used.

Filterbank of Fourier Spectral Descriptors:

The natural logarithm of the Fourier transform magnitude and first derivative of Fourier transform phase of a patch of image $\mathcal{B}$ centered at the pixel of interest at various frequencies are computed. These descriptors are invariant to rotation and scaling and can survive print and scanning. The natural logarithm of Fourier transform magnitude of the image patch can be computed as follows:

$$F_1(\omega) = \ln(|\mathcal{F}_\omega(\mathcal{B})|)$$

$$F_2(\omega) = d(\phi(\mathcal{F}_\omega)(\mathcal{B})))/d\omega$$

where $F_1(\omega)$ and $F_2(\omega)$ are the fourier spectral descriptors, $\mathcal{F}_\omega$ is the fourier transform operation at frequency $\omega$ and $\phi$ denotes phase.

Localized Gabor Jets Descriptors:

Gabor jets are multi resolution Gabor features, constructed from responses of multiple Gabor filters at several frequencies and orientations. Gabor jet descriptors are computed as follows:

$$G(x, y, \lambda, \psi, \sigma, \gamma) = \exp\left(-\frac{x'^2 + \gamma^2 y'^2}{2\sigma^2}\right) \cos\left(2\pi \frac{x'}{\lambda} + \psi\right)$$

where, $$x' = x \cos(\theta) + y \sin(\theta)$$

$$y' = -x \sin(\theta) + y \cos(\theta)$$

$\lambda$ is the wavelength of the sinusoidal factor, $\theta$ is the orientation of the normal to the striping of the Gabor function, $\psi$ is the phase offset, $\sigma$ is the standard deviation of the Gaussian envelope and y is the spatial aspect ratio.

Filterbank of Matched Filters:

2D Gaussian filter is used as a kernel for multi-resolution match filtering. Gaussian filters of a range of sigmas are used as the filterbank as follows:

$$G(x, y, \sigma) = \exp\left(-\frac{x'^2 + y'^2}{2\sigma^2}\right)$$

Path Opening and Closing Based Morphological Descriptors Filterbank:

Path opening and closing based morphological descriptors use flexible line segments as structuring elements during morphological operations. Since these structuring elements are adaptable to local image structures, these descriptors may be suitable to describe structures such as vessels.

Filterbank of Local Binary Patterns Descriptors:

Local binary patterns (LBP) capture texture information in images. In one embodiment, a histogram with 20 bins to describe the LBP images is used.

c. Lesion Classification

In one embodiment, a support vector machine (SVM) is used for lesion classification. In other embodiments, classifiers such as k-nearest neighbor, naive Bayes, Fisher linear discriminant, deep learning, or neural networks can be used. In another embodiment, multiple classifiers can be used together to create an ensemble of classifiers. In one embodiment, four classifiers—one classifier for each of cottonwoolspots, exudates, hemorrhages, and microaneurysms—are trained and tested. In one embodiment, ground truth data with lesion annotations on 100 images is used for all lesions, plus more than 200 images for microaneurysms. The annotated dataset is split in half into training and testing datasets, and interest region detector is applied on the training dataset images. The detected pixels are sampled such that the ratio of the number of pixels of a particular category of lesion in the training dataset to those labeled otherwise remains a constant referred to as the balance factor B. In one embodiment, B=5 for cottonwoolspots, exudates, and hemorrhages classifiers, and B=10 for microaneurysms.

In one embodiment, interest region detector is applied on the testing dataset images. The detected pixels are classified using the 4 different lesion classifiers noted above. Each pixel then has 4 decision statistics associated with it. A decision statistic for a particular pixel is generated by computing the distance of the given element from the given lesion classification hyper plane defined by the support vectors in the embodiment using SVM for lesion classification or in the embodiment using Fisher linear discriminant or the like. In case of the embodiment using a naive Bayes classifier or the embodiment using the k-nearest neighbor, the class probability for lesion class and non-lesion class are computed and are used as the decision statistic.

d. Joint Recognition-Segmentation

Figures 26A, 26B, 26C:
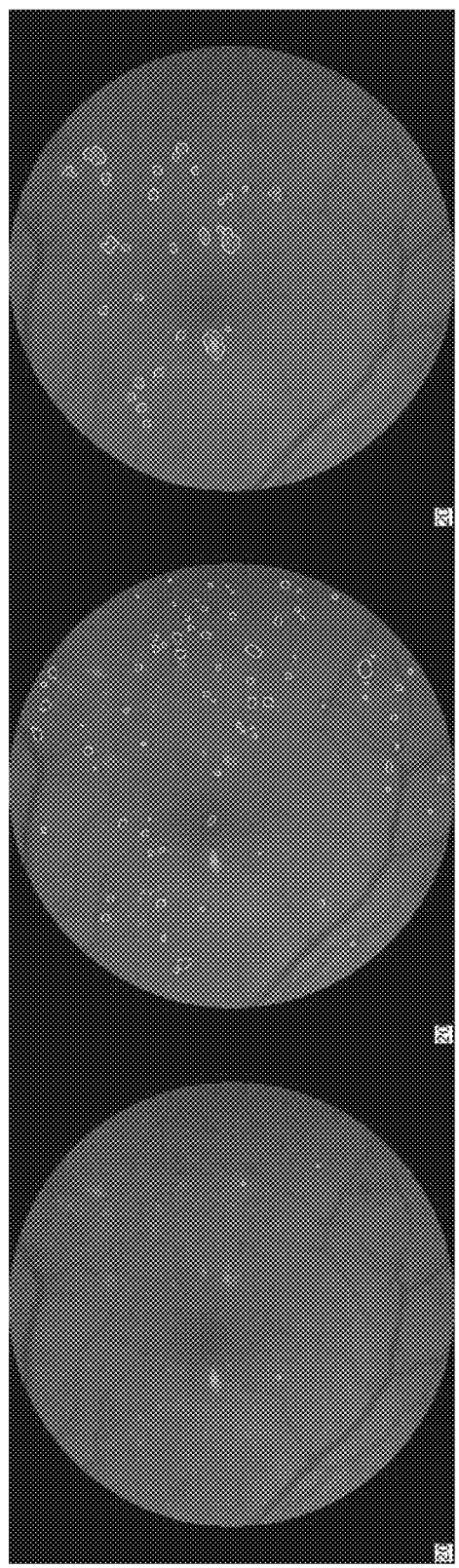
FIG. 26A shows one embodiment of an example of microaneurysms localization.
FIG. 26B shows one embodiment of an example of hemorrhages localization.
FIG. 26C shows one embodiment of an example of exudates localization.
Figure 27:
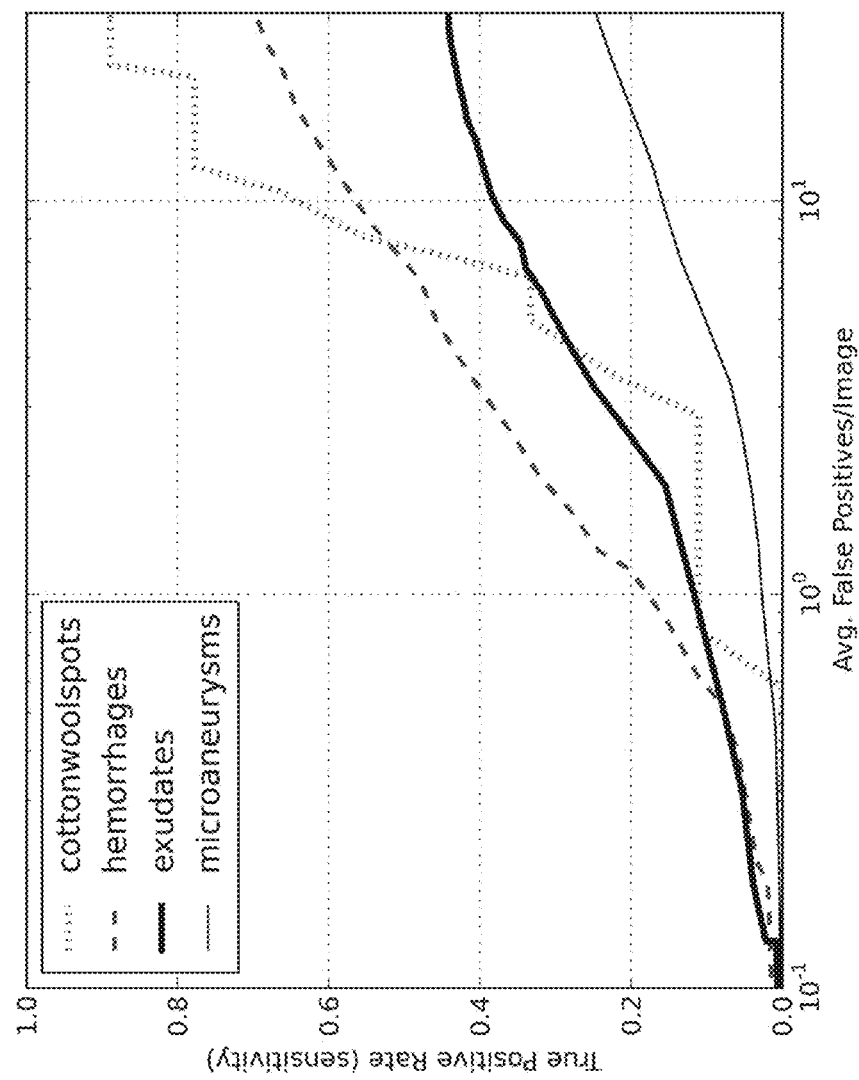
FIG. 27 shows one embodiment of a graph demonstrating performance of one embodiment of the lesion localization module in terms of free response ROC plots for lesion detection.

In one embodiment, a biologically-inspired framework is employed for joint segmentation and recognition in order to localize lesions. Segmentation of interest region detector outputs the candidate lesion or non-lesion blobs. The decision statistic output from pixel-level classifiers can provide evidence to enable recognition of these lesions. These decision statistics from different pixels and different lesion types are pooled within each blob to arrive at a blob-level recognition. The pooling process may include computing the maximum, minimum or the average of decision statistics for a given lesion type for all the pixels in a given blob. This process can be repeated iteratively, although in some embodiments, a single iteration can be sufficient. FIG. 26A shows an example embodiment of microaneurysm localization. FIG. 26B shows an example embodiment of hemorrhages localization. FIG. 26C shows an example of exudates localization. FIG. 27 illustrates one embodiment of a graph that quantifies the performance of lesion detection.

In another embodiment, the pixel level decision statistics over each blob and building secondary descriptors can be combined. Secondary descriptors can be one or more of the following:

Average value of the pixel decision statistics;

Bag of words (BOW) descriptors aggregated at blob level; or

Histogram of pixel decision statistics.

These aggregated descriptors can then be used to train blob-level lesion classifiers and can be used to recognize and/or segment lesions. These descriptors can also be used for screening.

E. Lesion-Based Biomarkers

1. Lesion Dynamics

Some embodiments pertain to computation of lesion dynamics, which quantifies changes in the lesions over time.

Figure 28:
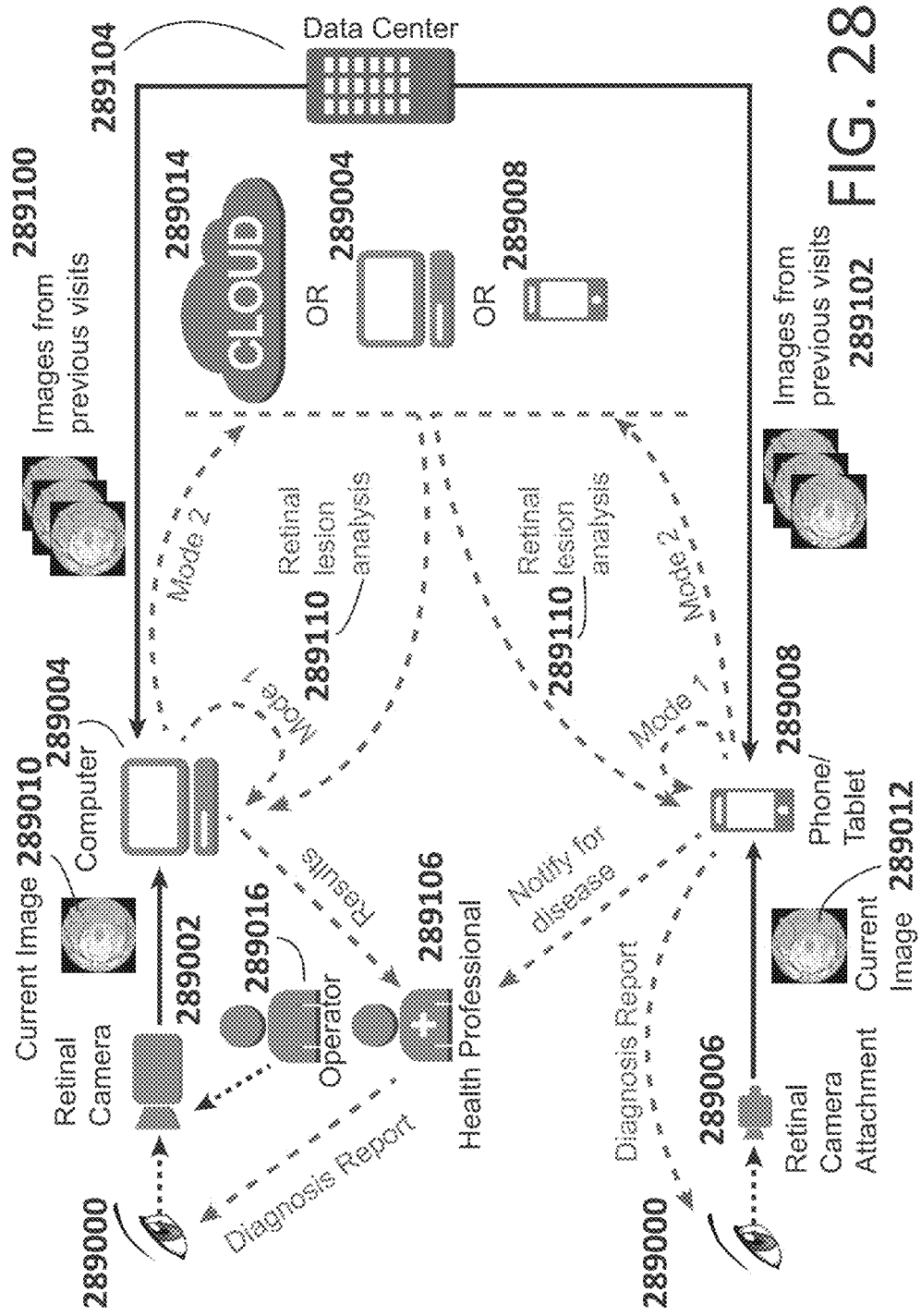
FIG. 28 illustrates various embodiments of a lesion dynamics analysis system and process.

FIG. 28 shows various embodiments of a lesion dynamics analysis system and process. The patient 289000 is imaged by an operator 289016 using an image capture device 289002. In this embodiment, the image capture device is depicted as a retinal camera. The current image captured 289010 is sent to the computer or computing device 289004. Images from previous visits 289100 can be obtained from a datacenter 289104. Lesion dynamics analysis 289110 is performed on the same computer or computing device 289004, on the cloud 289014, a different computer or computing device 289004, a mobile device 289008, or the like. The results are received by computer 289004 and then sent to a healthcare professional 289106 who can interpret the results and report the diagnosis to the patient. In one embodiment, the patient 289000 can take the image 289012 himself using an image capture device 289006, for example, a retinal camera attachment for a mobile device 289008. The images from previous visits 289102 are downloaded to the mobile device from the datacenter 289104. Lesion dynamics analysis is performed on the mobile device, on the cloud 289014, or a computer or computing device 289004, on a different mobile device, or the like. The results of the analysis are provided to the mobile device 289008, which performs an initial interpretation of the results and presents a diagnosis report to the patient. The mobile device 289008 can also notify the health professional if the images contain any sign of disease or items of concern.

Figure 29A:
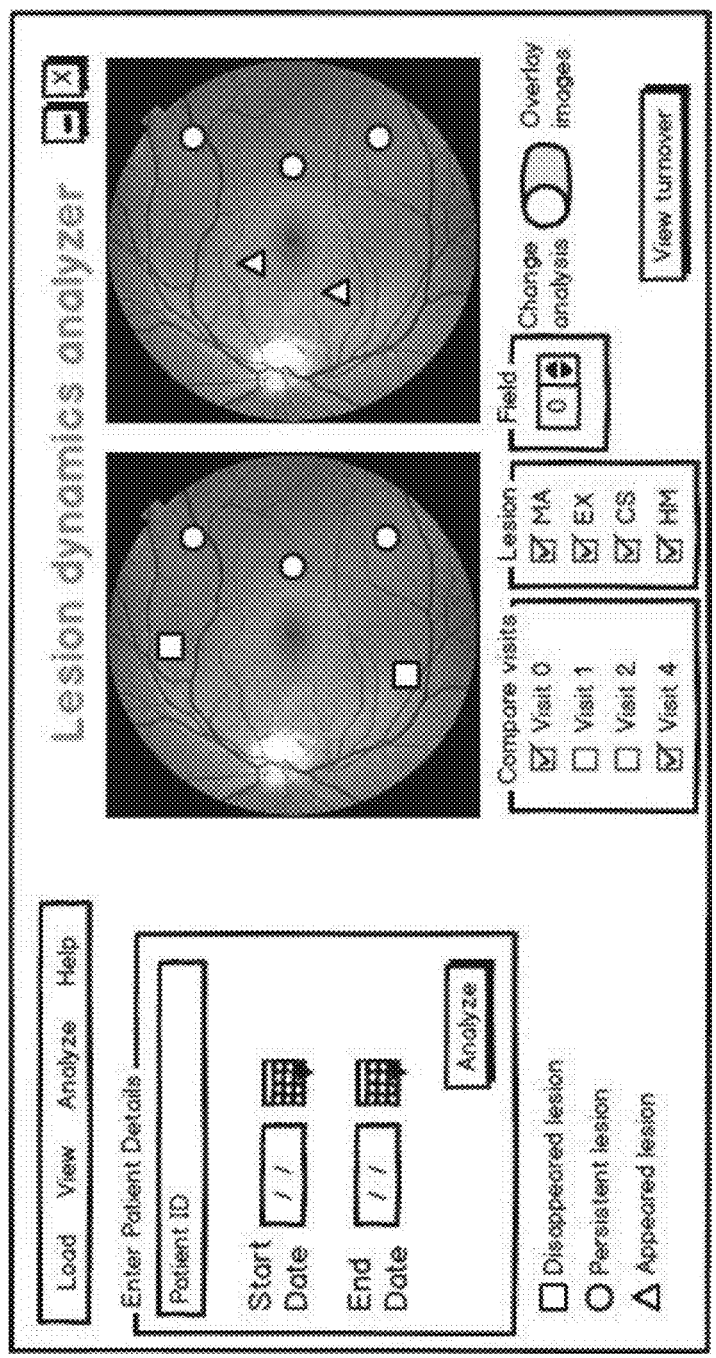
FIG. 29A depicts an example of one embodiment of a user interface of a tool for lesion dynamics analysis depicting persistent, appeared, and disappeared lesions.
Figure 29B:
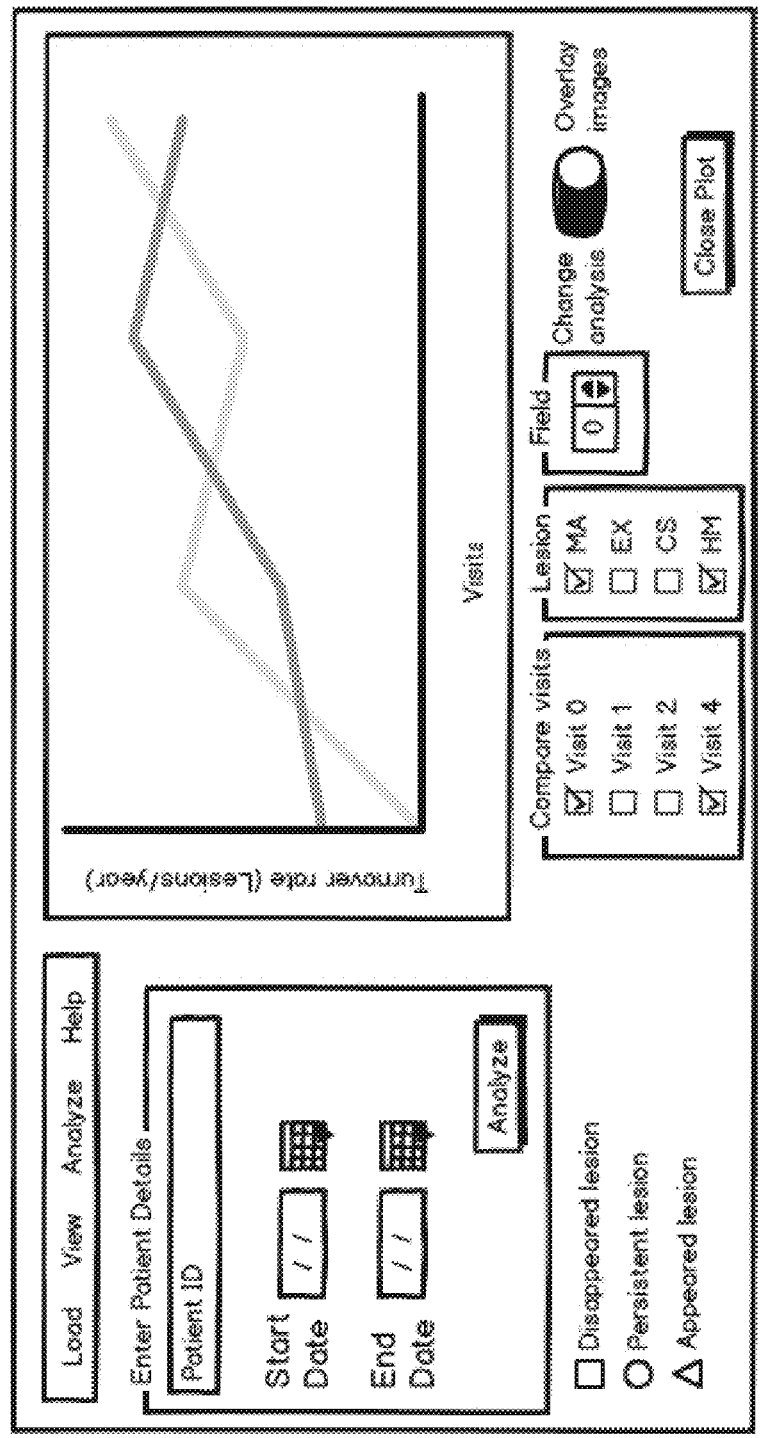
FIG. 29B depicts an example of one embodiment of a user interface of a tool for lesion dynamics analysis depicting plots of lesion turnover.
Figure 29C:
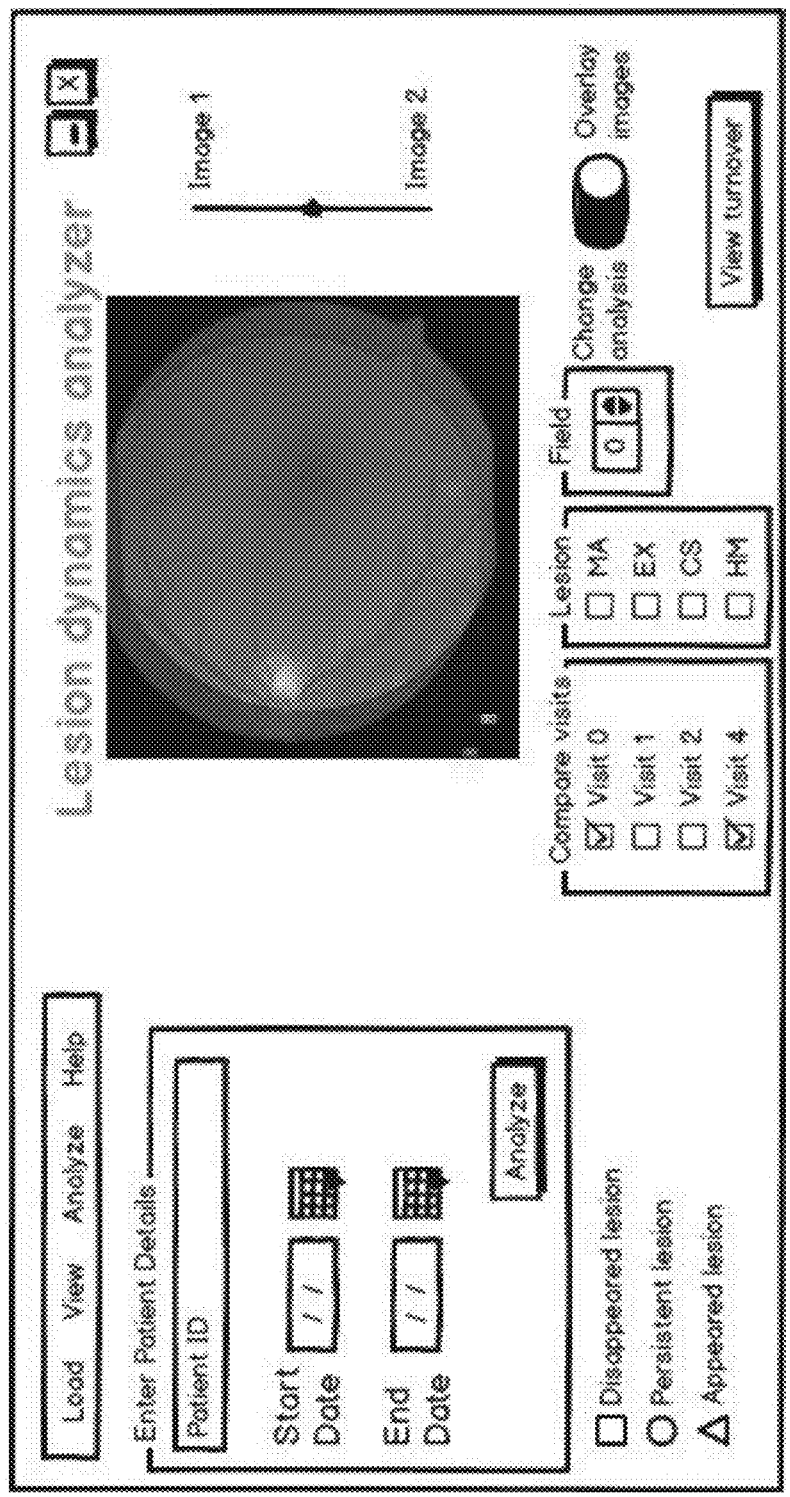
FIG. 29C depicts an example of one embodiment of a user interface of a tool for lesion dynamics analysis depicting overlay of the longitudinal images.

FIG. 29A depicts an example of one embodiment of a user interface of the tool for lesion dynamics analysis depicting persistent, appeared, and disappeared lesions. The user can load the images from a database by inputting a patient identifier and range of dates for analysis. As depicted in the embodiment shown in FIG. 29B, when the user clicks on "View turnover," the plots of lesion turnover for the chosen lesions are displayed. As depicted in the embodiment shown in FIG. 29C, when the toggle element to change from using the analysis to viewing the overlaid images is utilized, longitudinal images for the selected field between the selected two visits are shown. The user can change the transparency of each of the image using the vertical slider.

In one embodiment, longitudinal retinal fundus images are registered to the baseline image as described in the section above entitled "Image Registration". On each of the images, including the baseline image, lesions are localized as described in the section above entitled "Lesion Localization". In some embodiments, characterizing dynamics of lesions such as exudates (EX) and microaneurysms (MA) may be of interest. In one embodiment, the appearance and disappearance of MA, also referred to as MA turnover is considered. The first image in the longitudinal series is referred to as the baseline image $I_b$ and any other registered longitudinal image is denoted as $I_1$.

Figure 30:
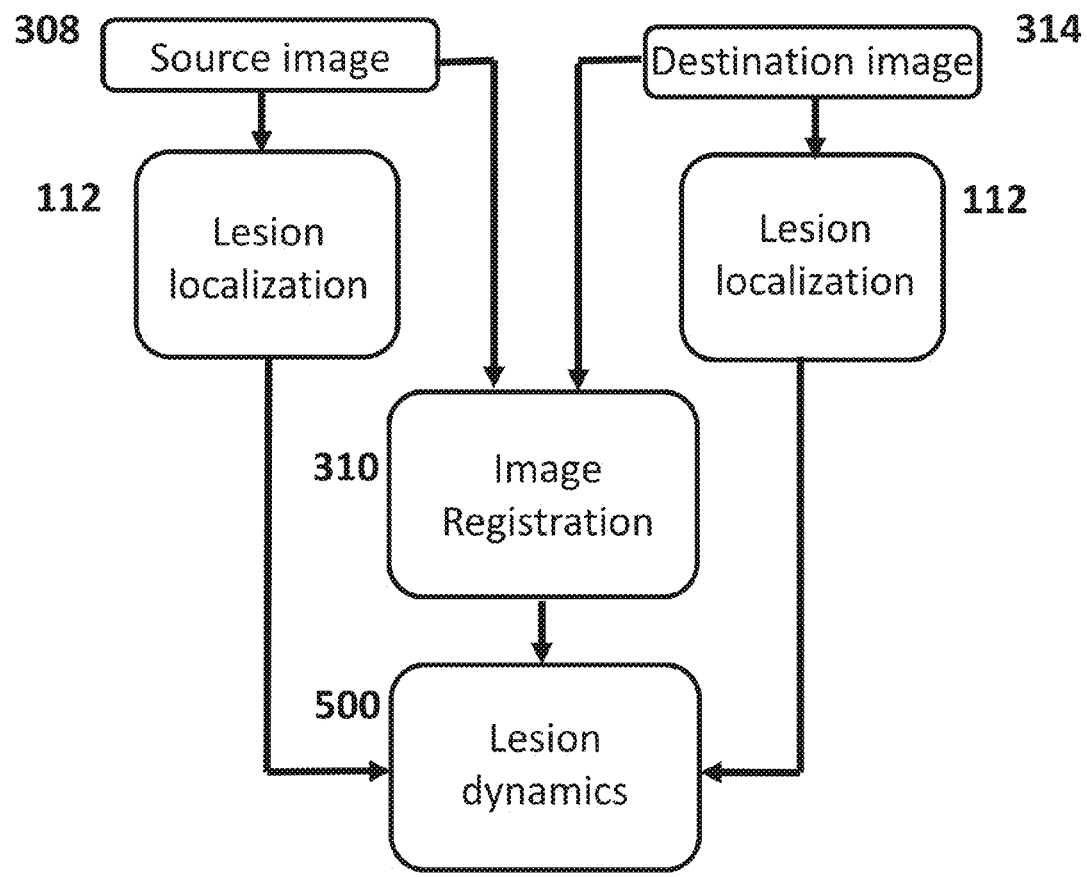
FIG. 30 is a block diagram of one embodiment for evaluating longitudinal changes in lesions.

FIG. 30 illustrates an embodiment used in evaluating lesion dynamics. The blocks shown here can be implemented on the cloud 289014, a computer or computing device 289004, a mobile device 289008, or the like as, for example, shown in FIG. 28. The input source image 308 and destination image 314 refer to a patient's retinal data, single or multidimensional, that has been captured at two different times using a retinal imaging device, such as cameras for color image capture, fluorescein angiography (FA), adaptive optics, optical coherence tomography (OCT), hyperspectral imaging, scanning laser ophthalmoscope (SLO), wide-field imaging or ultra-wide-field imaging. Image 100 is input into the lesion localization module 112. FIG. 13A illustrates an embodiment of the image registration block 310. Lesion dynamics module 500 computes changes in lesions across retinal images imaged at different times. Lesion changes can include appearance, disappearance, change in size, location, or the like.

a. Lesion Matching For MA Turnover Computation

In one embodiment, binary images $B_b$ and $B_1$ with lesions of interest marked out are created for the baseline and longitudinal images. Lesion locations are labeled in $B_b$ and compared to the corresponding regions in $B_1$ with a tolerance that can, for example, be specified by maximum pixel displacement due to registration errors. The labeled lesion is marked as persistent if the corresponding region contains a MA, else it is marked as a disappearing MA. Labeling individual lesions in $B_1$ and comparing them to corresponding regions in $B_b$ gives a list of newly appeared lesions. FIGS. 31A, 31B, 31C and 31D depict embodiments and examples of longitudinal images for comparison to identify persistent, appeared and disappeared lesions. The images are zoomed to view the lesions. FIG. 31A shows the baseline image. FIG. 31B shows the registered longitudinal image. FIG. 31C shows labeled MAs in the baseline image with persistent MAs indicated by ellipses and non-persistent MAs by triangles. FIG. 31D shows labeled MAs in the longitudinal image with persistent MAs indicated by ellipses. Counting the newly appeared lesions and disappeared lesions over the period of time between the imaging sessions allows computation of lesion turnover rates, or MA turnover if the lesion under consideration is MA.

In another embodiment, the baseline image $I_b$ and registered longitudinal image $I_1$ are used rather than the registered binary lesion maps. Potential lesion locations are identified using the interest region detector as, for example, described in the section above entitled "Interest Point Detection". In one embodiment, these pixels are then classified using lesion classifier, for example, as described in the lesion localization section using, for example, descriptors listed in Table 3. The regions with high certainty of including lesions in $I_b$, as expressed by the decision statistics computed over the pixels, are labeled. In one embodiment, these regions are then matched with corresponding regions in $I_1$ with a tolerance, for example, as specified by maximum pixel displacement which may be due to registration errors using decision statistics. In one embodiment, regions with matches to the labeled lesions with high confidence are then considered to be persistent lesions, and labeled regions with no matches are considered to be disappeared lesions. Newly appearing lesions can be found by labeling image $I_1$ and comparing those regions to corresponding regions in $I_b$ to identify newly appearing lesions.

b. Increased Reliability and Accuracy In Turnover Computation

Figures 33A, 33B, 33C:
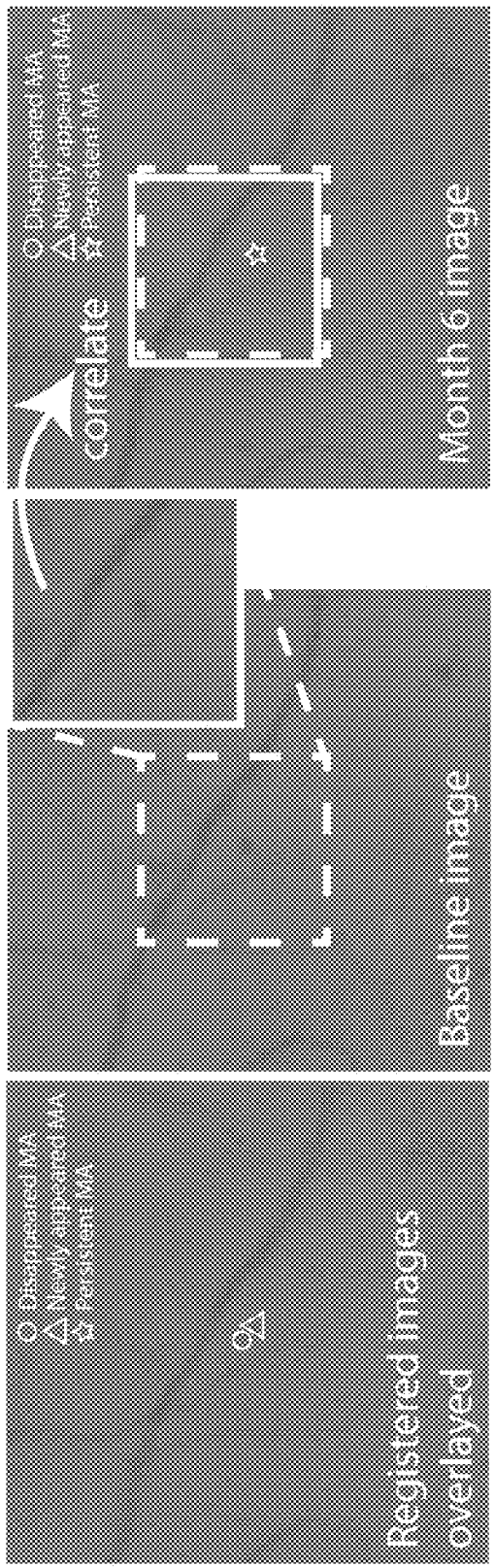
FIG. 33A shows embodiments of local registration refinement with baseline and month 6 images registered and overlaid.
FIG. 33B shows embodiments of local registration refinement with baseline image, and enhanced green channel when the dotted box shows a region centered on the detected microaneurysm, and with an inset showing a zoomed version.
FIG. 33C shows embodiments of local registration refinement with a month 6 image, enhanced green channel, the new lesion location after refinement correctly identified as persistent.

Some factors can confound lesion turnover computation such as MA turnover computation, variation in input images, errors in image alignment, or errors in MA detection and localization. Some errors can cascade and cause the MA turnover computed to be drastically different from the actual value, which could be a failure for the tool. In some embodiments, a system that gracefully degrades when faced with the above confounding factors is desirable. At each stage, rather than making a binary decision, the probability that a blob is classified as an MA or the probability that two blobs are marked as matched MAs and hence persistent is estimated. As noted above, a blob includes a group of pixels with common local image properties and chosen by the interest region detector. FIG. 32A shows a patch of retina with microaneurysms. FIG. 32B shows the ground truth labelling for microaneurysms in the image patch shown in FIG. 32A. FIG. 32C shows the detected MAs marked by disks with the corresponding confidence levels indicated by the brightness of the disk. An estimated range for MA turnover is computed rather than a single number. A larger range may represent some uncertainty in the turnover computation, nevertheless it can provide the clinician with useful diagnostic information. In one embodiment, one or more of the following is performed when confounding factors are present.

i. Handling quality variations in input image: The quality of the input images can vary as they are images at different time, possibly using different imaging systems and by different operators. The quality of the image can be inferred locally. The quality of the sections of the image can be used as a weight to infer confidence in MA detection along with the classifier decision statistic.

ii. Local registration refinement for global image alignment error correction: Registration errors can occur due to lack of matching keypoints between images. Local refinement of registration using a small image patch centered on the putative microaneurysm can be used to correct these errors. FIG. 33A shows baseline and Month 6 images registered and overlaid. Misalignment causes persistent MA to be wrongly identified as disappeared and appeared. FIG. 33B shows the baseline image, as grayscale image of the enhanced green channel only. The dotted box shows region centered around the detected MA, with inset showing zoomed version. FIG. 33C shows Month 6 image, as grayscale image of the enhanced green channel only. The dotted region around MA in FIG. 33B is correlated with the image shown in FIG. 33C to refine the registration. The dotted box in FIG. 33C corresponds with the box in FIG. 33B, and the solid box in FIG. 33C indicates the new location after refinement. MA is now correctly identified as persistent. When the local patches are aligned, the putative microaneurysms are then matched to evaluate persistent MAs.

iii. Robust persistent microaneurysm classification: Probabilities can be used to represent the classification of a given blob into microaneurysm or otherwise. Persistent MAs are marked in the ground truth representation and will describe pairs of blobs with the histogram decision statistics of the pixels in the blobs along with similarity of the blobs. The labeled persistent MAs can be used to train a SVM classifier. Given a pair of putative blobs in the neighborhood after local registration refinement, the probability that these blobs are a persistent MA pair is computed.

Figure 34B:
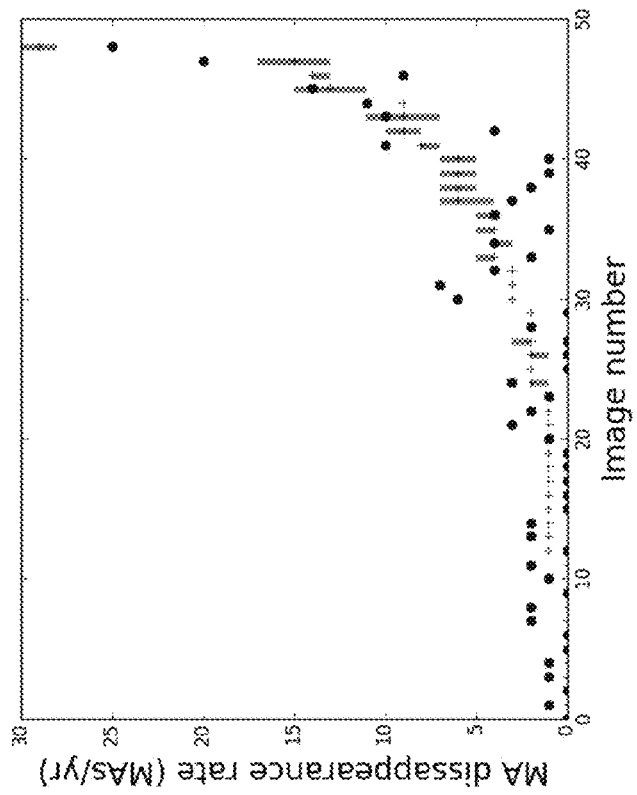
FIG. 34B shows embodiments of microaneurysms turnover (or disappearance) rates ranges, number of MAs per year, computed (in gray), and ground truth values (black circles) for various images in a dataset.
Figure 34A:
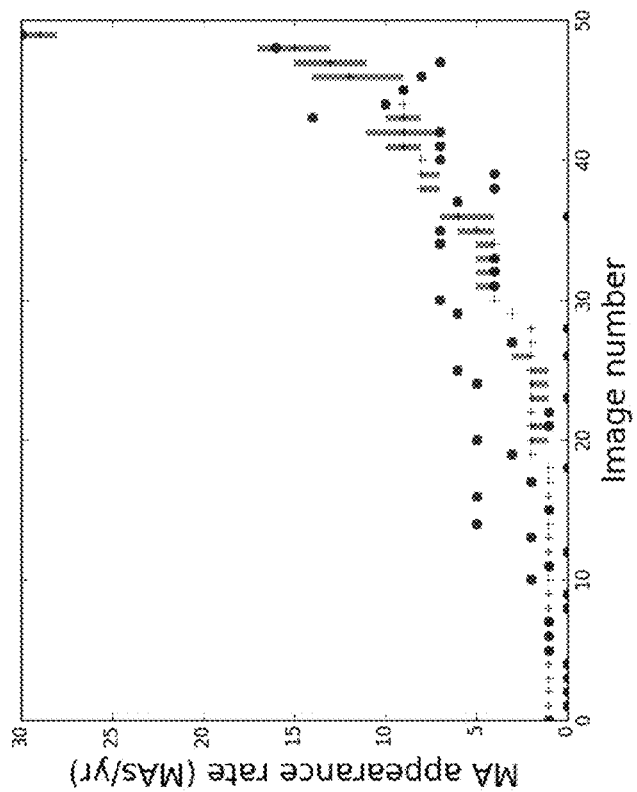
FIG. 34A shows embodiments of microaneurysms turnover (or appearance) rates ranges, number of MAs per year, computed (in gray), and ground truth values (black circles) for various images in a dataset.

As shown in embodiments of FIGS. 34A and 34B, the range for turnover numbers is then assessed from the blob level probabilities and persistent MA pair probabilities using thresholds identified from the ground truth.

F. Encounter-Level Processing Framework

Medical and retinal images captured during a given visit of a given patient are typically captured using the same imaging set-up. The set of these images is termed an encounter (of that patient on that date). The analysis of the images in a given encounter can be performed jointly using data from all the images. For example, the presence or absence of lesions in one eye of a given patient can be determined after examining all the images captured of that eye.

In one embodiment, a method for identifying abnormal medical (particularly retinal) images using one or at least two or more images obtained from the same patient in the same visit ("encounter"), the method can include one or more of the following:

a. Identifying a subset of images for further analysis based on image quality, image content, such as the image being a lens shot or a non-retinal image, or of poor quality or fidelity;

b. For each image identified in (a) designating some pixels in the image as active pixels, meaning they contain the interesting regions of the image, using of one or more techniques from (i) conditional number theory, (ii) multi-scale interest region detection, (iii) vasculature analysis, and (iv) structured-ness analysis;

c. For each image identified in (a), computing a vector of numbers ("primary descriptors") at each of the pixels identified in (b) using one or at least two or more types from (i) median filterbank descriptors, (ii) oriented median filterbank descriptors, (iii) Hessian based descriptors, (iv) Gaussian derivatives descriptors, (vi) blob statistics descriptors, (vii) color descriptors, (viii) matched filter descriptors, (ix) path opening and closing based morphological descriptors, (x) local binary pattern descriptors, (xi) local shape descriptors, (xii) local texture descriptors, (xiii) local Fourier spectral descriptors, (xiv) localized Gabor jets descriptors, (xv) edge flow descriptors, (xvi) edge descriptors such as difference of Gaussians, (xvii) focus measure descriptors such as sum modified Laplacian, (xix) saturation measure descriptors, (xx) contrast descriptors, or (xxi) noise metric descriptors;

d. For each image, for each pixels identified in (b), computing pixel-level classifier decision statistic (a number quantifying the distance from the classification boundary) using supervised learning utilizing the primary descriptors computed in (c) using one or more of (i) support vector machine, (ii) support vector regression, (iii) k-nearest neighbor, (iv) naive Bayes, (v) Fisher linear discriminant, (vi) neural network, (vii) deep learning, (viii) convolution networks, or (ix) an ensemble of one or more classifiers including from (i)-(viii), with or without bootstrap aggregation;

e. For each image identified in (a), computing a vector of numbers ("image-level descriptors") by using one or least two or more types from:
  i. histogram of pixel-level classifier decision statistics computed in (d);
  ii. descriptors based on dictionary of codewords of pixel-level descriptors (primary descriptors) computed in (c) aggregated at image level; or
  iii. histogram of blob-level decision statistic numbers (one number per blob) computed as mean, median, maximum, or minimum of pixel-level classifier decision statistics computed in (d) for all pixels belonging to the blob;

f. Combining the image-level descriptors computed in (e) with or without further processing for the subset of images identified in (a) to obtain encounter-level descriptors;

g. Classifying encounters using encounter-level descriptors computed in (f) as normal or abnormal (one classifier each for each abnormality, lesion, or disease) using one or more of supervised learning techniques including but not limited to: (i) support vector machine, (ii) support vector regression, (iii) k-nearest neighbor, (iv) naive Bayes, (v) Fisher linear discriminant, (vi) neural network, (vii) deep learning, (viii) convolution networks, or (ix) an ensemble of one or more classifiers including from (i)-(viii), with or without bootstrap aggregation.

In another embodiment, the combining image-level descriptors into encounter-level descriptors for the images of the patient visit (encounter) identified in (a) is achieved using operations that include but are not limited to averaging, maximum, minimum or the like across each index of the descriptor vector, so that the said encounter-level descriptors are of the same length as the image-level descriptors.

In another embodiment, the combining image-level descriptors for the images of the patient visit (encounter) identified in (a) to obtain encounter-level descriptors is achieved using a method including: (i) combining image-level descriptors to form either the image field-of-view (identified from meta data or by using position of optic nerve head and macula)-specific or eye (identified from meta data or by using position of optic nerve head and macula)-specific descriptors, or (ii) concatenating the field-specific or eye-specific descriptors into the encounter level descriptors.

1. Ignoring Lens Shot Images

Images in an encounter can be identified to be lens shot images, using, for example, the method described in the section above entitled "Lens Shot Image Classification." These lens shot images can be ignored and excluded from further processing and analysis since they may not provide significant retinal information. The images that are not retinal fundus images are ignored in this part of the processing.

2. Ignoring Poor Quality Images

Images in an encounter can be identified as having poor quality using, for example, the method described in the section above entitled "Image Quality Assessment." These poor quality images can be excluded from further processing and analysis since the results obtained from such images with poor quality are not reliable. If a given encounter does not have the required number of adequate/good quality images then the patient is flagged to be re-imaged.

3. Ways Of Creating Encounter-Level Decisions a. Merging image-level primary descriptors Encounter-level descriptors can be obtained by combining image-level primary descriptors, many of which are described in the sections above entitled "Processing That Can Be Used To Locate The Lesions." and "Features that can be used for this type of automatic detection". In one embodiment, the image level descriptors include one or more types from:

i. histogram of pixel-level classifier decision statistics computed;

ii. descriptors based on dictionary of codewords of pixel-level descriptors (primary descriptors) aggregated at image level; or iii. histogram of blob-level decision statistic numbers (one number per blob) computed as mean, median, maximum, or minimum of pixel-level classifier decision statistics computed for pixels belonging to the blob.

In one embodiment, the encounter-level descriptors can be evaluated as the maximum value across all the image level descriptors for the images that belong to an encounter or created by concatenating eye level descriptors. In one embodiment, the computation of encounter-level descriptors for the images of the patient visit (encounter) is achieved using a method comprising (i) combining image-level descriptors to form either the image field-of-view, specific descriptors (identified from metadata or by using position of ONH as described in the section above entitled "Optic Nerve Head Detection" or by using the position of the ONH and macula) or eye-specific descriptors (identified from metadata or position of ONH and macula or the vector from the focus to the vertex of the parabola that approximates the major vascular arch) using operations such as maximum, average, minimum or the like, and (ii) concatenating the field-specific or eye-specific descriptors into the encounter level descriptors. These encounter-level descriptors can then be classified, for example, using classifiers described in the section below entitled "Diabetic Retinopathy Screening" to obtain the encounter-level decisions. Combination of image level descriptors to form encounter level descriptors is discussed in further detail in section "Multi-Level Descriptors For Screening".

b. Merging Image-Level Decision Statistics

Encounter-level decisions can also be made by combining image-level decision statistics histograms using average, maximum, and minimum operations, or the like.

VI. Automated Screening

Methods, systems and techniques described can also be used to automate screening for various medical conditions or diseases, which can help reduce the backlog of medical images that need to be screened. One or more of the techniques described earlier or in the following sections may be used to implement automated screening; however, using these techniques is not required by for every embodiment of automated screening.

A. Screening For Retinal Diseases

Figure 35:
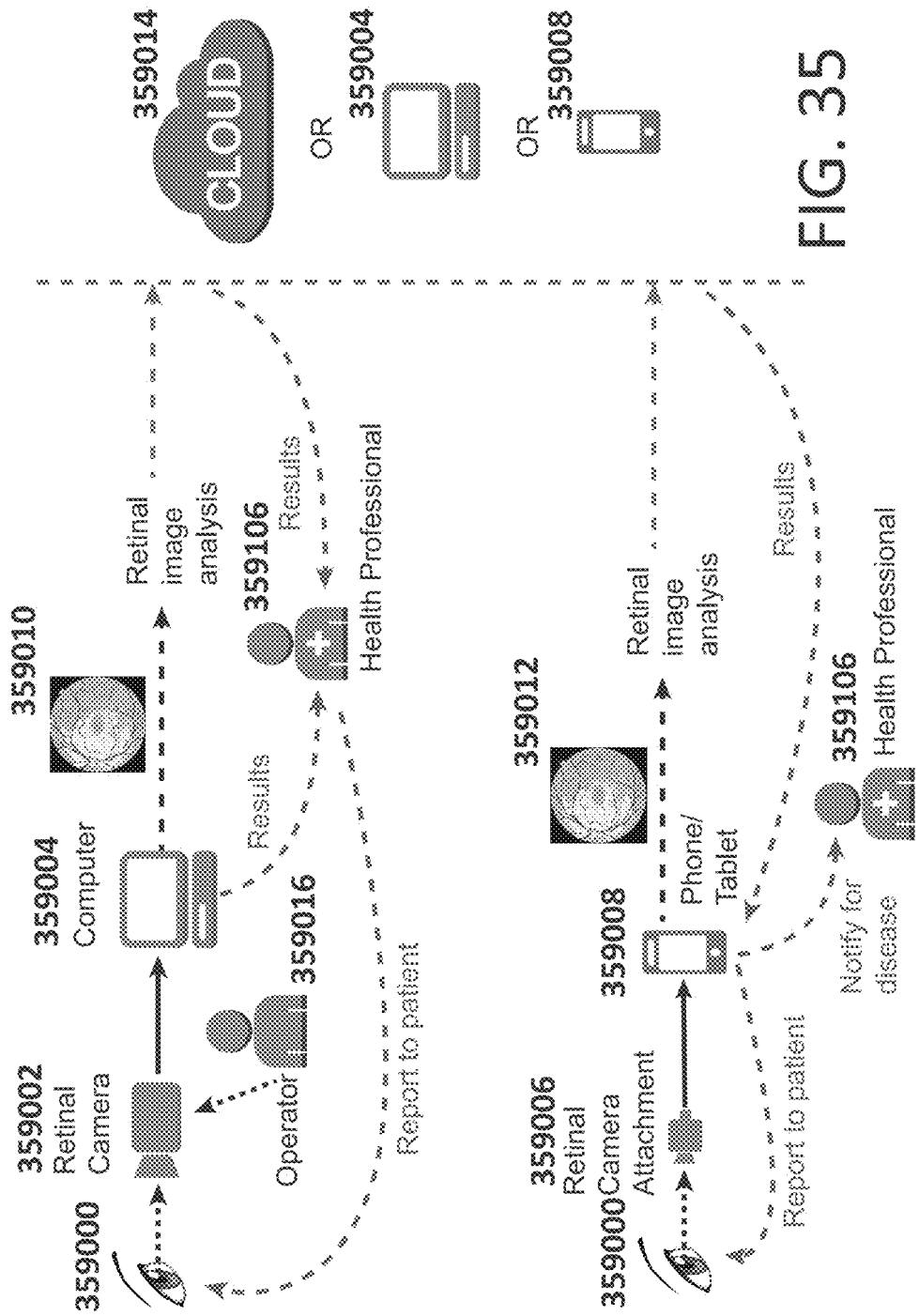
FIG. 35 illustrates various embodiments of an image screening system and process.

FIG. 35 shows one embodiment of scenarios in which disease screening can be applied. In one scenario, the patient 359000 is imaged by an operator 359016 using an image capture device 359002. In the illustrated embodiment, the image capture device is a retinal camera. The images captured are sent to a computer or computing device 359004 for further processing or transmission. In one embodiment all captured images 359010 from the computer or computing device are sent for screening analysis either on the cloud 359014, on a computer or computing device 359004, on a mobile device 359008, or the like. In another embodiment only good quality images 359010 from the computer or computing device are sent for screening analysis either on the cloud 359014, on the computer or computing device 359004, on the mobile device 359008, or the like. The screening results are sent to a healthcare professional 359106 who interprets the results and reports the diagnosis to the patient. In the second scenario, the patient 359000 takes the image himself using an image capture device 359006, which in this case is shown as a retinal camera attachment for a mobile device 359008. All images or just good quality images 359012 from the mobile phone are sent for screening analysis. The results of the analysis are returned to the mobile device, which performs an initial interpretation of the results and presents a diagnosis report to the patient. The mobile device also notifies the health professional if the images contain any signs of disease or other items of concern.

Figure 36A:
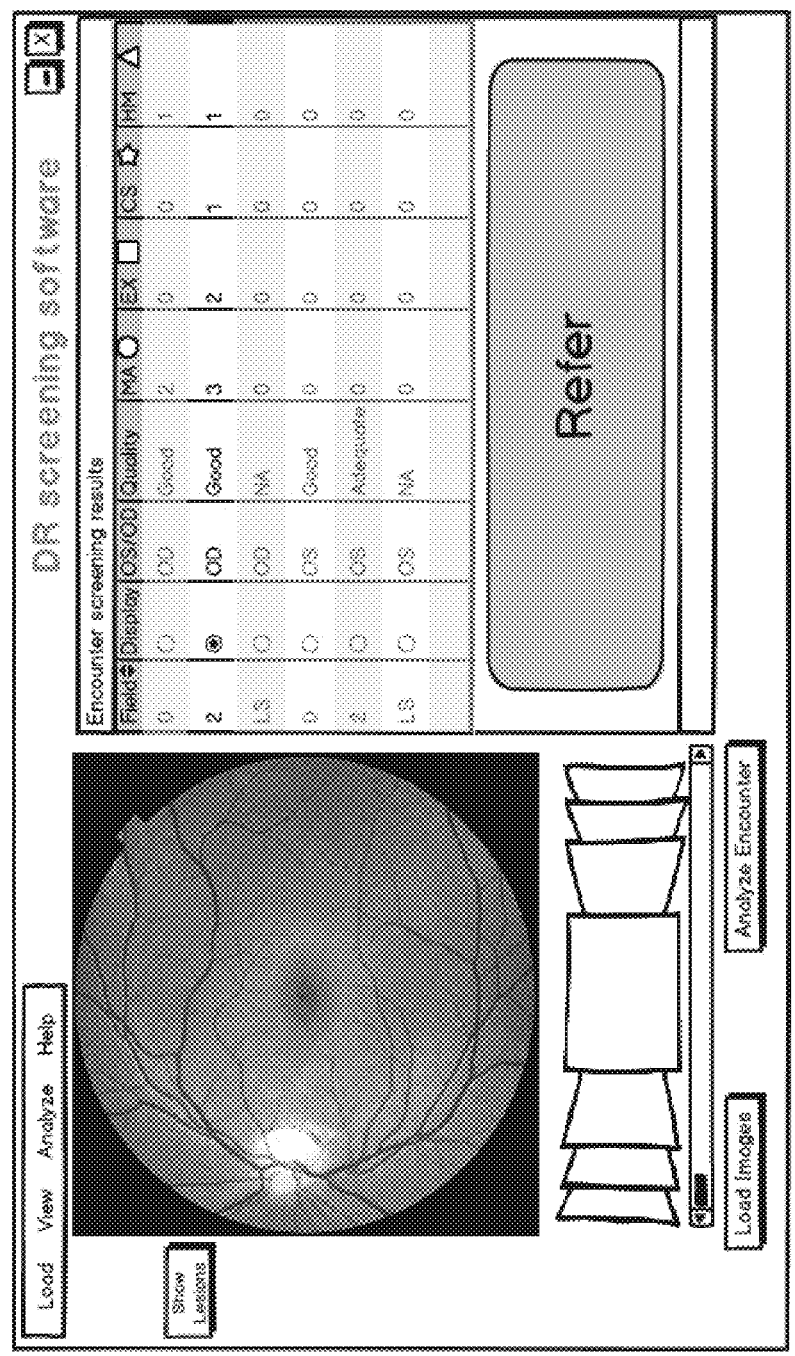
FIG. 36A depicts an example of one embodiment of a user interface of a tool for screening for a single encounter.
Figure 36B:
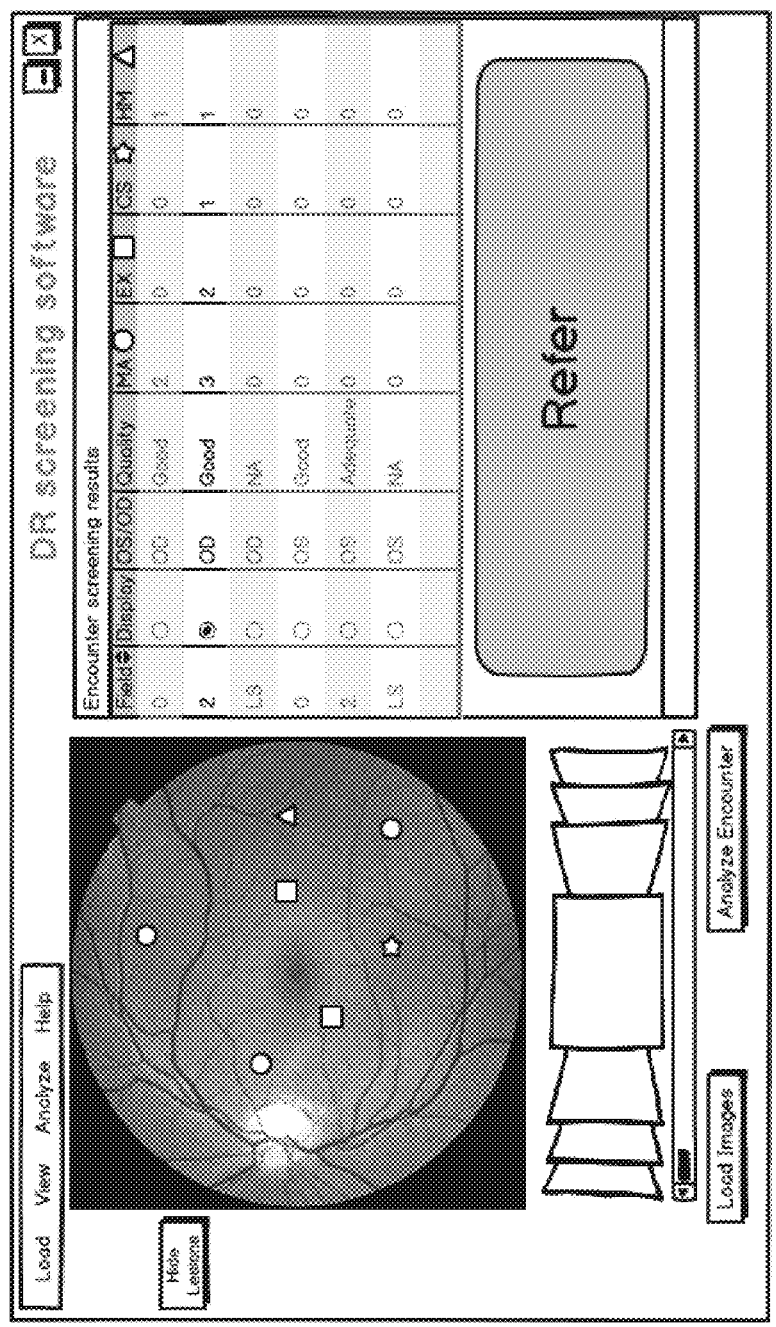
FIG. 36B depicts an example of one embodiment of a user interface of a tool for screening with detected lesions overlaid on an image.
Figure 36C:
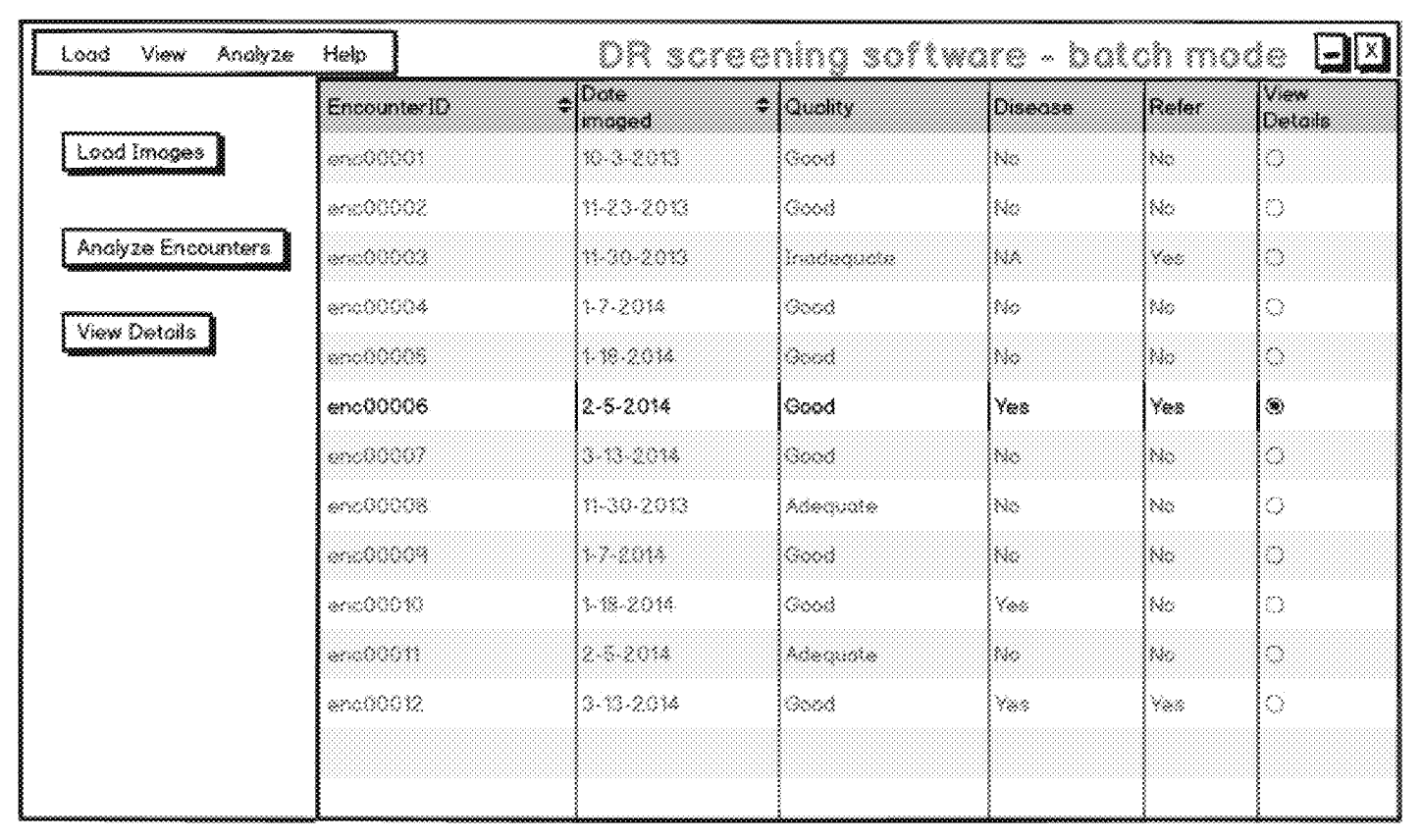
Figure 36D:
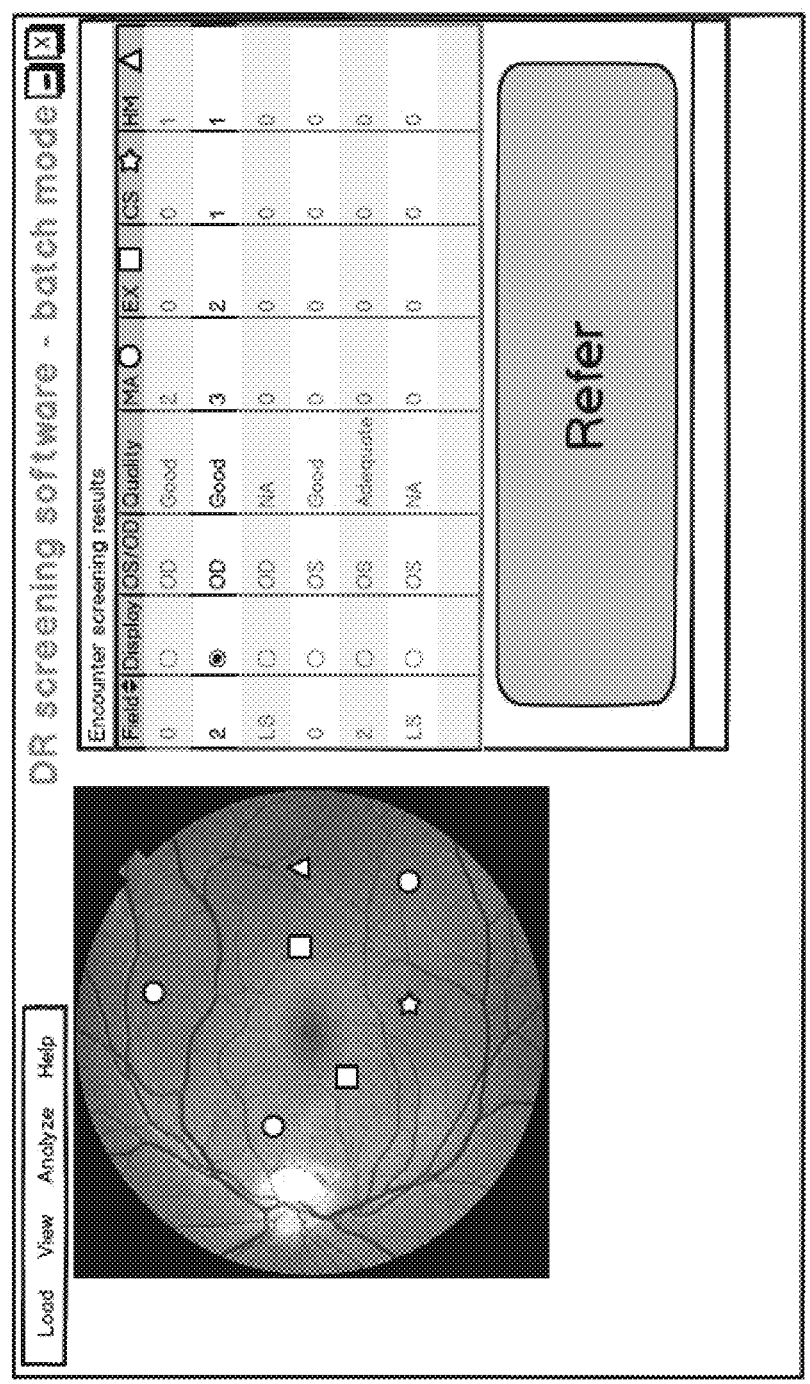
FIG. 36D depicts an example of one embodiment of a user interface of a tool for screening for multiple encounters with detected lesions overlaid on an image.

FIG. 36 depicts an example of embodiments of the user interface of the tool for screening. FIG. 36A and FIG. 36B describe the user interface for single encounter processing whereas FIG. 36C and FIG. 36D describe the user interface for batch processing of multiple encounters. In FIG. 36A, a single encounter is loaded for processing and when the user clicks on "Show Lesions," the detected lesions are overlaid on the image, as shown in FIG. 36B. An embodiment of a user interface of the tool for screening for multiple encounters is shown in FIG. 36C, and the detected lesions overlaid on the image are displayed when the user clicks on "View Details," as shown in FIG. 36B.

The embodiments described above are adaptable to different embodiments for screening of different retinal diseases. Additional embodiments are described in the sections below related to image screening for screening for diabetic retinopathy and image screening for screening for cytomegalovirus retinitis.

a. Multi-Level Descriptors For Screening

Figure 37:
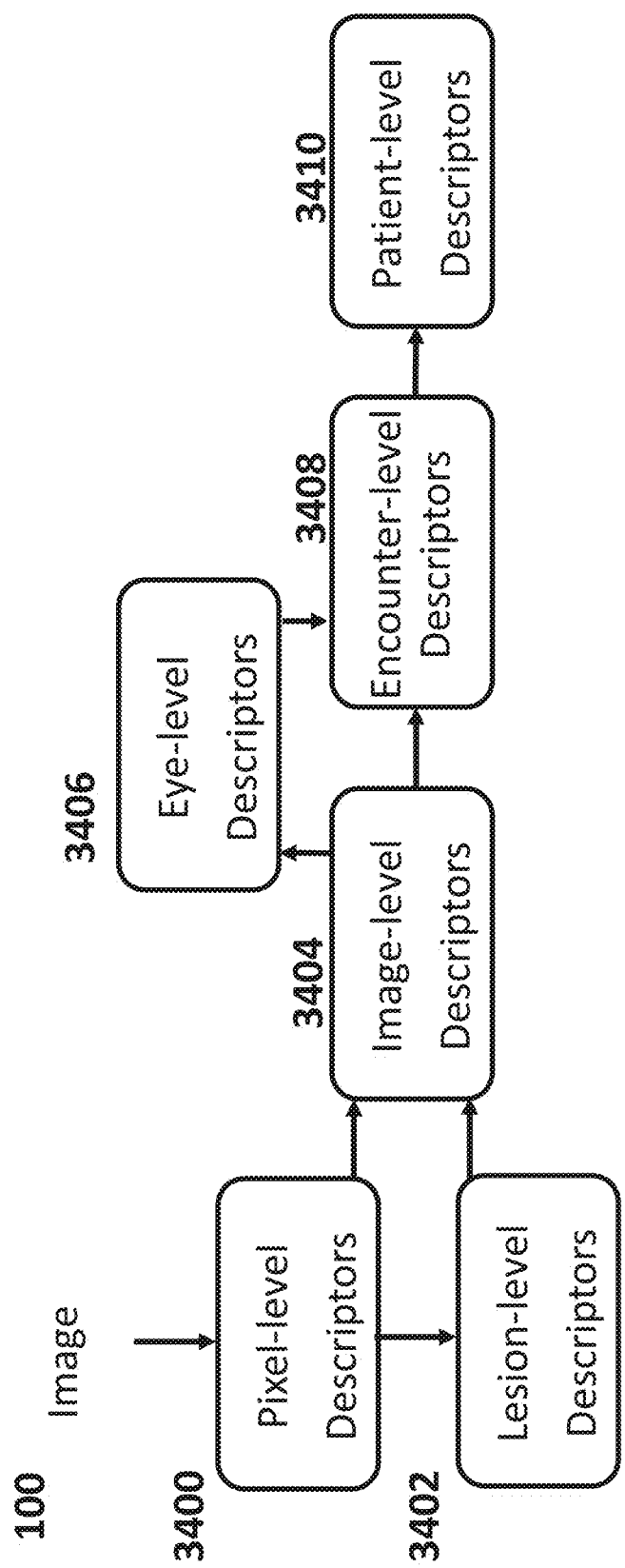
FIG. 37 is a block diagram of one embodiment that indicates evaluation of descriptors at multiple levels.

FIG. 37 discloses one embodiment of an architecture for descriptor computation at various levels of abstraction. The illustrated blocks may be implemented on the cloud 19014, a computer or computing device 19004, or a mobile device 19008, or the like, as shown in FIG. 1. Pixel level descriptors 3400 are computed, using for example the process described in the section above entitled "Lesion Classification". Lesion classifiers for microaneurysms, hemorrhages, exudates, or cottonwoolspots are used to compute a decision statistic for each of these lesions using the pixel level descriptors. Pixels are grouped into blobs based on local image properties, and the lesion decision statistics for a particular lesion category of all the pixels in a group are averaged to obtain blob-level decision statistic 3402. Histograms of pixel-level and blob averaged decision statistics for microaneurysms, hemorrhages, exudates, or cottonwoolspots are concatenated to build image level descriptors 3404. Alternatively, image level descriptors also include bag of words (BOW) descriptors, using for example the process described in the section above entitled "Description With Dictionary of Primary Descriptors". Eye-level descriptors 3406 are evaluated as the maximum value across all the image level descriptors for the images that belong to an eye. Images that belong to a particular eye can be either identified based on metadata, inferred from file position in an encounter or deduced from the image based on relative positions of ONH and macula. Encounter-level descriptors 3408 are evaluated as the maximum value across all the image level descriptors for the images that belong to an encounter. Alternatively, encounter-level descriptors can be obtained by concatenating eye-level descriptors. Lesion dynamics computed for a particular patient from multiple encounters can be used to evaluate patient level descriptors 3410.

b. Hybrid Classifiers

Ground truth labels for retinopathy and maculopathy can indicate various levels of severity, for example R0, R1, M0 and so on. This information can be used to build different classifiers for separating the various DR levels. In one embodiment, improved performance can be obtained for classification of R0M0 (no retinopathy, no maculopathy) cases from other disease cases on Messidor dataset by simply averaging the decision statistics of the no-retinopathy-and-no-maculopathy ("R0M0") versus the rest classifier, and no-or-mild-retinopathy-and-no-maculopathy ("R0R1M0") versus the rest classifier. (A publically available dataset is kindly provided by the Messidor program partners at http://messidor.crihan.fr/.) One or more of the following operations may be applied with the weights $w_t$ on each training element initialized to the same value on each of the classifier $h_t$ obtained. In some embodiments, the operations are performed sequentially.

1. With the training dataset weighted the best remaining classifier $h_t$ is applied to evaluate AUROC $A_t$. The output weight $\alpha_t$ for this classifier is computed as below:

$$\alpha_t = \frac{1}{2}\ln\frac{A_t}{1-A_t}$$

2. The weight distribution $w_{t+1}$ on the input training set for the next classifier is computed as below:

$$w_{t+1}(i) = w_t(i)\exp\alpha_t(2(y_i \neq h_t(x_i))-1)$$

where, $x_i, y_i$ are the classifier inputs and the corresponding labels.

The output weights $\alpha_t$ are used to weight the output of each of the classifiers to obtain a final classification decision statistic.

c. Ensemble Classifiers

In one embodiment, ensemble classifiers are employed, which are a set of classifiers whose individual predictions are combined in a way that provides more accurate classification than the individual classifiers that make them up. In one embodiment, a technique called stacking is used, where an ensemble of classifiers, at base level, are generated by applying different learning algorithms to a single dataset, and then stacked by learning a combining method. Their good performance is proved by the two top performers at the Netflix competition using, for example, techniques disclosed in Joseph Sill et al., *Feature-Weighted Linear Stacking*, arXiv e-print, Nov. 3, 2009. The individual weak classifiers, at the base level, may be learned by using algorithms such as decision tree learning, naïve Bayes, SVM, or multi response linear regression. Then, at the meta level, effective multiple-response model trees are used for stacking these classifier responses.

d. Deep Learning

In another embodiment, the system employs biologically plausible, deep artificial neural network architectures, which have matched human performance on challenging problems such as recognition of handwritten digits, including, for example, techniques disclosed in Dan Cireş an, Ueli Meier, and Juergen Schmidhuber, *Multi-Column Deep Neural Networks for Image Classification*, arXiv e-print, Feb. 13, 2012. In other embodiments, traffic signs, or speech recognition are employed, using, for example, techniques disclosed in M. D. Zeiler et al., "On Rectified Linear Units for Speech Processing," 2013. Unlike shallow architectures, for example, SVM, deep learning is not affected by the curse of dimensionality and can effectively handle large descriptors. In one embodiment, the system uses convolution networks, sometimes referred to as cony-nets, based classifiers, which are deep architectures that have been shown to generalize well for visual inputs.

B. Types Of Diseases

1. Diabetic Retinopathy Screening a. General description

In one embodiment, the system allows screening of patients to identify signs of diabetic retinopathy (DR). A similar system can be applied for screening of other retinal diseases such as macular degeneration, hypertensive retinopathy, retinopathy or prematurity, glaucoma, as well as many others.

When detecting DR, two DR detection scenarios are often of interest: (i) detecting any signs of DR, even for example a single microaneurysm (MA) since the lesions are often the first signs of retinopathy or (ii) detecting DR onset as defined by the Diabetes Control and Complications Trial Control and Group, that is, the presence of at least three MAs or the presence of any other DR lesions. The publicly available Messidor dataset, which contains 1200 retinal images that have been manually graded for DR and clinically significant macular edema (CSME), can be used for testing the system. In one embodiment, the screening system, when testing for this Messidor dataset, uses >5MAs or >0 Hemorrhages (HMs) as criteria for detecting DR onset. For both of the detection scenarios, the goal is to quantify working on cross-dataset testing, training on a completely different data, or on a 50-50 test-train split of the dataset.

Figure 38:
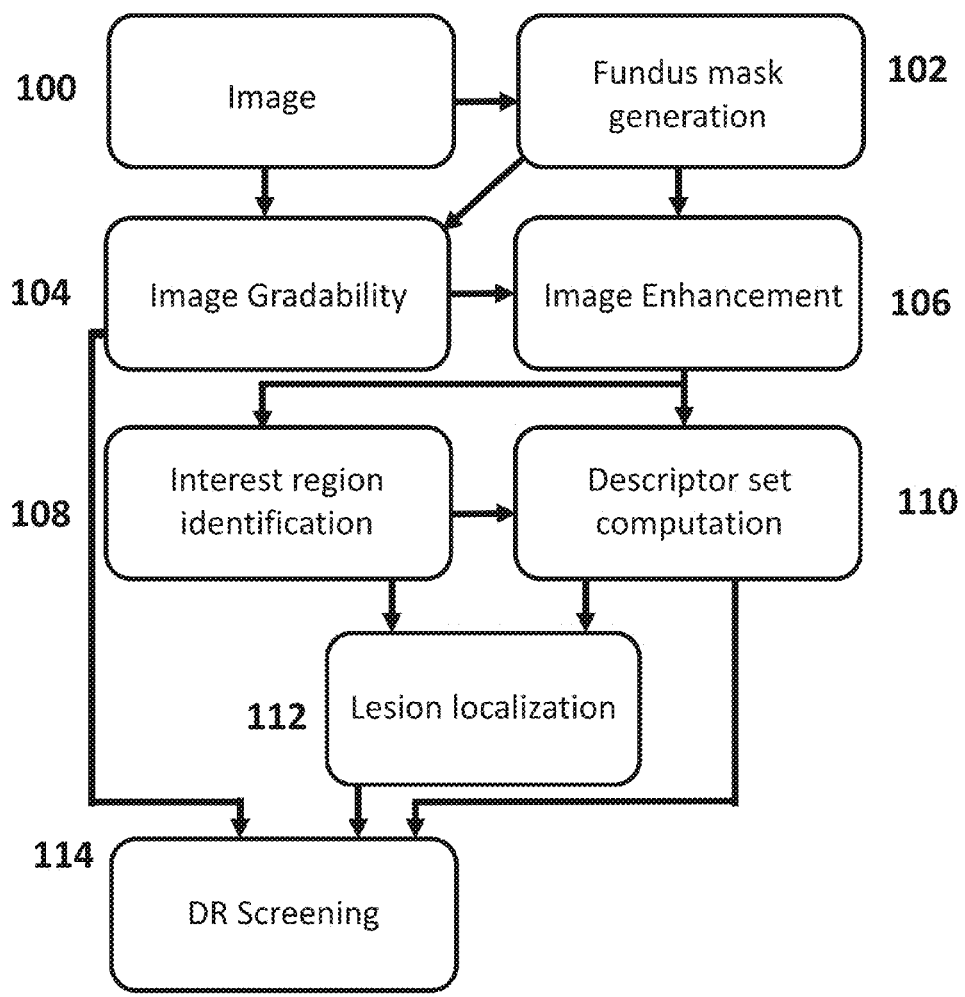
FIG. 38 is a block diagram of one embodiment of screening for retinal abnormalities associated with diabetic retinopathy.

FIG. 38 depicts one embodiment of a pipeline used for DR screening. The illustrated blocks may be implemented either on the cloud 19014, a computer or computing device 19004, a mobile device 19008, or the like, as shown in FIG. 1. The image 100 refers in general to the retinal data, single or multidimensional, that has been captured using a retinal imaging device, such as cameras for color image capture, fluorescein angiography (FA), adaptive optics, optical coherence tomography (OCT), hyperspectral imaging, scanning laser ophthalmoscope (SLO), wide-field imaging or ultra-wide-field imaging. Image 100 is input to fundus mask generation block 102 and image gradability computation block 104 and image enhancement module 106 if the image is of sufficient quality. Interest region identification block 108 and descriptor set computation block 110 feed into lesion localization block 112 which determines the most likely label and/or class of the lesion and extent of the lesion. This output can be used for multiple purposes such as abnormality screening, diagnosis, or the like. DR screening block 114 determines whether a particular fundus image includes abnormalities indicative of diabetic retinopathy such that the patient should be referred to an expert.

In one embodiment, two approaches can be used in the system: one for the 50-50 train/test split and the other for the cross-dataset testing with training on one dataset and testing on another. One embodiment uses the Messidor dataset and the DEI dataset (kindly provided by Doheny Eye Institute) which comprises 100 field 2 images with four lesions diligently annotated pixel-wise (MA, HM, EX and CW), and 125 field 2 images with MAs marked. When using the system on these datasets, the annotations performed precisely, often verifying the annotations using the corresponding fluorescein angiography (FA) images. This precise annotation sets high standards for the automated lesion localization algorithms, especially at lesion-level.

b. Features that can be Used for Automatic Detection i. Description With Dictionary Of Primary Descriptors In this embodiment, a dictionary of low-level features is computed by unsupervised learning of interesting datasets, referred to as codewords. The dictionary may be computed by technology disclosed in J. Sivic and A. Zisserman, "Video Google: A Text Retrieval Approach to Object Matching in Videos," in *9th IEEE International Conference on Computer Vision*, 2003, 1470-1477. Then an image is represented using a bag of words description, for example a histogram of codewords found in the image. This may be performed by finding the codeword that is closest to the descriptor under consideration. The descriptors for an image are processed in this manner and contribute to the histogram.

A 50-50 split implies that training is done with half the dataset and testing is done on the other half. The computation of the dictionary can be an offline process that happens once before the system or method is deployed. In one embodiment, the unsupervised learning dataset is augmented with descriptors from lesions. In an example implementation, the descriptors from lesions locations annotated on the DEI dataset are used. For this example implementation, the total number of descriptors computed is $N_{DEI}$ and $N_{Mess}$, for DEI and Messidor datasets, respectively. Then $N_{mess} \approx mN_{DEI}$, where $m \geq 1.0$ can be any real number, with each Messidor training image contributing equally to the $N_{mess}$ descriptor count. In one embodiment, m is set to 1 and in another embodiment it is set to 5. The random sampling of interesting locations allows signatures from non-lesion areas to be captured. The computed $N_{mess}+N_{DEI}$ descriptors are pooled together and clustered into K partitions using K-means clustering, the centroids of which give K-codewords representing the dictionary. The K-means clustering may be performed using techniques disclosed in James MacQueen, "Some Methods for Classification and Analysis of Multivariate Observations," in *Proceedings of the Fifth Berkeley Symposium on Mathematical Statistics and Probability*, vol. 1, 1967, 14.

After the dictionary computation, the bag of words based (BOW) secondary descriptors are computed. In one embodiment, for each image, the lesion descriptors 110 are computed. Using vector quantization, each descriptor is assigned a corresponding codeword from the previously computed dictionary. The vector quantization may be performed using techniques disclosed in Allen Gersho and Robert M. Gray, *Vector Quantization and Signal Compression* (Kluwer Academic Publishers, 1992). This assignment can be based on which centroid or codeword is closest in terms of Euclidean distance to the descriptor. A normalized K-bin histogram is then computed representing the frequency of codeword occurrences in the image. The histogram computation does not need to retain any information regarding the location of the original descriptor and therefore the process is referred to as "bagging" of codewords. These descriptors are referred to as bag of words (BOW) descriptors.

Table 5 is comparison of embodiments of the screening methods. The results for one embodiment is provided for reference alone, noting that the other results are not cross dataset. "NA" in the table indicates the non-availability of data. The column labelled "Quellec" provides results when applying the method described in Gwénolé Quellec et al., "A Multiple-Instance Learning Framework for Diabetic Retinopathy Screening," *Medical Image Analysis* 16, no. 6 (August 2012): 1228-1240, the column labelled "Sanchez" shows results when applying the method described in C. I. Sanchez et al., "Evaluation of a Computer-Aided Diagnosis System for Diabetic Retinopathy Screening on Public Data," *Investigative Ophthalmology & Visual Science* 52, no. 7 (Apr. 28, 2011): 4866-4871, and the column labelled "Barriga" shows results when applying the method of E. S. Barriga et al., "Automatic System for Diabetic Retinopathy Screening Based on AM-FM, Partial Least Squares, and Support Vector Machines," in 2010 *IEEE International Symposium on Biomedical Imaging: From Nano to Macro*, 2010, 1349-1352.

TABLE 5

| | | System embodiment one | System Embodiment two | Quellec... | Sanchez... | Barriga... |
|---|---|---|---|---|---|---|
| AUROC | | 0.915 | 0.857 | 0.881 | 0.876 | 0.860 |
| sensitivity | specificity | | | | | |
| | 50% | 95% | 88% | 92% | 92% | NA |
| | 75% | 88% | 82% | 86% | 83% | NA |
| specificity | sensitivity | | | | | |
| | 90% | 70% | 39% | 66% | 55% | NA |
| | 85% | 82% | 62% | 75% | 65% | NA |

In one embodiment, after the BOW descriptors have been computed for the images, they are subjected to term frequency—inverse document frequency (tf-idf) weighting, using, for example, techniques disclosed in Christopher D. Manning, Prabhakar Raghavan, and Hinrich Schütze, *Introduction to Information Retrieval*, vol. 1 (Cambridge University Press Cambridge, 2008). This is done to scale down the impact of codewords that occur very frequently in a given dataset and that are empirically less informative than codewords that occur in a small fraction of the training dataset, which might be the case with "lesion" codewords. In some embodiments, the inverse document frequency (idf) computation is done using the BOW descriptors of the training dataset images. In addition, during computation of document frequency, a document may be considered if the raw codeword frequency in it is above a certain threshold $T_{df}$. The tf-idf weighting factors computed on training dataset are stored and reused on the BOW descriptors computed on the images in the test split of Messidor dataset during testing.

Figures 39, 40:
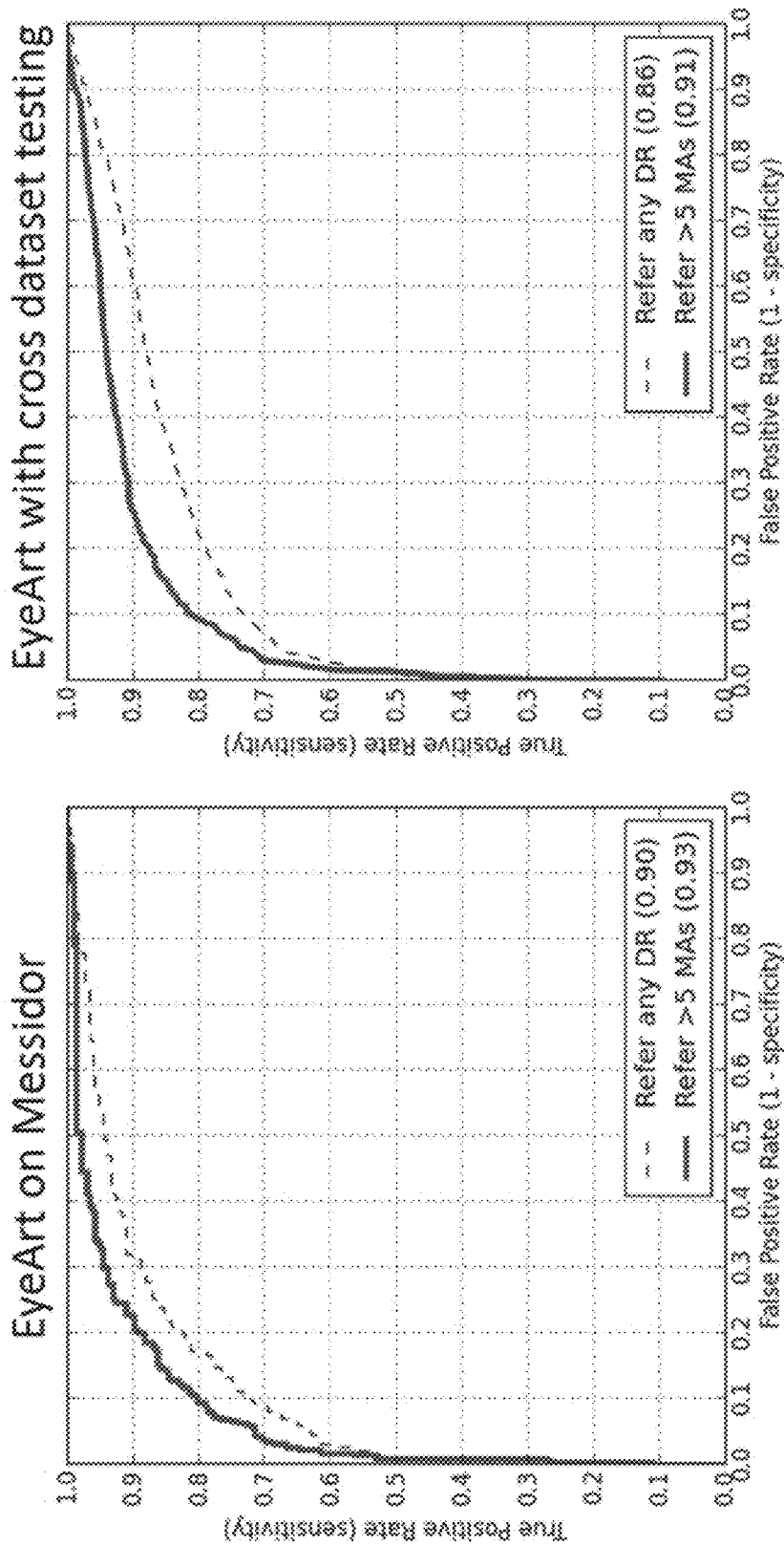
FIG. 39 shows an embodiment of an ROC plot for one embodiment of screening classifier with a 50/50 train-test split.
FIG. 40 shows an embodiment of an ROC plot for one embodiment on entire dataset with cross dataset training.

In one embodiment, the system adds a histogram of the decision statistics (for example, the distance from classifier boundaries) for pixel level MA and HM classifiers. This combined representation may be used to train a support vector machine (SVM) classifier using the 50-50 test/train split. In one embodiment, the number of descriptors computed is $N_{Mess} \approx N_{DEI} \approx 150,000$, and these 300K descriptors are clustered to get K=300 codewords. In addition, the document frequency computation may use $T_{df}=0$, but for other embodiments may use $T_{df}=3$. These parameter choices of these embodiments result in an impressive ROC curve with AUROC of 0.940 for DR onset and 0.914 for DR detection as shown in Table 5 and FIG. 39. These are the best results among those reported in literature for the Messidor dataset.

In addition, in one embodiment, a histogram of blob-level decision statistics that is computed using one or more of the following operations is added: (i) computation of the blobs in the image at various scales using the detected pixels, (ii) computation of the average of the decision statistics to obtain one number per blob, (iii) training of one or more another classifiers for lesions using the blob-level decision statistics as the feature vector and use the new decision statistic, or (iv) computation of one or more histograms of these decision statistics to form a blob-level histogram(s) descriptor. In one embodiment, these histogram descriptors are normalized to sum to 1 so as to mathematically look like a probability distribution.

As discussed above, different descriptor types may be combined in various embodiments, this does not preclude the use of any individual descriptor type, or an arbitrary combination of a subset of descriptor types.

c. Screening Using Lesion Classifiers Trained On Another Dataset (Cross-Dataset Testing)

In another embodiment, the method or system could be applied to a cross-dataset scenario. This implies that the testing is done on a completely new, unseen dataset. In an example implementation, cross-dataset testing is applied on all 1200 Messidor images without any training on this dataset. Instead, the system uses the decision statistics computed for the various lesions. These statistics are the distances from classifier boundaries, with the classifier being trained on the expert-annotated images. In this example implementation, 225 images from the DEI dataset are employed. The ROC curves for this example implementation, shown in FIG. 40, demonstrate an impressive cross-dataset testing performance, especially for detecting DR onset (AUROC of 0.91). For detecting any signs of DR, the AUROC of 0.86 convincingly beats the best reported in literature, including cross dataset AUROC of 0.76 disclosed in Quellec et al., "A Multiple-Instance Learning Framework for Diabetic Retinopathy Screening.". Table 5 presents a comparison of screening performance of some embodiments with various competing approaches on the Messidor dataset, clearly showing superior diagnostic efficacy of the disclosed embodiments. Table 6 compares the results from the two approaches. Table 6 provides screening results (AUROC) for the two embodiments of screening system on Messidor dataset.

TABLE 6

| Method | Refer any retinopathy | Refer > 5 MAs |
| --- | --- | --- |
| System embodiment one | 0.915 | 0.943 |
| System embodiment two | 0.857 | 0.910 |

2. Cytomegalovirus Screening a. General Description

Cytomegalovirus retinitis (CMVR) is a treatable infection of the retina affecting HIV and AIDS patients, and is a leading cause of blindness in many developing countries. In one embodiment, methods and systems for screening of Cytomegalovirus retinitis using retinal fundus photographs is described. Visual inspection of the images from CMVR patients reveals that, images with CMVR typically have large sub-foveal irregular patches of retinal necrosis appearing as a white, fluffy lesion with overlying retinal hemorrhages as seen in FIGS. 41C and 41D. These lesions have severely degraded image quality, for example, focus, contrast, normal color, when compared with images of normal retina, as shown in FIGS. 41A and 41B. A system which can effectively capture and flag the degradation in image quality can be used to screen for CMVR. Accordingly, in one embodiment, the image quality descriptors are adapted to the problem of CMVR screening, providing a new use of the image quality descriptors described herein.

b. Features that can be Used for this Type of Automatic Detection

In one embodiment, the image analysis engine automatically processes the images and extracts novel quality descriptors, using, for example, the process described in the section above entitled "Lens Shot Image Classification". These descriptors are then subjected to principal component analysis (PCA) for dimensionality reduction. They can then be used to train a support vector machine (SVM) classifier in a 5-fold cross-validation framework, using images that have been pre-graded for Cytomegalovirus retinitis by experts, for example, into two categories: normal retina, and retina with CMVR. In one embodiment, images graded by experts at UCSF and Chiang Mai University Medical Centre, Thailand are employed. The system produces a result of refer for a patient image from category retina with CMVR, and no refer for a patient image from category normal retina.

Figure 42:
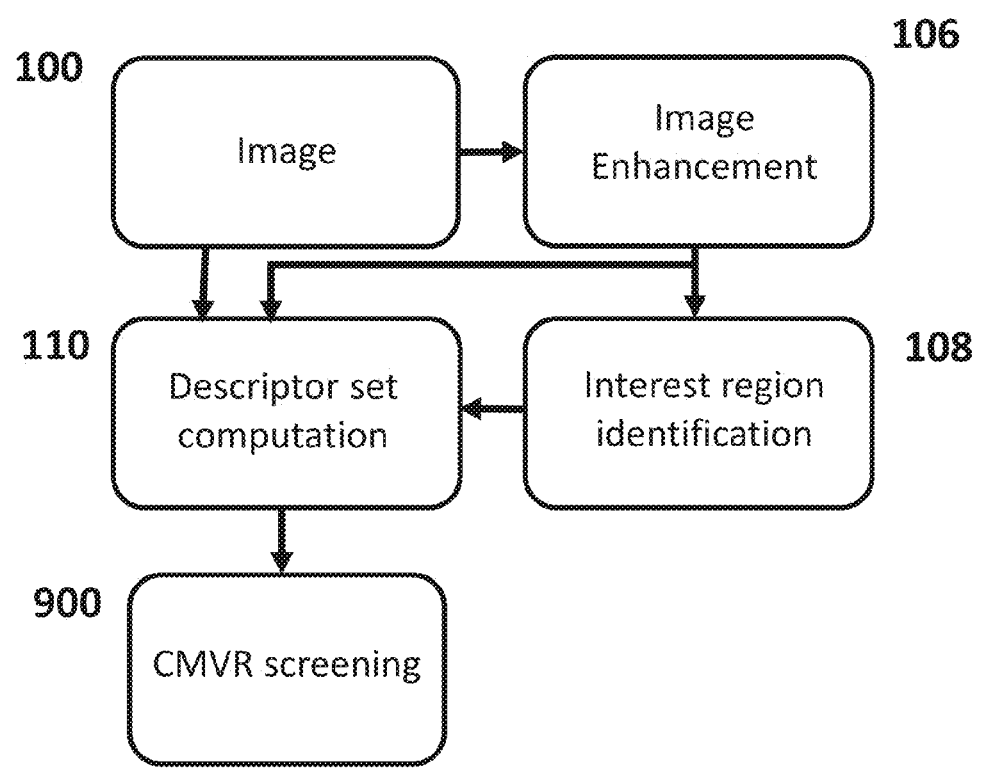
FIG. 42 is a block diagram of one embodiment of screening for retinal abnormalities associated with Cytomegalovirus retinitis.

FIG. 42 depicts a process for one embodiment of CMVR screening. The illustrated blocks may be implemented either on the cloud 19014, or a computer or computing device 19004, a mobile device 19008 or the like, as shown in FIG. 1. The image 100 refers in general to the retinal data, single or multidimensional, that has been captured using a retinal imaging device, such as cameras for color image capture, fluorescein angiography (FA), adaptive optics, optical coherence tomography (OCT), hyperspectral imaging, scanning laser ophthalmoscope (SLO), wide-field imaging or ultra-wide-field imaging. Image 100 is input to the image enhancement module 106 and then input to interest region identification block 108 and descriptor set computation block 110. The descriptors are input to CMVR screening block 900 to determine whether a particular fundus image includes abnormalities indicative of Cytomegalovirus infection and that the patient needs to be referred to an expert.

One embodiment was tested using 211 images graded for CMVR, by randomly splitting them into 40 different training-testing datasets. In each split, 75% of the images were used for training and the other 25% were reserved for testing. As expected, the lesion degraded, poor quality images were flagged to be positive for CMVR by the system with an average accuracy of 85%, where average area under ROC curve (AUROC) was 0.93. For many of the images, the presence of large out-of-focus, blurry, or over-/under-exposed regions, such as shown in FIGS. 41E, 41F for example, resulted in the degradation of image quality causing the experts to be unsure about the presence or absence of CMVR during screening. These images, marked with category cannot determine, were excluded from the above experiments. By choosing an SVM classifier that produces an ROC curve with an AUROC close to the average of 0.93 obtained during the 40 experiments, an additional 29 images from the cannot determine category were tested. None of these images were included during training phase. The system recommended that 27 of 29 images (patients) be referred, which is acceptable given that experts too did not have consensus on CMVR status of those two images.

In one embodiment, the quality of the image is first analyzed using a "gradability assessment" module. This module will flag blurry, saturated or under exposed images to be of poor quality and unsuitable for reliable screening. The actual CMVR screening would then be performed on images that have passed this quality module. Both system could use the same descriptors, but one can use a support vector regressor engine trained to assess quality, and the other a support vector classifier trained to screen for CMVR. In another embodiment, additional descriptors are included, such as texture, color layout, and/or other descriptors to the CMVR screening setup to help distinguish the lesions better.

3. Other Diseases a. Alzheimer's

Patients with early forms of Alzheimer's disease (AD) display narrower retinal veins compared to their peers without AD as discussed in Fatmire Berisha et al., "Retinal Abnormalities in Early Alzheimer's Disease," Investigative Ophthalmology & Visual Science 48, no. 5 (May 1, 2007): 2285-2289. Hence, AD can be screened by customized vasculatoic analysis.

b. Stroke

The retinal arterioles may narrow as a result of chronic hypertension and this may predict stroke and other cardiovascular diseases independent of blood pressure level as discussed in Tien Yin Wong, Ronald Klein, A. Richey Sharrett, David J. Couper, Barbara E. K. Klein, Duan-Ping Liao, Larry D. Hubbard, Thomas H. Mosley, "Cerebral white matter lesion, retinopathy and risk of clinical stroke: The Atherosclerosis Risk in the Communities Study". JAMA 2002; 288:67-74. Thus, the system may also be used to screen for strokes.

c. Cardiovascular Diseases

The retinal arterioles may narrow as a result of chronic hypertension and this may predict stroke and other cardiovascular diseases independent of blood pressure level, as discussed in Tien Y. Wong, Wayne Rosamond, Patricia P. Chang, David J. Couper, A. Richey Sharrett, Larry D. Hubbard, Aaron R. Folsom, Ronald Klein, "Retinopathy and risk of congestive heart failure". JAMA 2005; 293:63-69. Thus, the system may be used to screen for cardiovascular diseases.

d. Retinopathy of Prematurity

Neovascularization, vessel tortuosity and increased vessel thickness indicate retinopathy of prematurity, as discussed in Flynn Jt et al., "Retinopathy of Prematurity. Diagnosis, Severity, and Natural History." Ophthalmology 94, no. 6 (June 1987): 620-629. Thus, retinopathy of prematurity can be analyzed by automated retinal image analysis tools for screening.

e. Macular Degeneration

Lesions may also indicate macular degeneration as discussed in A. C. Bird et al., "An International Classification and Grading System for Age-Related Maculopathy and Age-Related Macular Degeneration," Survey of Ophthalmology 39, no. 5 (March 1995): 367-374. Thus, lesions such as drusen bodies can be detected and localized using the lesion localization system described in the section above entitled "Lesion Localization" and this disease can be screened for using a similar setup as described in the section "Diabetic retinopathy screening".

VII. Architectures

It is recognized that the systems and methods may be implemented in a variety of architectures including telemedicine screening, cloud processing, or using other modalities.

A. Telemedicine Screening

1. General Description

Figure 43A:
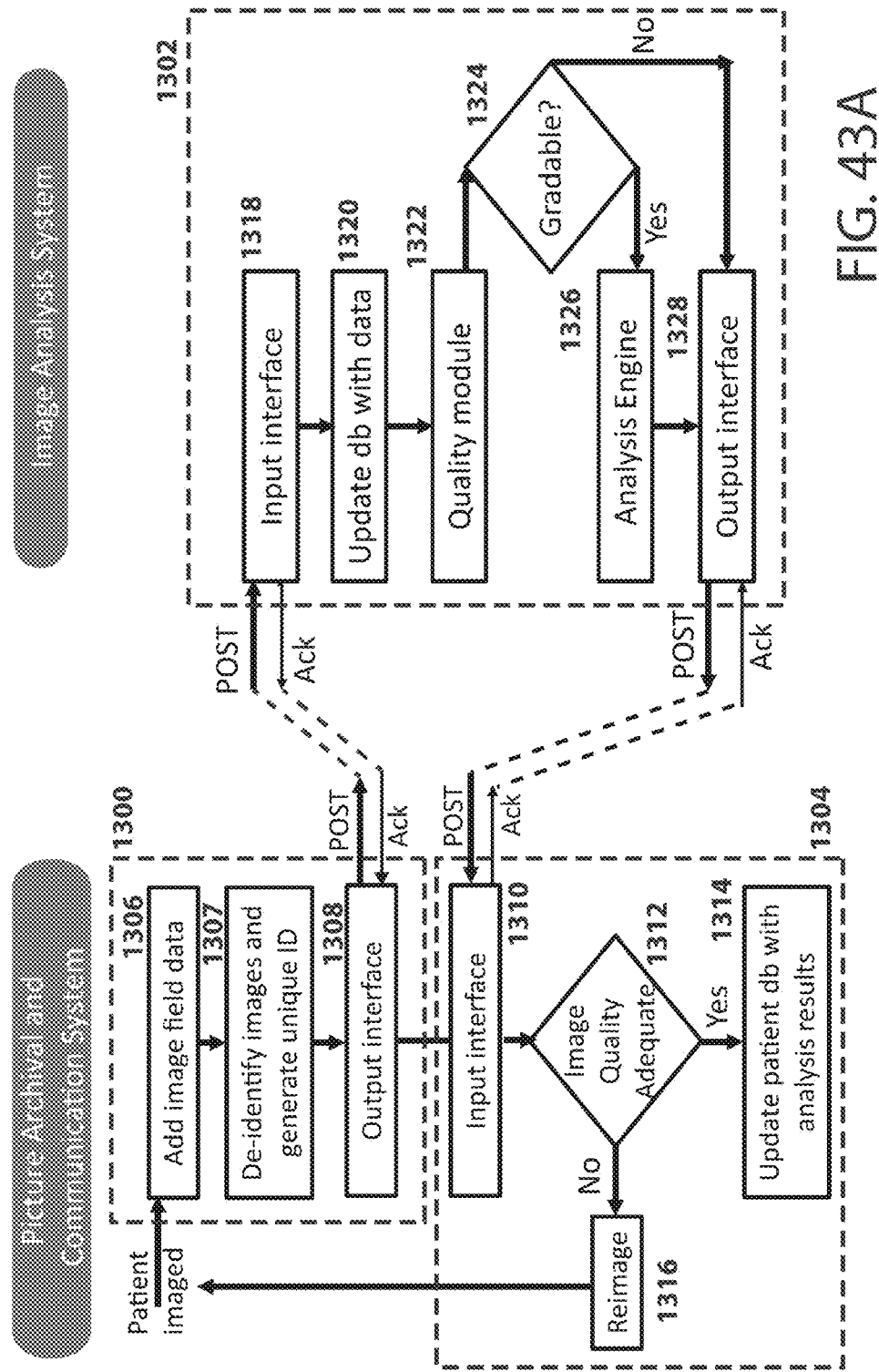
FIG. 43A outlines the operation of one embodiment of an Image Analysis System-Picture Archival and Communication System Application Program Interface (API).
Figure 43B:
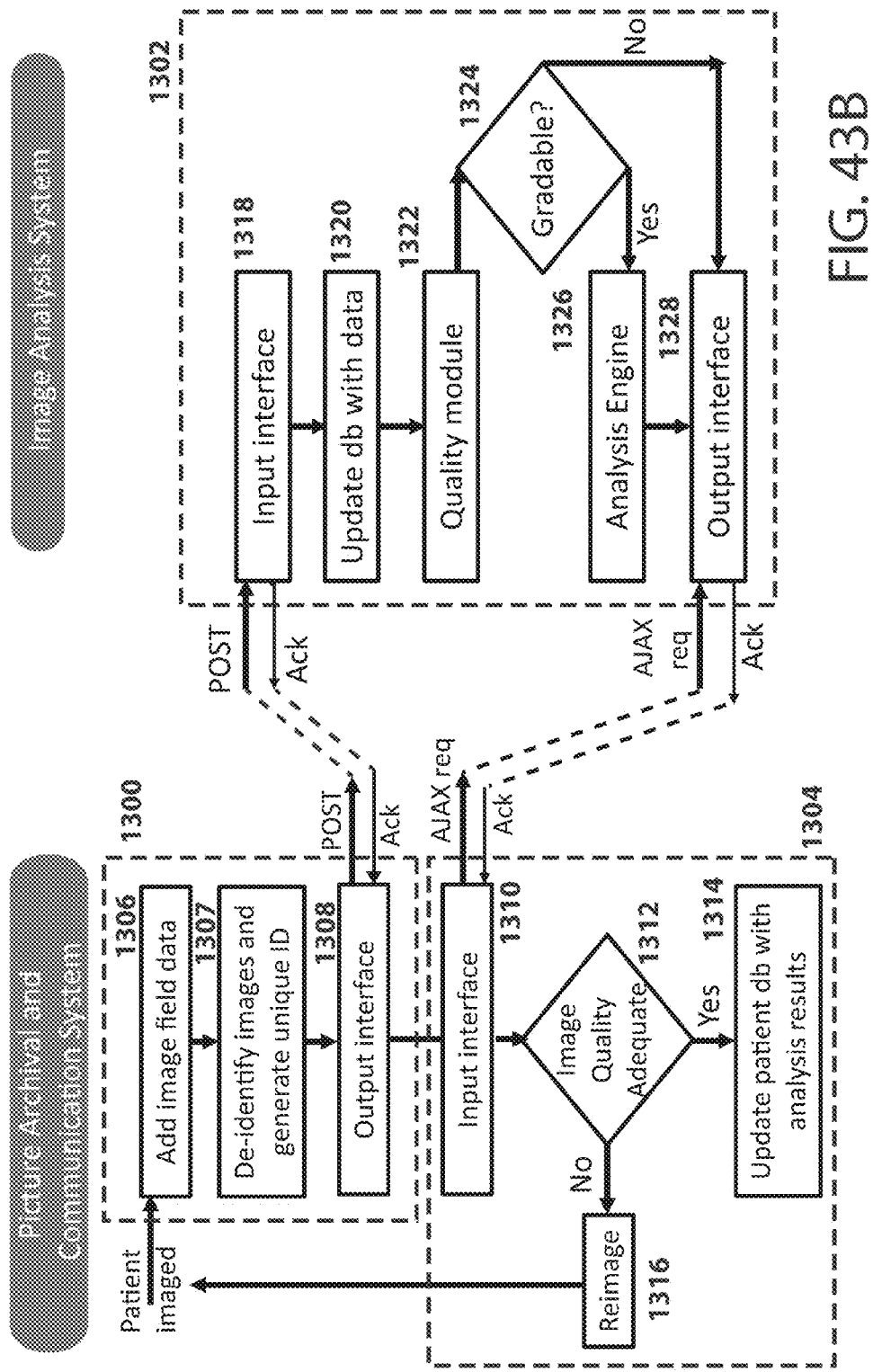
FIG. 43B outlines the operation of an additional API.

In one embodiment, the system includes a flexible application programming interface (API) for integration with existing or new telemedicine, systems, programs, or software. The Picture Archival and Communication System (PACS) is used as an example telemedicine service to enable such an integration. Block diagram of one embodiment of such a system is shown in FIGS. 43A and 43B. The system includes an API allowing coding of one or more of patients' metadata 1306, de-identifying images 1307 to anonymize patients for analysis and protect privacy, analyzing image quality 1312, initiating reimaging as needed 1316, updating patient metadata, storing images and analysis results in database 1314, inputting 1310, and/or outputting 1308 transmission interfaces. The Image Analysis System (IAS) comprises one or more of the following: input 1318 and output 1328 transmission interfaces for communication with the PACS system, a database updater 1320, a quality assessment block 1322 to assess image gradability 1324, an analysis engine 1326 that can include a combination of one or more of the following tools: disease screening, lesion dynamics analysis, or vessel dynamics analysis. In one embodiment, the PACS and/or the IAS system could be hosted on remote or local server or other computing system, and in another embodiment, they could be hosted or cloud infrastructure.

In one embodiment, the API is designed to enable seamless inter-operation of the IAS with a telemedicine service, such as PACS, though any telemedicine system, software, program, or service could be used. An interface for one embodiment is presented in FIG. 43A.

In one embodiment, the API includes one or more of the following features:

Image data sent to IAS server: Once a patient is imaged, relevant metadata, like retinal image field, is added, a unique control number or identifier (id) is generated for the case, and the patient image is de-identified by PACS. The id along with the de-identified images and metadata is then sent to IAS, for example block 1300 and URL 1 (https://api.eyenuk.com/eyeart/upload), using a secure protocol such as the secure hypertext transfer protocol (HTTPS) POST request with multi-part/form content type, which also includes authentication from PACS and/or the user.

Ack sent back to PACS: Once the POST request is received by the IAS server, the input data is validated, and the application and user sending the data are authenticated. After authenticating the request, an acknowledgment is sent back.

Image Analysis on IAS Analysis Engine: IAS image analysis engine, for example block 1302, updates the database with the patient images, associated data and unique id, and proceeds to analyze the images. The images are assessed for their gradability in multiple threads. If the images are of gradable quality, the screening results are estimated.

2. Transfer Of Analysis Results

In one embodiment, IAS initiates the transfer of results to PACS. In this mode of operation, PACS would not have a control over when it would receive the results. The transfer may include one or more of the following:

Image analysis results sent to PACS: For images of gradable quality, the corresponding screening results are embedded as JSON (JavaScript Object Notation) data and sent in a new HTTPS POST request to the PACS server using protocols discussed in https://upload.eyepacs.com/eyeart_analysis/upload. Ungradable images are indicated as such.

Ack sent back to IAS server: After receiving the results, PACS server validates the received data and sends an acknowledgment back, block 1304.

In another embodiment, PACS initiates the transfer of results to its system. In this mode of operation, PACS can choose when to retrieve the analysis results from IAS server. This circumvents the possibility of data leaks, since the screening results are sent from IAS upon request. The transfer may include one or more of the following:

PACS queries for result status: Similar to the initial POST request, the PACS server uses HTTPS POST request with multi-part/form content type, to transmit the image ids for which it wants to know the status of image analysis using, for example, protocols disclosed in https://api.eyenuk.com/eyeart/status.

Ack sent back to PACS: Once the POST request is received by the IAS server, the input id is validated, and the application and user sending the data are authenticated. An acknowledgment is then sent back along with the status of the result, (for example, "In Queue" or "Processing" or "Done") for the requested id or ids.

PACS queries for results: The PACS server sends an AJAX request (for example, jQuery $.get) to asynchronously, in the background, retrieve the results from the IAS server using, for example, protocols disclosed in https://api.eyenuk.com/eyeart/result. The appropriate AJAX callbacks are set for handling events such as processing of results once it is received, handling failure of the request, or the like.

Posting results to PACS: Once the processing is done, for images of gradable quality, the corresponding screening results are embedded as JSON data and sent as a response to the authenticated PACS server AJAX request. If images are ungradable they are indicated as such in the response. This response, triggers the corresponding callback (set during the request) at the PACS server, which could process the results and add them to the patient database, for example block 1304.

Table 7 presents one embodiment of technical details of an interface with telemedicine and error codes for a Telemedicine API. The design includes considerations directed to security, privacy, data handling, error conditions, and/or independent server operation. In one embodiment, the PACS API key to obtain "write" permission to IAS server would be decided during initial integration, along with the IAS API key to obtain "write" permission to PACS. The API URL, such as https://upload.eyepacs.com/eyeart_analysis/upload, for IAS to transfer results to PACS could either be set during initial registration or communicated each time during the POST request to https://api.eyenuk.com/eyeart/upload.

TABLE 7

| Error Code | Description |
| --- | --- |
| 1 | No images specified |
| 2 | No quality structure specified |
| 3 | General upload failure |
| 4 | Unique ID not specified |
| 5 | Invalid signature |
| 6 | Invalid API key |
| 7 | Insufficient permissions |

Table 8 shows one embodiment of details of an IAS and PACS API. One embodiment of error codes are described in Table 7. The URLs uses in the table are for illustrative purposes only.

TABLE 8

| Authentication | Arguments | Success response | Error Codes |
| --- | --- | --- | --- |
| URL 1: https://api.eyenuk.com/eyeart/upload | | | |
| API key, User ID | multi-part/form content type with images, unique id for identifying images of a particular patient, dictionary containing the retinal image fields for each image. | HTTP 200 | 1, 3, 4, 6, 7 |
| URL 2: https://upload.eyepacs.com/eyeart_analysis/upload | | | |
| API Key | JSON object with unique id, Structure with DR screening analysis details, Structure with quality analysis details. | HTTP 200 | 2, 3, 4, 6, 7 |
| URL 3: https://api.eyenuk.com/eyeart/status | | | |
| API key, User ID | multi-part/form content type with unique ids for images. | HTTP 200 | 3, 4, 6, 7 |
| URL 4: https://api.eyenuk.com/eyeart/result | | | |
| API key, User ID | AJAX request (possibly jQuery $.get) with callbacks for success and failure. | HTTP 200 | 3, 4, 6, 7 |

B. Processing On The Cloud

Image processing and analysis can be performed on the cloud, including by using systems or computing devices in the cloud. Large-scale retinal image processing and analysis may not be feasible on normal desktop computers or mobile devices. Producing results in near constant time irrespective of the size of the input dataset is possible if the retinal image analysis solutions are to be scaled. This section describes the retinal image acquisition and analysis systems and methods according to some embodiments, as well as the cloud infrastructure used to implement those systems and methods.

1. Acquisition And Analysis Workflow

Figure 44:
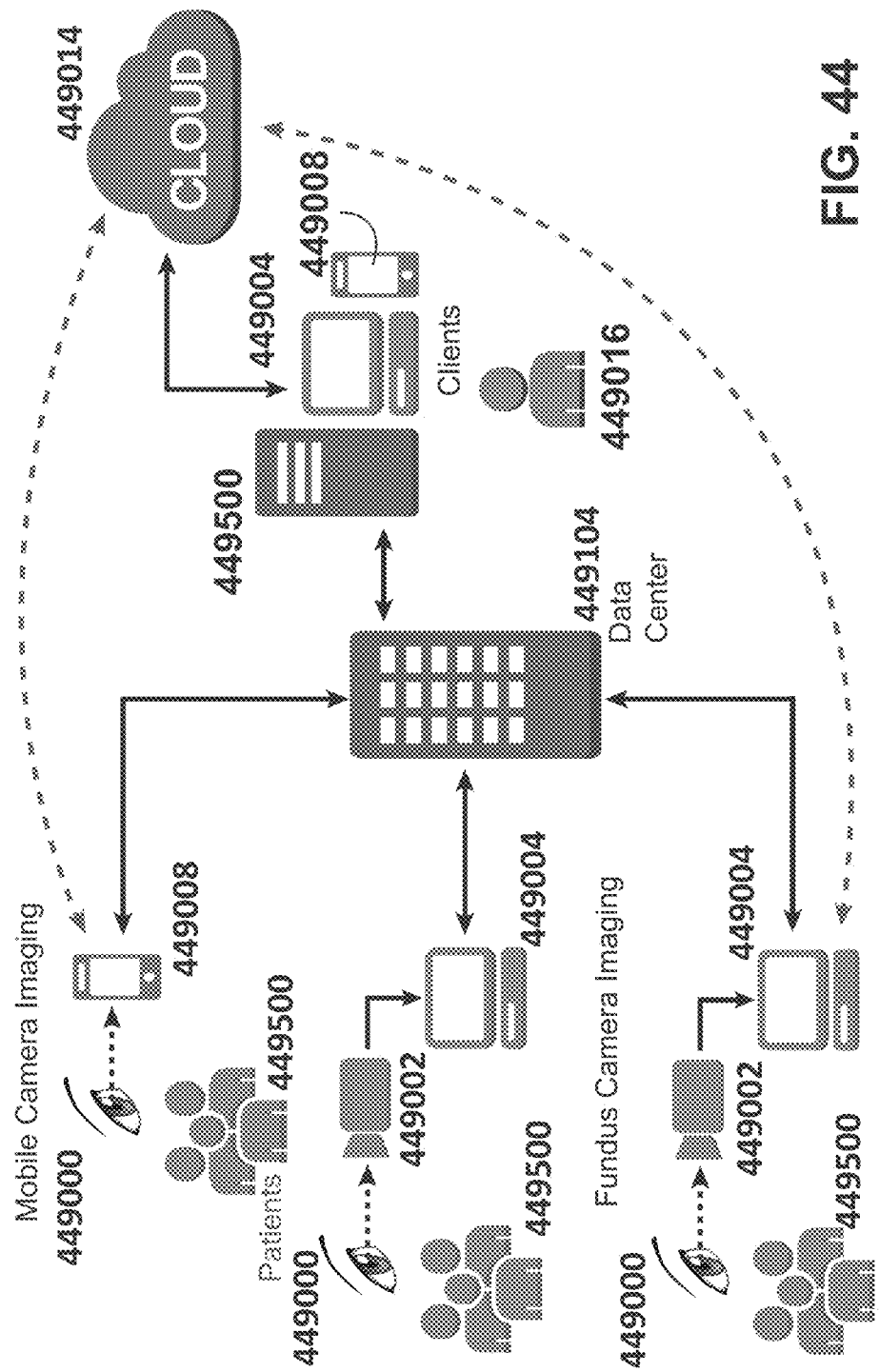
FIG. 44 illustrates various embodiments of a cloud-based analysis and processing system and process.

FIG. 44 shows an embodiment of a retinal image acquisition and analysis system. Diabetic retinopathy patients, and patients with other vision disorders, visit diagnostic clinics for imaging of their retina. During a visit, termed an encounter, multiple images of the fundus are collected from various fields and from both the eyes for each patient. In addition to the color fundus images, photographs of the lens are also added to the patient encounter images. These images are acquired by clinical technicians or trained operators, for example, on color fundus cameras or portable cellphone based cameras.

In an embodiment of cloud-based operation, the patient 449000 image refers to the retinal data, single or multidimensional, captured from the patient using a retinal imaging device, such as cameras for color image capture, fluorescein angiography (FA), adaptive optics, optical coherence tomography (OCT), hyperspectral imaging, scanning laser ophthalmoscope (SLO), wide-field imaging or ultra-wide-field imaging. The acquired images are stored on the local computer or computing device 449004, or mobile device 449008 and then transmitted to a central data center 449104. Operators at the data center can then use traditional server-based or computing device-based 449500, desktop-based 449004, or mobile-based 449008 clients to push these images to the cloud 449014 for further analysis and processing. The cloud infrastructure generates patient-level diagnostic reports which can trickle back to the patients, for example, through the same pipeline, in reverse.

In another embodiment of cloud-based operation, the imaging setup can communicate with the cloud, as indicated by dotted lines in FIG. 44. The images can be pushed to the cloud following acquisition. The diagnostic results are then obtained from the cloud, typically within minutes, enabling the clinicians or ophthalmologists to discuss the results with the patients during their imaging visit. It also enables seamless re-imaging in cases where conclusive results could not be obtained using the initial images.

In another embodiment of cloud-based operation, data centers store images from thousands of patients 449500. The data, for example, may have been collected as part of a clinical study for either disease research or discovery of drugs or treatments. The patient images may have been acquired, in preparation for the study, and then pushed to the cloud for batch-processing. The images could also be part of routine clinical workflow where the analysis is carried out in batch mode for several patients. The cloud infrastructure can be scaled to accommodate the large number of patient encounters and perform retinal analysis on the encounters. The results can be presented to the researchers in a collated fashion enabling effective statistical analysis for the study.

2. Image Analysis On The Cloud

Figure 45:
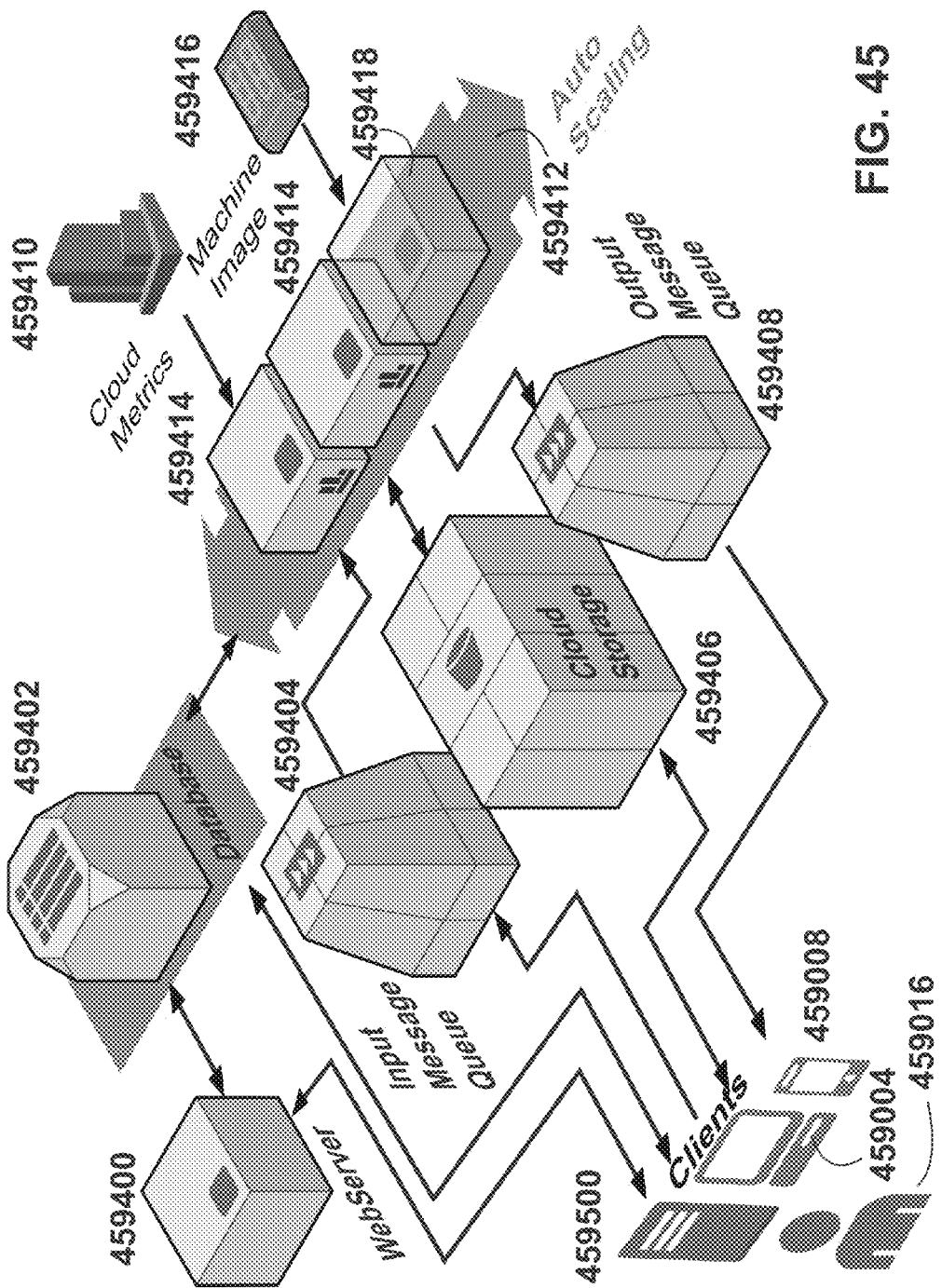
FIG. 45 illustrates architectural details of one embodiment of a cloud-based analysis and processing system.

FIG. 45 shows one embodiment of the cloud infrastructure 19014 used for retinal image processing and analysis. The client can be server-based or computing device-based 459500, desktop-based 459004, or mobile-based 459008. In one embodiment the client may be operated by a human operator 459016. The workflow can include one or more of the following:

First, the client logs-in to the web-server 459400 and requests credentials for using the cloud infrastructure. Following this authorization action, the client can access the various components of the cloud infrastructure.

During authorization, the client can send the number of encounters or images it plans to process in a run. Based on this number, the web-server initializes the components of the cloud, for example, Input 459404 and output 459408 message queues: These queues are fast, reliable and scalable message queuing services which act as an interface between client and the cloud. Messages in input queue indicate which encounters are ready for analysis, while those in output queue indicate which encounters have been analyzed on the cloud.

Cloud storage 459406: Can comprise a distributed network of hard disks (magnetic or solid-state), concurrently accessible via high-bandwidth connections to the worker machines. They can provide high security features, such as data encryption and firewalls, to guard against unauthorized access. They can also provide reliability, by, for example, redundant data storage across the network, against hardware and data failures allowing for disaster recovery.

Auto scaling group 459412: Can comprise of a group of worker machines or computing devices which can process the images in an encounter. For example, each worker machine 459414 can comprise of 32 or more, multi-core, 64-bit processors with high computing power and access to high-speed random access memory (RAM). The number of worker machines in the group is automatically scaled, that is, new machines are created or old ones terminated, depending on the cloud metrics.

Worker machine image 459416: Software that powers each worker machine. New machines created 459418 can be loaded with a machine image to transform them into worker machines 459414

Cloud metrics 459410: Component that monitors the number of encounters being processed by the existing machines, the number of encounters waiting to be processed in the input queue, and the current load on the worker machines. Auto scaling group uses this information to scale the number of worker machines.

After authorization, the client can perform some preliminary processing of the retinal images, which may include resizing or image enhancement.

The pre-processed images from an encounter are then uploaded to cloud storage, a corresponding encounter entry, which may contain image metadata, is made in the database 459402, and a message object is pushed to the input message queue to let the worker machines know that the encounter is ready for processing. In batch-processing mode, the images are pushed to the cloud in multiple software threads for faster uploads. After pushing the messages to the input queue, the client polls the output message queue for encounters that have been processed.

Once started, the worker machines poll the input message queue in anticipation of encounters to process. Once a message appears in the queue, they delete the message, access the database entry corresponding to that encounter, and download the images for that encounter to local memory. They then start processing and analyzing the images for retinal diseases. Each worker machine, can process multiple images or encounters simultaneously depending on the number of processor cores it has. During processing, the worker machines can save intermediate data to the cloud storage. Depending on the load each machine is handling and the number of messages, or encounters, waiting to be processed in the input message queue, the auto scaling component 459412 can automatically start new worker machines, load the required machine image, and initialize them to start pulling messages from the input queue and to start processing the encounters. The auto scaling component can also terminate machines if it thinks that computing power is left idle, in view of the volume of the new messages in the input queue.

After processing the images from an encounter, the worker process writes necessary data or images back to cloud storage, updates the corresponding encounter entry in the database with diagnostic results, and pushes a message to the output queue to let the client know that an encounter has been processed. If an error occurs during processing of an encounter, the encounter updates the database encounter entry indicating the error, and re-pushes the message back to the input queue, for another worker process to process the encounter. However, if the message has been re-pushed more than a couple of times, indicating that the encounter data itself has some problem, the worker process can delete the message from the input queue and push it to the output queue after updating the corresponding database entry.

Once a message appears in the output queue, the client deletes it from the queue and accesses the corresponding entry in the database to know the analysis results, or errors, if any, for an encounter. The results are then formatted and presented to the client. In batch-processing mode, the results for the encounters in the run can be collated into a spreadsheet for subsequent analysis by the client.

3. Use Of Amazon Web Services

In one embodiment, the cloud operation described above has been implemented using Amazon Web Services™ infrastructure, and the cloud storage is implemented using Simple Storage Service (S3). The input and output message queues may be implemented with Simple Queue Service (SQS). The web-server is hosted on a t1-micro Elastic Cloud Compute (EC2) instance. The database is implemented with the Relational Database Service (RDS) running a MySQL database instance. Each worker machine is a c3.8xlarge EC2 instance with 32-processors and 60 GB of RAM. The cloud metrics are obtained using Cloud Watch. The scaling of EC2 capacity (automatic creation and termination of worker machines) is done using Amazon Auto Scaling. The software that runs on each of the worker machines is stored as an Amazon Machine Image (AMI).

C. New And Other Image Modalities

1. Widefield And Ultra-Widefield Images

Widefield and ultra-widefield retinal images capture fields of view of the retina in a single image that are larger than 45-50 degrees typically captured in retinal fundus images. These images are obtained either by using special camera hardware or by creating a montage using retinal images of different fields. The systems and methods described herein can apply to widefield and ultra-widefield images.

2. Fluorescein Angiography Images

Fluorescein angiography involves injection of a fluorescent tracer dye followed by an angiogram that measures the fluorescence emitted by illuminating the retina with light of wavelength 490 nanometers. Since the dye is present in the blood, fluorescein angiography images highlight the vascular structures and lesions in the retina. The systems and methods described herein can apply to fluorescein angiography images.

3. Scanning Laser And Adaptive Optics Images

Scanning laser retinal imaging uses horizontal and vertical mirrors to scan a region of the retina that is illuminated by laser while adaptive optics scanning laser imaging uses adaptive optics to mitigate optical aberrations in scanning laser images. The systems and methods described herein can apply to scanning laser and adaptive optics images.

VIII. Computing System

Figure 46:
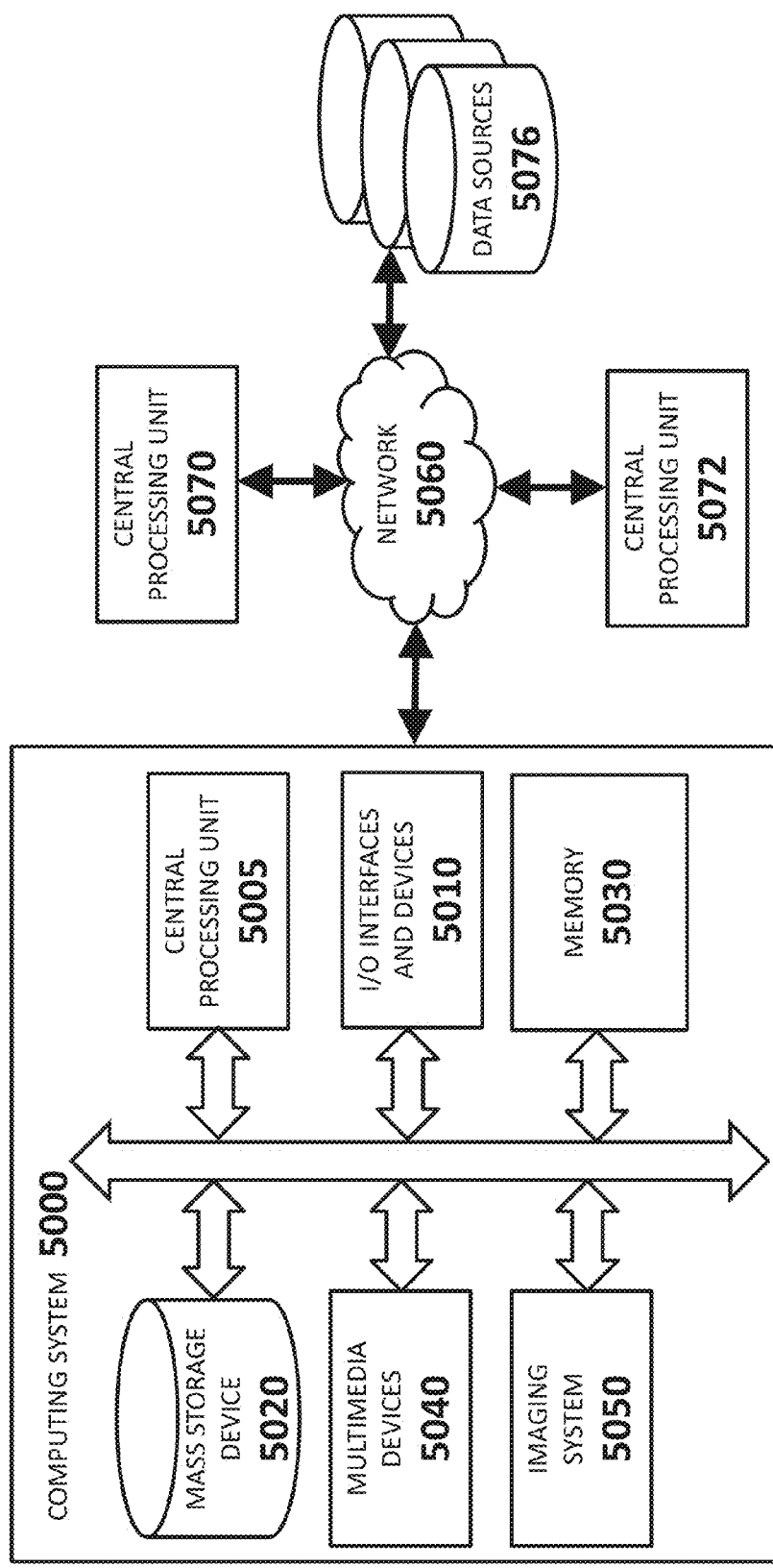
FIG. 46 is a block diagram showing one embodiment of an imaging system to detect diseases.

In some embodiments, the process of imaging is performed by a computing system 8000 such as that disclosed in FIG. 46.

In some embodiments, the computing system 5000 includes one or more computing devices, for example, a personal computer that is IBM, Macintosh, Microsoft Windows or Linux/Unix compatible or a server or workstation. In one embodiment, the computing device comprises a server, a laptop computer, a smart phone, a personal digital assistant, a kiosk, or a media player, for example. In one embodiment, the computing device includes one or more CPUS 5005, which may each include a conventional or proprietary microprocessor. The computing device further includes one or more memory 5030, such as random access memory ("RAM") for temporary storage of information, one or more read only memory ("ROM") for permanent storage of information, and one or more mass storage device 5020, such as a hard drive, diskette, solid state drive, or optical media storage device. Typically, the modules of the computing device are connected to the computer using a standard based bus system. In different embodiments, the standard based bus system could be implemented in Peripheral Component Interconnect (PCI), Microchannel, Small Computer System Interface (SCSI), Industrial Standard Architecture (ISA) and Extended ISA (EISA) architectures, for example. In addition, the functionality provided for in the components and modules of computing device may be combined into fewer components and modules or further separated into additional components and modules.

The computing device is generally controlled and coordinated by operating system software, such as Windows XP, Windows Vista, Windows 7, Windows 8, Windows Server, Embedded Windows, Unix, Linux, Ubuntu Linux, SunOS, Solaris, iOS, Blackberry OS, Android, or other compatible operating systems. In Macintosh systems, the operating system may be any available operating system, such as MAC OS X. In other embodiments, the computing device may be controlled by a proprietary operating system. Conventional operating systems control and schedule computer processes for execution, perform memory management, provide file system, networking, I/O services, and provide a user interface, such as a graphical user interface (GUI), among other things.

The exemplary computing device may include one or more commonly available I/O interfaces and devices 5010, such as a keyboard, mouse, touchpad, touchscreen, and printer. In one embodiment, the I/O interfaces and devices 5010 include one or more display devices, such as a monitor or a touchscreen monitor, that allows the visual presentation of data to a user. More particularly, a display device provides for the presentation of GUIs, application software data, and multimedia presentations, for example. The computing device may also include one or more multimedia devices 5040, such as cameras, speakers, video cards, graphics accelerators, and microphones, for example.

In the embodiment of the imaging system tool of FIG. 46, the I/O interfaces and devices 5010 provide a communication interface to various external devices. In the embodiment of FIG. 46, the computing device is electronically coupled to a network 5060, which comprises one or more of a LAN, WAN, and/or the Internet, for example, via a wired, wireless, or combination of wired and wireless, communication link 5015. The network 5060 communicates with various computing devices and/or other electronic devices via wired or wireless communication links.

According to FIG. 46, in some embodiments, images to be processed according to methods and systems described herein, may be provided to the computing system 5000 over the network 5060 from one or more data sources 5076. The data sources 5076 may include one or more internal and/or external databases, data sources, and physical data stores. The data sources 5076 may include databases storing data to be processed with the imaging system 5050 according to the systems and methods described above, or the data sources 5076 may include databases for storing data that has been processed with the imaging system 5050 according to the systems and methods described above. In some embodiments, one or more of the databases or data sources may be implemented using a relational database, such as Sybase, Oracle, CodeBase, MySQL, SQLite, and Microsoft® SQL Server, as well as other types of databases such as, for example, a flat file database, an entity-relationship database, and object-oriented database, NoSQL database, and/or a record-based database.

In the embodiment of FIG. 46, the computing system 5000 includes an imaging system module 5050 that may be stored in the mass storage device 5020 as executable software codes that are executed by the CPU 5005. These modules may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. In the embodiment shown in FIG. 46, the computing system 5000 is configured to execute the imaging system module 5050 in order to perform, for example, automated low-level image processing, automated image registration, automated image assessment, automated screening, and/or to implement new architectures described above.

In general, the word "module," as used herein, refers to logic embodied in hardware or firmware, or to a collection of software instructions, possibly having entry and exit points, written in a programming language, such as, for example, Python, Java, Lua, C and/or C++. A software module may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software modules configured for execution on computing devices may be provided on a computer readable medium, such as a compact disc, digital video disc, flash drive, or any other tangible medium. Such software code may be stored, partially or fully, on a memory device of the executing computing device, such as the computing system 5000, for execution by the computing device. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The block diagrams disclosed herein may be implemented as modules. The modules described herein are preferably implemented as software modules, but may be represented in hardware or firmware. Generally, the modules described herein refer to logical modules that may be combined with other modules or divided into sub-modules despite their physical organization or storage.

IX. Additional Embodiments

Each of the processes, methods, and algorithms described in the preceding sections may be embodied in, and fully or partially automated by, code modules executed by one or more computer systems or computer processors comprising computer hardware. The code modules may be stored on any type of non-transitory computer-readable medium or computer storage device, such as hard drives, solid state memory, optical disc, and/or the like. The systems and modules may also be transmitted as generated data signals (for example, as part of a carrier wave or other analog or digital propagated signal) on a variety of computer-readable transmission mediums, including wireless-based and wired/cable-based mediums, and may take a variety of forms (for example, as part of a single or multiplexed analog signal, or as multiple discrete digital packets or frames). The processes and algorithms may be implemented partially or wholly in application-specific circuitry. The results of the disclosed processes and process steps may be stored, persistently or otherwise, in any type of non-transitory computer storage such as, for example, volatile or non-volatile storage.

The various features and processes described above may be used independently of one another, or may be combined in various ways. All possible combinations and subcombinations are intended to fall within the scope of this disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed example embodiments. The example systems and components described herein may be configured differently than described. For example, elements may be added to, removed from, or rearranged compared to the disclosed example embodiments.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment. The term "including" means "included but not limited to." The term "or" means "and/or".

Any process descriptions, elements, or blocks in the flow or block diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

All of the methods and processes described above may be embodied in, and partially or fully automated via, software code modules executed by one or more general purpose computers. For example, the methods described herein may be performed by the computing system and/or any other suitable computing device. The methods may be executed on the computing devices in response to execution of software instructions or other executable code read from a tangible computer readable medium. A tangible computer readable medium is a data storage device that can store data that is readable by a computer system. Examples of computer readable mediums include read-only memory, random-access memory, other volatile or non-volatile memory devices, CD-ROMs, magnetic tape, flash drives, and optical data storage devices.

It should be emphasized that many variations and modifications may be made to the above-described embodiments, the elements of which are to be understood as being among other acceptable examples. All such modifications and variations are intended to be included herein within the scope of this disclosure. The foregoing description details certain embodiments. It will be appreciated, however, that no matter how detailed the foregoing appears in text, the systems and methods can be practiced in many ways. For example, a feature of one embodiment may be used with a feature in a different embodiment. As is also stated above, it should be noted that the use of particular terminology when describing certain features or aspects of the systems and methods should not be taken to imply that the terminology is being re-defined herein to be restricted to including any specific characteristics of the features or aspects of the systems and methods with which that terminology is associated.

What is claimed is:

1. A computing system comprising:
   one or more hardware computer processors; and
   one or more storage devices configured to store software instructions configured for execution by the one or more hardware computer processors in order to cause the computing system to:
   access retinal images related to a patient, each of the retinal images comprising a plurality of pixels;
   for each of the retinal images, designate a first set of the plurality of pixels as active pixels including interesting retinal image regions;
   for each of the retinal images, compute a first vector of numbers comprising pixel-level descriptors for each of the active pixels;
   for each of the retinal images, provide a first classification for each of the active pixels using supervised learning utilizing the corresponding first vector of numbers;
   for each of the retinal images, compute a second vector of numbers including one or more of:
      a first histogram of pixel-level classifier decision statistics computed during the first classification;
      a third vector of numbers computed by obtaining a nearest codeword of pixel-level descriptors aggregated as a second histogram of codeword frequencies in each of the retinal images, wherein a set of codewords is computed from a representative set of images; and
      a third histogram of active region-level decision statistic numbers computed by: grouping neighboring pixels detected in the first set of the plurality of pixels into active regions, computing a number representing each of the active regions using one or more of: mean, median, maximum, or minimum of pixel-level classifier decision statistics computed in the first classification for each pixel that is part of at least one active region, wherein the third histogram is computed over the active regions detected in each of the retinal images; and
   provide a second classification for one or more of: the plurality of pixels, an interesting region within one of the retinal images, one of the retinal images in its entirety, or a collection of the retinal images, using supervised learning.

2. The computing system of claim 1, wherein the computing system is further configured to, resize at least one of the retinal images to a standard size image such that dimensions of the standard size image are determined using field of view information provided or inferred from a structure in the at least one retinal image or using a diameter of a fundus mask.

3. The computing system of claim 1, wherein the computing system is further configured to process a plurality of images obtained from a single patient imaging session or encounter.

4. The computing system of claim 1, wherein the computing system is further configured to process a plurality of images from a single patient session or encounter such that the second vector of numbers for at least a subset of the plurality of images are combined with or without further processing to obtain a fourth vector of numbers.

5. The computing system of claim 1, wherein the computing system is further configured to train one or more classifiers such that each of the one or more classifiers can be used in classification of different abnormalities or diseases and to use the set of classifiers to ascertain presence, absence or severity of plurality of diseases, abnormalities, or lesions.

6. The computing system of claim 1, wherein the computing system is further configured to utilize one or more thresholds for different abnormalities applied on a computed decision statistic at each pixel, to infer an absence or presence of one of a plurality of diseases, lesions, or abnormalities.

7. The computing system of claim 1, wherein the computing system is further configured to run in a telemedicine architecture and to receive a request for an analysis from a remote computing system that is in a different geographic location than the computing system.

8. The computing system of claim 1, wherein the retinal image is one or more of: a retinal fundus photograph, a widefield retinal fundus photograph, an ultra-widefield retinal fundus photograph, or an image obtained using fluorescein angiography, the plurality of diseases includes one or more of: diabetic retinopathy, cytomegalovirus retinitis, retinopathy of prematurity, clinical myopia, hypertensive retinopathy, stroke, cardiovascular disease, glaucoma, macular degeneration, Alzheimer's, or macular edema.

9. The computing system of claim 1, wherein the computing system is further configured to designate a neighboring group of pixels as being part of a lesion.

10. A computer implemented method comprising:
   accessing retinal images related to a patient, each of the retinal images comprising a plurality of pixels;
   for each of the retinal images, designating a first set of the plurality of pixels as active pixels including interesting retinal image regions;
   for each of the retinal images, computing a first vector of numbers comprising pixel-level descriptors for each of the active pixels;
   for each of the retinal images, providing a first classification for each of the active pixels using supervised learning utilizing the corresponding first vector of numbers;
   for each of the retinal images, computing a second vector of numbers including one or more of:
      a first histogram of pixel-level classifier decision statistics computed during the first classification;
      a third vector of numbers computed by obtaining a nearest codeword of pixel-level descriptors aggregated as a second histogram of codeword frequencies in each of the retinal images, wherein a set of codewords is computed from a representative set of images; and
      a third histogram of active region-level decision statistic numbers computed by: grouping neighboring pixels detected in the first set of the plurality of pixels into active regions, computing a number representing each of the active regions using one or more of: mean, median, maximum, or minimum of pixel-level classifier decision statistics computed in the first classification for each pixel that is part of at least one active region, wherein the third histogram is computed over the active regions detected in each of the retinal images; and providing a second classification for one or more of: the plurality of pixels, an interesting region within one of the retinal images, one of the retinal images in its entirety, or a collection of the retinal images, using supervised learning.

11. The computer implemented method of claim 10, further comprising resizing at least one of the retinal images to a standard size image such that dimensions of the standard size image are determined using field of view information provided or inferred from a structure in the at least one retinal image or using a diameter of a fundus mask.

12. The computer implemented method of claim 10, further comprising: processing a plurality of images obtained from a single patient imaging session or encounter.

13. The computer implemented method of claim 10, further comprising processing a plurality of images from a single patient session or encounter such that the second vector of numbers for at least a subset of the plurality of images are combined with or without further processing to obtain a fourth vector of numbers.

14. The computer implemented method of claim 10, further comprising: training one or more classifiers such that each of the one or more classifiers can be used in classification of different abnormalities or diseases and to use the set of classifiers to ascertain presence, absence or severity of plurality of diseases, abnormalities, or lesions.

15. The computer implemented method of claim 10, further comprising: utilizing one or more thresholds for different abnormalities applied on a computed decision statistic at each pixel, to infer an absence or presence of one of a plurality of diseases, lesions, or abnormalities.

16. The computer implemented method of claim 10, wherein the computer implemented method is performed in a telemedicine architecture and the computer implemented method further comprises: receiving a request for an analysis from a remote computing system that is in a different geographic location than where the computer implemented method is being performed.

17. The computer implemented method of claim 10, wherein the retinal image is one or more of: a retinal fundus photograph, a widefield retinal fundus photograph, an ultra-widefield retinal fundus photograph, or an image obtained using fluorescein angiography, the plurality of diseases includes one or more of: diabetic retinopathy, cytomegalovirus retinitis, retinopathy of prematurity, clinical myopia, hypertensive retinopathy, stroke, cardiovascular disease, glaucoma, macular degeneration, Alzheimer's, or macular edema.

18. The computer implemented method of claim 10, further comprising: designating a neighboring group of pixels as being part of a lesion.

19. Non-transitory computer storage that stores executable program instructions that, when executed by one or more computing devices, configure the one or more computing devices to perform operations comprising:

accessing retinal images related to a patient, each of the retinal images comprising a plurality of pixels;

for each of the retinal images, designating a first set of the plurality of pixels as active pixels including interesting retinal image regions;

for each of the retinal images, computing a first vector of numbers comprising pixel-level descriptors for each of the active pixels;

for each of the retinal images, computing a second vector of numbers including one or more of:
 a first histogram of pixel-level classifier decision statistics computed during the first classification;
 a third vector of numbers computed by obtaining a nearest codeword of pixel-level descriptors aggregated as a second histogram of codeword frequencies in each of the retinal images, wherein a set of codewords is computed from a representative set of images; and
 a third histogram of active region-level decision statistic numbers computed by: grouping neighboring pixels detected in the first set of the plurality of pixels into active regions, computing a number representing each of the active regions using one or more of: mean, median, maximum, or minimum of pixel-level classifier decision statistics computed in the first classification for each pixel that is part of at least one active region, wherein the third histogram is computed over the active regions detected in each of the retinal images; and providing a second classification for one or more of: the plurality of pixels, an interesting region within one of the retinal images, one of the retinal images in its entirety, or a collection of the retinal images using supervised learning.

20. The non-transitory computer storage of claim 19, further comprising resizing at least one of the retinal images to a standard size image such that dimensions of the standard size image are determined using field of view information provided or inferred from a structure in the at least one retinal image or using a diameter of a fundus mask.

21. The non-transitory computer storage of claim 19, further comprising: processing a plurality of images obtained from a single patient imaging session or encounter.

22. The non-transitory computer storage of claim 19, further comprising: processing a plurality of images from a single patient session or encounter such that the second vector of numbers for at least a subset of the plurality of images are combined with or without further processing to obtain a fourth vector of numbers.

23. The non-transitory computer storage of claim 19, further comprising: training one or more classifiers such that each of the one or more classifiers can be used in classification of different abnormalities or diseases and to use the set of classifiers to ascertain presence, absence or severity of plurality of diseases, abnormalities, or lesions.

24. The non-transitory computer storage of claim 19, further comprising: utilizing one or more thresholds for different abnormalities applied on a computed decision statistic at each pixel, to infer an absence or presence of one of a plurality of diseases, lesions, or abnormalities.

25. The non-transitory computer storage of claim 19, wherein the one or more computing devices perform operations in a telemedicine architecture, and the one or more computing devices further perform operations comprising: receiving a request for an analysis from a remote computing system that is in a different geographic location than the one or more computing devices.

26. The non-transitory computer storage of claim 19, wherein the retinal image is one or more of: a retinal fundus photograph, a widefield retinal fundus photograph, an ultra-widefield retinal fundus photograph, or an image obtained using fluorescein angiography, the plurality of diseases includes one or more of: diabetic retinopathy, cytomegalovirus retinitis, retinopathy of prematurity, clinical myopia, hypertensive retinopathy, stroke, cardiovascular disease, glaucoma, macular degeneration, Alzheimer's, or macular edema.

27. The non-transitory computer storage of claim 19, further comprising: designating a neighboring group of pixels as being part of a lesion.

\* \* \* \* \*